United States Patent
Levy et al.

(10) Patent No.: US 9,999,683 B2
(45) Date of Patent: Jun. 19, 2018

(54) METHOD FOR IDENTIFYING AND TREATING A PATIENT HAVING TUMOR LESIONS COMPRISING ADMINISTERING A GENE THERAPY RETROVIRAL VECTOR PARTICLE COMPRISING A MUTATED HSV-THYMIDINE KINASE (HSV-TK) POLYNUCLEOTIDE

(71) Applicant: Epeius Biotechnologies Corporation, San Marino, CA (US)

(72) Inventors: John P. Levy, Lake Elsinore, CA (US); Rebecca A. Reed, Sherman Oaks, CA (US); Joseph McNulty, Pasadena, CA (US); Robert G. Johnson, Jr., Lafayette, CA (US)

(73) Assignee: EPEIUS BIOTECHNOLOGIES CORPORATION, San Marino, CA (US)

( * ) Notice: Subject to any disclaimer, the term of this patent is extended or adjusted under 35 U.S.C. 154(b) by 9 days.

(21) Appl. No.: 14/214,448

(22) Filed: Mar. 14, 2014

(65) Prior Publication Data
US 2014/0294772 A1  Oct. 2, 2014

Related U.S. Application Data

(60) Provisional application No. 61/784,901, filed on Mar. 14, 2013.

(51) Int. Cl.
| | |
|---|---|
| *A61K 48/00* | (2006.01) |
| *C12N 9/12* | (2006.01) |
| *A61K 31/713* | (2006.01) |
| *A61K 31/522* | (2006.01) |
| *C07K 14/005* | (2006.01) |

(52) U.S. Cl.
CPC ............ *A61K 48/00* (2013.01); *A61K 31/522* (2013.01); *A61K 31/713* (2013.01); *A61K 48/005* (2013.01); *C07K 14/005* (2013.01); *C12N 9/1211* (2013.01); *C12Y 207/01021* (2013.01); *C12N 2710/16622* (2013.01); *C12N 2740/13034* (2013.01)

(58) Field of Classification Search
CPC .... A61K 48/00; A61K 31/522; A61K 31/713; A61K 48/005; C07K 14/005; C12N 9/1211; C12N 2710/16622; C12N 2740/13034; C12Y 207/01021
See application file for complete search history.

(56) References Cited

U.S. PATENT DOCUMENTS

| | | | |
|---|---|---|---|
| 4,399,216 A | 8/1983 | Axel et al. | |
| 4,704,362 A | 11/1987 | Itakura et al. | |
| 4,766,075 A | 8/1988 | Goeddel et al. | |
| 4,777,127 A | 10/1988 | Suni et al. | |
| 4,784,950 A | 11/1988 | Hagen et al. | |
| 4,801,542 A | 1/1989 | Murray et al. | |
| 4,851,341 A | 7/1989 | Hopp et al. | |
| 4,897,355 A | 1/1990 | Eppstein et al. | |
| 4,935,349 A | 6/1990 | McKnight et al. | |
| 5,171,678 A | 12/1992 | Behr et al. | |
| 5,219,740 A | 6/1993 | Miller et al. | |
| 5,279,833 A | 1/1994 | Rose | |
| 5,283,185 A | 2/1994 | Epand et al. | |
| 5,705,385 A | 1/1998 | Bally et al. | |
| 5,952,225 A | 9/1999 | Pensiero et al. | |
| 5,962,429 A | 10/1999 | Welsh et al. | |
| 5,976,567 A | 11/1999 | Wheeler et al. | |
| 5,980,935 A | 11/1999 | Kirpotin et al. | |
| 5,981,501 A | 11/1999 | Wheeler et al. | |
| 6,096,335 A | 8/2000 | Thierry | |
| 6,110,745 A | 8/2000 | Zhang et al. | |
| 6,120,798 A | 9/2000 | Allen et al. | |
| 6,825,033 B2 | 11/2004 | Gordon et al. | |
| 7,820,157 B2 | 10/2010 | Hall et al. | |
| 2001/0046491 A1 | 11/2001 | Valerie | |
| 2003/0004405 A1* | 1/2003 | Townsend ............... | A61B 6/032 600/407 |
| 2003/0008398 A1 | 1/2003 | Mueller et al. | |
| 2004/0229361 A1 | 11/2004 | Mason | |
| 2005/0130132 A1 | 6/2005 | Day et al. | |
| 2006/0216299 A1 | 9/2006 | Hitoshi et al. | |
| 2009/0123428 A1 | 5/2009 | Hall et al. | |
| 2009/0176260 A1 | 7/2009 | Wu et al. | |
| 2009/0285783 A1 | 11/2009 | Freytag et al. | |

(Continued)

FOREIGN PATENT DOCUMENTS

| | | |
|---|---|---|
| EP | 0345242 A2 | 6/1988 |
| EP | 1914304 A1 | 4/2008 |

(Continued)

OTHER PUBLICATIONS

Ponomarev et al. (Neoplasia. May-Jun. 2003; 5(3):245-54.) and Najjar et al. (J Nucl Med. Mar. 2009; 50(3):409-16.).*
Najjar et al. "Molecular-genetic PET imaging using an HSV1-tk mutant reporter gene with enhanced specificity to acycloguanosine nucleoside analogs." J Nucl Med. Mar. 2009;50(3):409-16.*
Schagen et al. "Insertion vectors for gene therapy." Gene Ther. Feb. 2000;7(4):271-2. (Year: 2002).*
Roberts J.P. "Insertional Mutagenesis from a Viral Vector." The scientist. May 2005. (Year: 2005).*
PCT/US2014/029814 International Preliminary Report on Patentability dated Sep. 24, 2015.
Bar-Shir et al., "Transforming thymidine into a magnetic resonance imaging probe for gene expression." J. Am. Chem. Soc. Jan. 2013; 135:1617-24.

(Continued)

*Primary Examiner* — Titilayo Moloye
(74) *Attorney, Agent, or Firm* — Wilson Sonsini Goodrich & Rosati

(57) ABSTRACT

Nucleic acid sequences encoding improved Herpes Simplex Virus Thymidine Kinases are provided, including their use in diagnostic and therapeutic applications. The thymidine kinases may be mutated using conservative mutations, non-conservative mutations, or both. Also provided are gene therapeutic systems, including viral and retroviral particles.

24 Claims, 9 Drawing Sheets

(56) References Cited

U.S. PATENT DOCUMENTS

| | | | |
|---|---|---|---|
| 2010/0135902 | A1 | 6/2010 | Roberts et al. |
| 2010/0322861 | A1 | 12/2010 | Gambhir et al. |
| 2011/0178282 | A1 | 7/2011 | Freytag et al. |
| 2011/0189159 | A1 | 8/2011 | Chatterjee et al. |
| 2013/0263296 | A1* | 10/2013 | Pomper .............. A61K 49/0013 800/10 |
| 2014/0271640 | A1 | 9/2014 | Bowdish et al. |
| 2014/0288163 | A1 | 9/2014 | Levy et al. |
| 2015/0307576 | A1 | 10/2015 | Bowdish et al. |

FOREIGN PATENT DOCUMENTS

| | | |
|---|---|---|
| GB | 2200651 A | 8/1988 |
| JP | 2006524057 A | 10/2006 |
| KR | 10-2011-0005336 A | 1/2011 |
| WO | WO 1990/07936 | 7/1990 |
| WO | WO 1991/02805 | 3/1991 |
| WO | WO 1993/03769 | 3/1993 |
| WO | WO 1993/05162 | 3/1993 |
| WO | WO 1993/10218 | 5/1993 |
| WO | WO 1993/11230 | 6/1993 |
| WO | WO 1993/19191 | 9/1993 |
| WO | WO 1993/25234 | 12/1993 |
| WO | WO 1993/25698 | 12/1993 |
| WO | WO 1994/03622 | 2/1994 |
| WO | WO 1994/12649 | 6/1994 |
| WO | WO 1994/28938 | 12/1994 |
| WO | WO 1995/00655 | 1/1995 |
| WO | WO 1995/11984 | 5/1995 |
| WO | WO 1998/58630 | 12/1998 |
| WO | WO 2001/06574 | 1/2001 |
| WO | WO-2004093810 A2 | 11/2004 |
| WO | WO-2007109335 A2 | 9/2007 |
| WO | WO-2008054826 A2 | 5/2008 |
| WO | WO-2008054826 A3 | 12/2008 |
| WO | WO 2010/071587 A1 | 6/2010 |
| WO | WO 2014/153205 A1 | 9/2014 |
| WO | WO 2014/153258 A2 | 9/2014 |
| WO | WO 2014/153258 A3 | 1/2015 |

OTHER PUBLICATIONS

Behr, J. "Gene transfer with synthetic cationic amphiphiles: prospects for gene therapy." Bioconjugate Chemistry, 5:382-389 (1994).
Bender, et al., J. Virol., vol. 61, pp. 1639-1649 (1987).
Bottger, et al., "The central half of Pit2 is not required for its function as a retroviral receptor." J Virol. Sep. 2004;78(17):9564-9567.
Bouvet et al., "In vivo color-coded imaging of the interaction of colon cancer cells and splenocytes in the formation of liver metastases." Cancer Res. Dec. 1, 2006;66(23):11293-11297.
Chalmers et al., "Elimination of the truncated message from the herpes simplex virus thymidine kinase suicide gene." Mol. Ther. 4:146-148 (2001).
Chaudry et al., Gibbon ape leukemia virus receptor functions of Type III phosphate transporters from CHOK1 cells are disrupted by two mechanisms. J. Virol. Apr. 1999; 73:2916-2920.
Chen et al., "FL-CTL assay: fluorolysometric determination of cell-mediated cytotoxicity using green fluorescent protein and red fluorescent protein expressing target cells." J Immunol Methods. May 2005;300(1-2):100-114.
Chen et al., "Micro-positron emission tomography imaging of cardiac gene expression in rats using bicistronic adenoviral vector-mediated gene delivery." Circulation. Mar. 23, 2004;109(11):1415-1420.
Chin et al., "Semiautomated radiosynthesis and biological evaluation of [$^{18}$F]FEAU: a novel PET imaging agent for HSV1-tk/sr39tk reporter gene expression." Mol Imaging Biol. Mar.-Apr. 2008;10(2):82-91.
Chu et al. "SV40 DNA transfection of cells in suspension: analysis of efficiency of transcription and translation of T-antigen." Gene 13:197-202 (1981).

Curiel, D. et al., "High-efficiency gene transfer mediated by adenovirus coupled to DNA-polylysine complexes." Hum. Gene Ther. (1992) 3:147-154.
Czako, et al., "The herpes simplex virus thymidine kinase gene as a conditional negative-selection marker gene in *Arabidopsis thaliana*." Plant Physiol. Mar. 1994;104(3):1067-1071.
Dahle, et al., "Gap junctional intercellular communication is not a major mediator in the bystander effect in photodynamic treatment of MDCK II cells." Radiat Res. Sep. 2000;154(3):331-341.
Deroose et al., "Multimodality imaging of tumor xenografts and metastases in mice with combined small-animal PET, small-animal CT, and bioluminescence imaging." J Nucl Med. Feb. 2007;48(2):295-303.
Farrell et al., "Fusion defective gibbon ape leukemia virus vectors can be rescued by homologous but not heterologous soluble envelope proteins." J. Virol. May 2002; 76:4267-4274.
Farrell et al., "New structural arrangement of the extracellular regions of the phosphate transporter SLC20A1, the receptor for gibbon ape leukemia virus." J. Biol. Chem. Oct. 2009; 284:29979-29987.
Fasbender et al. "Complexes of adenovirus with polycationic polymers and cationic lipids increase the efficiency of gene transfer in vitro and in vivo." J. Biol. Chem. 272:6479-6489.
Feldman et al., "Identification of an extracellular domain within the Human PiT-2 receptor that is required for amphotrophic murine leukemia virus binding." J. Virol. Jan. 2004; 78:595-602.
Fuchita et al., Bacterial cytosine deaminase mutants created by molecular engineering show improved 5-fluorocytosine-mediated cell killing in vitro and in vivo. Cancer Res. Jun. 2009; 69:4791-4799.
Ghosh, P. "Reproducible quantification in PET-CT: Clincal relevance and technological approaches." White Paper; Siemens (Feb. 2012).
Grabarczyk et al., "Expression of PiT-1 and PiT-2 retroviral receptors and transduction efficiency of tumor cells." Acta Biochim. Pol. 2002; 49:333-339.
Graham, F. et al. "A new technique for the assay of infectivity of human adenovirus 5 DNA." Virology 52(2):456-467 (1973).
Green et al., "A tracer kinetic model for $^{18}$F-FHBG for quantitating herpes simplex virus type 1 thymidine kinase reporter gene expression in living animals using PET." J Nucl Med. Sep. 2004;45(9):1560-1570.
Green et al., "Indirect monitoring of endogenous gene expression by positron emission tomography (PET) imaging of reporter gene expression in transgenic mice." Mol Imaging Biol. Jan. 2002;4(1):71-81.
Hawley-Nelson, P. et al. "LipofectAMINE reagent: a new, higher efficiency polycationic liposome transfection reagent." Focus 15(3):73-79 (1993).
Hinnen, et al., "Transformation of yeast." Proc Natl Acad Sci U S A. Apr. 1978;75(4):1929-1933.
Hodgson and Solaiman, "Virosomes: cationic liposomes enhance retroviral transduction." Nature Biotechnology 14:339-342 (1996).
Hoffman et al., "Subcellular imaging in the live mouse." Nat Protoc. 2006;1(2):775-782.
Hoffman RM. "In vivo imaging with fluorescent proteins: the new cell biology." Acta Histochem. 2004;106(2):77-87.
Hopp, et al., "A short polypeptide marker sequence useful for recombinant protein identification and purification." Natural Biotechnology 1988; 6:1204-1210.
Jellinek, D. et al. "Potent 2'-amino-2'-deoxypyrimidine RNA inhibitors of basic fibroblast growth factor." (1995) Biochemistry 34:11363-11372.
Johnson et al., "Titration of variant HSV1-tk gene expression to determine the sensitivity of 18F-FHBG PET imaging in a prostate tumor." J Nucl Med. May 2009;50(5):757-764.
Kim et al., "Quantitative micro positron emission tomography (PET) imaging for the in vivo determination of pancreatic islet graft survival." Nat Med. Dec. 2006;12(12):1423-1428.
Lee et al., "Stem cell-mediated accelerated bone healing observed with in vivo molecular and small animal imaging technologies in a model of skeletal injury." J Orthop Res. Mar. 2009;27(3):295-302.

(56) References Cited

OTHER PUBLICATIONS

Leventis, R., et al., "Interactions of mammalian cells with lipid dispersions containing novel metabolizable cationic amphiphiles." Biochem. Biophys. Acta 1023:124-132 (1990).
Lin Y., et al., "Modified RNA sequence pools for in vitro selection." (1994) Nucl. Acids Res. 22(24):5229-5234.
Luker, et al., "Noninvasive imaging of protein-protein interactions in living animals." Proc Natl Acad Sci U S A. May 14, 2002;99(10):6961-6966.
MacDonald et al., "Effect of changes in the expression of the amphotrophic retroviral receptor PiT-2 on transduction efficiency and viral titer: Implications for gene therapy." Hum. Gene Ther. Mar. 2000; 11:587-595.
McElroy et al., "Fluorescent LYVE-1 antibody to image dynamically lymphatic trafficking of cancer cells in vivo." J Surg Res. Jan. 2009;151(1):68-73.
Mescic et al. "C-5 hydroxyethyl and hydroxypropyl acyclonucleosides as substrates for thymidine kinase of Herpes simplex virus type 1 (HSV-1 TK): Syntheses and biological evaluation." Molecules 2013; 18:5104-24.
Miller et al, "Murine retroviruses use at least six different receptors for entry into *Mus dunni* cells." J. Virol. Jun. 1997; 9:4531-4535.
Miller et al., "Improved retroviral vectors for gene transfer and expression." Biotechniques Oct. 1989; 7(9):980-982; 984-986; 989-990.
Miller, A.D. "Retrovirus packaging cells." Human Gene Therapy 1990; 1(1): 5-14.
Miyagawa et al, "PET of cardiac transgene expression: comparison of 2 approaches based on herpesviral thymidine kinase reporter gene." J Nucl Med. Nov. 2004;45(11):1917-1923.
Muller et al., "Synthesis and pre-clinical evaluation of a new C-6 alkylated pyrimidine derivative as a PET imaging agent for HSV1-tk gene expression." Am. J. Nucl. Med. Mol. Imaging 2013; 3:71-84.
Najjar, et al., "Molecular-genetic PET imaging using an HSV1-tk mutant reporter gene with enhanced specificity to acycloguanosine nucleoside analogs." J Nucl Med. Mar. 2009;50(3):409-416.
Naviaus et al., "The pCL vector system: rapid production of helper-free, high-titer, recombinant retroviruses." J. Virol. Aug. 1996; 70:5701-5705.
Orlic et al., "The level of mRNA encoding the amphotrophic retrovirus receptor in mouse and human hematopoietic stem cells is low and correlates with with the efficiency of retrovirus transduction." Proc. Nat'l Acad. Sci Oct. 1996; 93:11097-11102.
Pagratis, N., et al., "Potent 2'-amino-, and 2'-fluoro-2'-deoxyribonucleotide RNA inhibitors of keratinocyte growth factor." (1997) Nature Biotechnol. 15:68-73.
Pañda et al., "Adeno-associated virus liver transduction efficiency measured by in vivo [18F]FHBG positron emission tomography imaging in rodents and nonhuman primates." Hum Gene Ther. Aug. 2011;22(8):999-1009.
Paszkowski, et al., "Direct gene transfer to plants. 1984." Biotechnology. 1992;24:387-392.
PCT/US14/29600 International Search Report and Written Opinion dated Aug. 18, 2014.
PCT/US14/29814 International Search Report and Written Opinion dated Oct. 24, 2014.
Peñuelas et al., "Positron emission tomography imaging of adenoviral-mediated transgene expression." Liver Cancer Patients Gastro (2005)128:1787.
Ponomarev, et al., "A novel triple-modality reporter gene for whole-body fluorescent, bioluminescent, and nuclear noninvasive imaging." Eur J Nucl Med Mol Imaging. May 2004;31(5):740-751.
Puyal, C., et al., "A new cationic liposome encapsulating genetic material. A potential delivery system for polynucleotides." Eur. J. Biochem. 228(3):697-703 (1995).
Roelants et al., "Comparison between adenoviral and retroviral vectors for the transduction of the thymidine kinase PET reporter gene in rat mesenchymal stem cells." J Nucl Med. Nov. 2008;49(11):1836-1844.

Sangro et al., "A phase I clinical trial of thymidine kinase-based gene therapy in advanced hepatocellular carcinoma." Can. Gene Ther. (2010) 17: 837-843.
Sen et al., "Noninvasive imaging of ex vivo intracoronarily delivered nonviral therapeutic transgene expression in heart." Mol Ther. Jul. 2005;12(1):49-57.
Shankar et al., "Consensus recommendations for the use of 18F-FDG as an indicator of therapeutic response in National Cancer Institute trials." J. Nucl. Med. Jun. 2006;47:1059-66.
Shu et al., "Visualization of a primary anti-tumor immune response by positron emission tomography." Proc Natl Acad Sci U S A. Nov. 29, 2005;102(48):17412-17417.
Sliva et al., "Murine leukemia virus (MLV) replication monitored with fluorescent proteins." Virol J. Dec. 20, 2004;1:14.
Stamatatos, L., et al., "Interactions of cationic lipid vesicles with negatively charged phospholipid vesicles and biological membranes." Biochemistry 27:3917-3925 (1988).
Stolworthy et al., "Yeast cytosine deaminase mutants with increased thermostability impart sensitivity to 5-fluorocytosine." J. Mol. Biol. Mar. 2008; 377:854-869.
Study record detail for clinical trial NCT00185848.
Study record detail for clinical trial NCT00871702.
Study record detail for clinical trial NCT01082926.
Stuelton et al., "Lentiviral reporter constructs for fluorescence tracking of the temporospatial pattern of Smad3 signaling." Biotechniques. Sep. 2007;43(3):289-90, 292, 294.
Su et al., "Quantitation of cell number by a positron emission tomography reporter gene strategy." Mol Imaging Biol. May-Jun. 2004;6(3):139-148.
Sundaresan et al., "MicroPET imaging of Cre-loxP-mediated conditional activation of a herpes simplex virus type 1 thymidine kinase reporter gene." Gene Ther. Apr. 2004;11(7):609-618.
Tsuji et al., Dual-color imaging of nuclear-cytoplasmic dynamics, viability, and proliferation of cancer cells in the portal vein area. Cancer Res. Jan. 1, 2006;66(1):303-306.
Willmann et al., "Imaging gene expression in human mesenchymal stem cells: from small to large animals." Radiology. Jul. 2009;252(1):117-127.
Wu et al., "Molecular imaging of the kinetics of vascular endothelial growth factor gene expression in ischemic myocardium." Circulation. Aug. 10, 2004;110(6):685-691.
Xiong et al., "Imaging chemically modified adenovirus for targeting tumors expressing integrin alphavbeta3 in living mice with mutant herpes simplex virus type 1 thymidine kinase PET reporter gene." J Nucl Med. Jan. 2006;47(1):130-139.
Xu et al., "Primate gammaretroviruses require an ancillary factor not required for murine gammaretroviruses to infect BHK cells." J. Virol. Apr. 2011; 85:3498-3506.
Yaghoubi et al, "Imaging progress of herpes simplex virus type 1 thymidine kinase suicide gene therapy in living subjects with positron emission tomography." Cancer Gene Ther. Mar. 2005;12(3):329-339.
Yaghoubi et al., "Human pharmacokinetic and dosimetry studies of [(18)F]FHBG: a reporter probe for imaging herpes simplex virus type-1 thymidine kinase reporter gene expression." J Nucl Med. Aug. 2001;42(8):1225-1234.
Yaghoubi et al., "PET imaging of herpes simplex virus type 1 thymidine kinase (HSV1-tk) or mutant HSV1-sr39tk reporter gene expression in mice and humans using [$^{18}$F]FHBG." Nat Protoc. 2006;1(6):3069-3075.
Yaghoubi et al., "Preclinical safety evaluation of $^{18}$F-FHBG: a PET reporter probe for imaging herpes simplex virus type 1 thymidine kinase (HSV1-tk) or mutant HSV1-sr39tk's expression." J Nucl Med. Apr. 2006;47(4):706-715.
Yaghoubi, et al., "Noninvasive detection of therapeutic cytolytic T cells with 18F-FHBG PET in a patient with glioma." Nat Clin Pract Oncol. Jan. 2009;6(1):53-58.
Yamamoto et al., "Cellular dynamics visualized in live cells in vitro and in vivo by differential dual-color nuclear-cytoplasmic fluorescent-protein expression." Cancer Res. Jun. 15, 2004;64(12):4251-4256.

(56) References Cited

OTHER PUBLICATIONS

Yamamoto et al., "Real-time imaging of individual fluorescent-protein color-coded metastatic colonies in vivo." Clin Exp Metastasis. 2003;20(7):633-638.
Yamauchi et al., "Color-coded real-time subcellular fluorescence imaging of the interaction between cancer and host cells in live mice." Anticancer Res. Jan. 2012;32(1):39-43.
Yang et al., "Real-time whole-body imaging of an orthotopic metastatic prostate cancer model expressing red fluorescent protein." Prostate. Mar. 1, 2005;62(4):374-379.
Yu, et al., "Lentivirus-based DsRed-2-transfected pancreatic cancer cells for deep in vivo imaging of metastatic disease." Methods Mol Biol. 2012;872:69-83.
Zeijl et al., "A human amphotrophic retrovirus receptor is a second member of the gibbon ape leukemia virus receptor family." Proc. Nat'l Acad. Sci. Feb. 1994; 91:1168-1172.
Zhou et al., "Lentivirus-based DsRed-2-transfected pancreatic cancer cells for deep in vivo imaging of metastatic disease." J Surg Res. Nov. 2009;157(1):63-70.
Degreve et al. Selective abolishment of pyrimidine nucleoside kinase activity of herpes simplex virus Type 1 thymidine kinase by mutation of alanine-167 to tyrosine. Molecular Pharmacology 58(6):1326-1332 (2000).
Gambhir et al. A mutant herpes simplex virus Type 1 thymidine kinase reporter gene shows improved sensitivity for imaging reporter gene expression with positron emission tomography. PNAS 97(6):2785-2790 (2000).
Kokoris et al. Characterization of herpes simplex virus Type 1 thymidine kinase mutants engineered for improved ganciclovir or acyclovir activity. Protein Science 11:2267-2272 (2002).
Kokoris et al. In Vitro evaluation of mutant HSV-1 thymidine kinases for suicide gene therapy. Anticancer Research 20:959-964 (2000).
Likar et al. PET imaging of HSV1-tk mutants with acquired specificity toward pyrimidine- and acycloguanosine-based radiotracers. Eur J Nucl Med Mol Imaging, 36:1273-1282 (2009).
Ponomarev et al. Cytoplasmically retargeted HSV1-tk/GFP reported gene mutants for optimization of non-invasive molecular genetic imaging. Neoplasia 5(3):245-254 (2003).
U.S. Appl. No. 14/214,522 Office Action dated May 25, 2016.
U.S. Appl. No. 14/214,522 Restriction Requirement dated Feb. 26, 2016.
Veerisetty et al. HSV1-Specific thymidylate kinase activity in infected cells. Intervirology 24:42-49 (1985).
European Patent Application No. 14769552.2 Extended European Search Report dated Sep. 23, 2016.
Serganova et al., Human reporter genes: potential use in clinical studies. Nuclear Medicine and Biology, 34:791-807, 2007.
Degreve et al., Selective abolishment of pyrimidine nucleoside kinase activity of herpes simplex virus type 1 thymidine kinase by mutation of alanine-167 to tyrosine. Molecular Pharmacology, 58(6):1326-1332, 2000.
European Patent Application No. 14769346.9 extended European Search Report dated Dec. 19, 2016.
Willmon et al., The role of herpes simplex virus-1 thymidine kinase alanine 168 in substrate specificity. The Open Biochemistry Journal, 2:60-66, 2008.
Balzarini et al., Engineering of a single conserved amino acid residue of herpes simplex virus Type 1 thymidine kinase allows a predominant shift from pyrimidine to purine nucleoside phosphorylation. Journal of Biological Chemistry, p. 1-15, 2006.
Degreve, et al., Differential intracellular compartmentalization of herpetic thymidine kinases (TKs) in TK gene-transfected tumor cells: molecular characterization of the nuclear localization signal of herpes simplex virus type 1 TK. Journal of Virology, 72(12):9535-9543, 1998.
Australia Patent Application No. 2014236208 Examination Report No. 1 dated Jun. 26, 2017.
Black et al., Creation of drug-specific herpes simplex virus type 1 thymidine kinase mutants for gene therapy. Proc. Nat. Acad. Sci. USA, 93:3525-3529, 1996.
Black et al., Herpes simplex virus-1 thymidine kinase mutants created by semi-random sequence mutagenesis improve prodrug-mediated tumor cell killing. Cancer Research, 61:3022-3026, 2001.
Luker et al., Noninvasive imaging of protein-protein interactions in living animals. PNAS, 99(10):6961-6966, 2002.
Skotzko et al., Retroviral vector-mediated gene transfer of antisense cyclin G1 (CYCG1) inhibits proliferation of human osteogenic sarcoma cells. Cancer Research, 55:5493-5498, 1995.
U.S. Appl. No. 14/214,522 Office Action dated Jul. 6, 2017.
Japanese Patent Application No. 2016-503157 Office Action dated Dec. 12, 2017.
U.S. Appl. No. 14/214,522 Office Action dated Oct. 25, 2017.
U.S. Appl. No. 14/214,522 Notice of Allowance and Fees Due dated Dec. 26, 2017.
U.S. Appl. No. 14/214,522 Notice of Allowance and Fees Due dated Feb. 1, 2017.

* cited by examiner

METHOD FOR IDENTIFYING AND TREATING A PATIENT HAVING TUMOR LESIONS COMPRISING ADMINISTERING A GENE THERAPY RETROVIRAL VECTOR PARTICLE COMPRISING A MUTATED HSV-THYMIDINE KINASE (HSV-TK) POLYNUCLEOTIDE

CROSS-REFERENCE

This application claims the benefit of U.S. Provisional Application No. 61/784,901, filed on Mar. 14, 2013, which is incorporated herein by reference in its entirety.

This application is related to co-pending U.S. application Ser. No. 14/214,522, filed the same day herewith, which application is incorporated herein by reference in its entirety.

SEQUENCE LISTING

The instant application contains a Sequence Listing which has been submitted electronically in ASCII format and is hereby incorporated by reference in its entirety. The ASCII copy, created on May 12, 2014, is named 30863-722-202-SL.txt and is 37,260 bytes in size.

BACKGROUND OF THE INVENTION

Proliferative diseases, such as cancer, pose a serious challenge to society. Cancerous growths, including malignant cancerous growths, possess unique characteristics such as uncontrollable cell proliferation resulting in, for example, unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation. Cancer encompasses a large category of medical conditions, affecting millions of individuals worldwide. Cancer cells can arise in almost any organ and/or tissue of the body. Worldwide, more than 10 million people are diagnosed with cancer every year and it is estimated that this number will grow to 15 million new cases every year by 2020. Cancer causes six million deaths every year or 12% of the deaths worldwide.

SUMMARY OF THE INVENTION

Provided herein are methods and compositions for identifying subjects or patients that are capable of benefiting from gene therapy treatment. More specifically, provided herein are methods and compositions for identifying subjects or patients that express in sufficient quantities a therapeutic protein included in a gene therapy agent. Preferably the therapeutic protein is an enzyme, more specifically viral thymidine kinase or mutant viral thymidine kinase.

Accordingly, provided herein are methods for identifying a patient capable of benefiting from gene therapy treatment comprising administering a gene therapy retroviral particle comprising an HSV-TK polynucleotide to the patient; administering to the patient a substrate of HSV-TK attached to a radioactive tracer; measuring the relative amount and location of the radioactive signal present in the patient; and determining the location of lesions in the patient, wherein patients with: radioactive signals above a certain threshold, and location of the radioactive signal correlating with lesions measured in step (d) of the patient, are identified as capable of benefiting from gene therapy treatment.

In some embodiments, the substrate of HSV-TK is chosen from the group consisting of FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-, ganciclovir- and penciclovir-like side chains. In yet other embodiments, the substrate of HSV-TK is FHBG (9-(4-fluoro-3-(hydroxymethyl)butyl]guanine).

In still other embodiments, the radioactive tracer is $^{18}F$, $^{64}Cu$, $^{99m}Te$, $^{11}C$, $^{14}C$, $^{124}I$, $^{123}I$, $^{131}I$, $^{15}O$, $^{13}N$ and/or $^{82}RbCl$. In other embodiments, the radioactive tracer is $^{18}F$.

In one embodiment, the HSV-TK substrate is [$^{18}F$]FHBG (9-(4-$^{18}F$-fluoro-3-(hydroxymethyl)butyl]guanine). In still other embodiments, the radioactive tracer signal is measured using positron emission tomography (PET) scanning.

In still other embodiments, the threshold level is at least above 2.0 SUV (standardized uptake value) or at least 20% above background on a PET scan, or between about 1.0 SUV and about 3.0 SUV, or between about 20% to about 40% above background on a PET scan.

In some embodiments, the methods disclosed herein further comprises treating the patient with the HSV-TK retroviral particle.

In still other embodiments, the viral nuclear localization sequence (NLS) of the encoded HSV-TK polynucleotide is mutated. In yet other embodiments, the thymidine kinase polynucleotide is mutated to include a nuclear export sequence (NES) at or near the amino terminus of the expressed thymidine kinase protein. In one embodiment, the thymidine kinase polynucleotide is mutated to increase substrate binding of the expressed thymidine kinase protein. In another embodiment, the mutation is A168H.

In still other embodiments, the methods disclosed herein further comprises mutating the thymidine kinase polynucleotide to remove the viral nuclear localization sequence (NLS) and include a nuclear export sequence (NES) at or near the amino terminus of the expressed thymidine kinase protein. In some embodiments, the HSV-thymidine kinase polynucleotide is SEQ ID NO: 18.

In one embodiment, the methods disclosed herein further comprises a targeting protein expressed on the viral envelope. In some embodiments, the targeting protein binds to collagen, laminin, fibronectin, elastin, glycosaminoglycans, proteoglycans or RGD. In still other embodiments, the targeting protein binds to collagen. In yet other embodiments, the targeting protein is SEQ ID NO: 25.

Also provided herein are methods and compositions for identifying a patient or subject in need of treatment for lesions and capable of benefiting from gene therapy treatment: a) administering a gene therapy retroviral particle comprising an HSV-TK polynucleotide and transducing cells from the patient with the polynucleotide encoding HSV-thymidine kinase; b) treating the cells with a substrate of HSV-TK attached to a radioactive tracer; c) measuring the relative amount of radioactive signal present in target tissue; d) identifying patients wherein the level of radioactively-labelled HSV-TK substrate is above a threshold; e) determining the location of lesions in the patient; and f) treating said patient or subject with the gene therapy retroviral particle comprising an HSV-TK polynucleotide when the measured radioactive signal in the patient is above a certain threshold, and the location of the measured radioactive signal correlates with lesions measured in step (e) of the patient.

Provided herein are methods and compositions for measuring the enzymatic activity of a transduced HSV-thymidine, the method comprising: a) administering a gene therapy retroviral particle comprising an HSV-TK polynucleotide and transducing cells from the patient with the polynucleotide encoding HSV-thymidine kinase; b) treating the cells with a substrate of HSV-TK attached to a radioactive tracer; and c) measuring the relative amount of radioactive signal present in target tissue.

In addition, provided herein are methods and compositions for determining the level of a tracer signal in a subject or patient after administration of a gene therapy particle, and selecting the subject or patient for treatment with the gene therapy particle when the level of the tracer signal is above a set threshold. In some embodiments, the tracer is a radioactive, luminescent or a fluorescent signal. In some embodiments, the radioactive tracer element is $^{18}$F, $^{64}$Cu, $^{99m}$Te, $^{11}$C, $^{14}$C, $^{124}$I, $^{123}$I, $^{131}$I, $^{15}$O, $^{13}$N and/or $^{82}$RbCl.

In yet other embodiments, provided herein are methods and compositions for determining the level of a radiotracer signal in a subject or patient after administration of a thymidine kinase gene therapy construct, and selecting the subject or patient for treatment with the gene therapy construct when the level of the tracer signal is above a set threshold. In some embodiments, the tracer is a radioactive tracer. In other embodiments, the radioactive tracer element is $^{18}$F, $^{64}$Cu, $^{99m}$Te, $^{11}$C, $^{14}$C, $^{124}$I, $^{123}$I, $^{131}$I, $^{15}$O, $^{13}$N and/or $^{82}$RbCl. In yet other embodiments, the radioactive tracer element is coupled to a nucleoside or synthetic nucleoside target to form a radioactive target. In some embodiments, the nucleoside target is FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, val-ganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-ganciclovir and penciclovir-like side chains. Preferably the radioactive target is [$^{18}$F]FHBG (9-(4-$^{18}$F-fluoro-3-[hydroxymethyl]butyl)guanine).

Also provided herein are methods comprising: (a) determining the level of [$^{18}$F]FHBG signal in a subject; and (b) selecting the subject for treatment with a composition wherein the level of FHBG is above a threshold level. In some embodiments, the threshold level is at least about 2.0 SUV (standardized uptake values) or at least 20% above background signal on a PET scan.

Additionally provided herein is a method comprising: (a) determining the level of [$^{18}$F]FHBG signal in a subject; (b) excluding the subject from treatment with a composition wherein the level of FHBG in the subject is greater than about 2.0 SUV or greater than about 20% above background signal on a PET scan; and (c) administering to said subject an anti-cancer agent.

In some embodiments, the invention provides a method for identifying a subject that is susceptible to a cancer treatment, the method comprising: a) identifying expression of [$^{18}$F]FHBG in the subject; b) treating the subject.

Provided herein is a method of measuring HSV-TK-FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, val-ganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-like, ganciclovir-like and penciclovir-like side chains-mediated bystander effect, the method comprising: a) transducing cells with a polynucleotide encoding HSV-TK and a first fluorescent protein; b) transducing the cells with a polynucleotide encoding a second or bioluminescent protein that is optically discernible from the first fluorescent or bioluminescent protein; c) treating the cells with an agent that becomes cytotoxic upon being phosphorylated by HSV-TK; and d) measuring the relative amount of expression of the first fluorescent protein and the second fluorescent protein. In one embodiment, step d) comprises a Perkin Elmer Plate reader, a fluorimeter; a fluorescent activated cell sorter (FACS); a cellometer; or a spectrophotometer. In another embodiment, step d) comprises measuring fluorescent output of the second fluorescent or bioluminescent protein in vivo in the subject.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
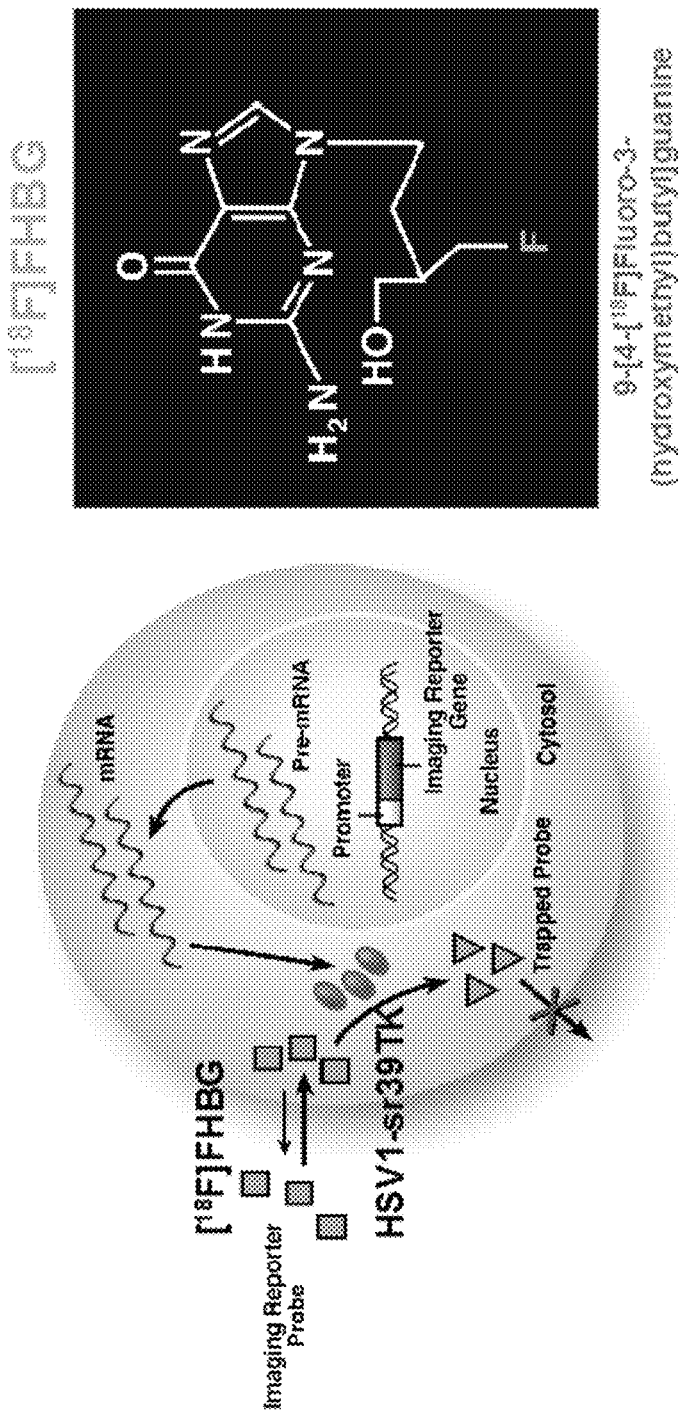
FIG. 1 illustrates the structure of 9-[4-[$^{18}$F]Fluoro-3-(hydroxymethyl)butyl]guanine ([$^{18}$F]FHBG) and its mechanism of inhibition.

Provided herein are methods and compositions for identifying a patient susceptible to treatment with a gene therapy delivery system. Also provided herein are methods and compositions for identifying subjects or patients that are capable of benefiting from gene therapy treatment. Moreover, provided herein are methods and compositions for identifying subjects or patients that express in sufficient quantities a therapeutic protein included in a gene therapy construct. The identification of subjects or patients that are capable of expressing sufficient quantities of a therapeutic protein allows a practitioner to screen and identify patients that can benefit from a particular gene therapy treatment. By doing so, patients and subjects are identified at an early stage that are capable of delivering anti-cancer agents via gene therapy particles to treat, for example, primary and metastatic lesions.

In some embodiments, anti-cancer agents expressed from gene therapy constructs included in viral particles can be administered to patients by intravenous infusion. In yet other embodiments, anti-cancer agents expressed from gene therapy constructs can be administered to patients via inter-arterial infusion. In yet other embodiments, the viral particles containing anti-cancer agents can be administered intra-tumoral. In still other embodiments, anti-cancer agents expressed from gene therapy constructs can be selectively transduced in vitro into target cells.

In yet other embodiments, anti-cancer agents expressed from gene therapy constructs can be targeted to primary and metastatic lesions, thereby delivering a tumor-killing gene to primary and metastatic legions while sparing normal cells and tissues. In some embodiments, the targeting of gene therapy constructs is specific. In yet other embodiments, the targeting of gene therapy constructs is to a cell-surface or extracellular protein. In some embodiments, the cell-surface or extracellular protein is collagen. In yet other embodiments, the targeting of gene therapy constructs is to a specific protein expressed by tumor cells. Such anti-cancer agents provide a powerful tool that can specifically target cancer cells, thereby mitigating the unwanted side-effects of other known cancer therapies.

In some embodiments, the gene therapy construct is a retrovirus. Retroviruses typically have three common open reading frames, gag, pol, and env, which encode the matrix, gag and nucleocapsid structural proteins, encode enzymes including reverse transcriptase, integrase and protease, and encode envelope proteins and transmembrane fusogenic proteins, respectively. Typically, retroviral vector particles are produced by packaging cell lines that provide the necessary gag, pol, and env gene products in trans. (Miller, et al., Human Gene Therapy, Vol. 1, pgs. 5-14 (1990)). This approach results in the production of retroviral vector particles which transduce mammalian cells, but are incapable of further replication after they have integrated into the genome of the cell.

In some embodiments, the retrovirus comprises at least one therapeutic protein or payload delivered by the gene therapy construct. In some embodiments, the therapeutic protein or payload is an enzyme. In yet other embodiments, the therapeutic protein or payload is thymidine kinase. In still other embodiments, the thymidine kinase is HSV (herpes simplex virus) thymidine kinase. In yet other embodiments, the thymidine kinase is HSV (herpes simplex virus) thymidine kinase-1.

In some embodiments, the HSV-TK gene therapy construct is optimized with respect to maximal gene expression and tumor kill activity both in vitro and in vivo including cancer gene therapy. In some embodiments, the HSV-TK gene is codon-optimized. In still other embodiments, the HSV-TK gene therapy construct is targeted to a specific tumor cell or tissue. In yet other embodiments, the HSV-TK gene therapy construct is targeted to a cell-surface protein specifically expressed in tumor cells. In still other embodiments, the HSV-TK gene therapy construct is targeted to a cell-surface protein expressed in tumor tissue or cells. In other embodiments, the HSV-TK gene therapy construct is targeted to collagen.

When expressed in vivo in cells, HSV-TK enzymatically cleaves a co-adminstered nucleoside agent, such as ganciclovir, penciclovir, val-ganciclovir, acyclovir and val-aciclovir, and subsequently transforms the co-administered agent into a cytotoxic agent. Mammalian thymidine kinases are insensitive to these co-administered agents. Sensitivity to the cytotoxic agent is therefore only conferred upon tumor cells after expression of the HSV-TK gene. Ganciclovir is converted by the resulting HSV-TK to the monophosphorylated product, which is then converted to di- and triphosphates by host kinases, leading to cytotoxicity and tumor cell death. Viral thymidine kinase therapy has been previously shown to have promise in the treatment of several cancers, including gliomas, hepatoma and melanoma.

HSV-TK also selectively phosphorylates the nucleoside analogue of, for example, 9-[4-$^{18}$F-fluoro-3-(hydroxymethyl)butyl]guanine ([$^{18}$F]FHBG) (FIG. 1), which cleaves the radioactive tracer $^{18}$F from the FHBG molecule. HSV-TK expression can therefore be closely monitored with positron emission tomography (PET) scans.

Accordingly provided herein are methods and compositions for determining the level of a tracer signal in a subject or patient after administration of a gene therapy vector, and selecting the subject or patient for treatment with the gene therapy vector when the level of the tracer signal is above a set threshold. In some embodiments, the tracer is a radioactive, luminescent or a fluorescent signal. In some embodiments, the radioactive tracer element is $^{18}$F, $^{64}$Cu, $^{99m}$Te, $^{11}$C, $^{14}$C, $^{124}$I, $^{123}$I, $^{131}$I, $^{15}$O, $^{13}$N and/or $^{82}$RbCl.

In yet other embodiments, provided herein are methods and compositions for determining the level of a radiotracer signal in a subject or patient after administration of a thymidine kinase gene therapy vector, and selecting the subject or patient for treatment with the gene therapy vector when the level of the tracer signal is above a set threshold. In some embodiments, the tracer is a radioactive tracer. In other embodiments, the radioactive tracer element is $^{18}$F, $^{64}$Cu, $^{99m}$Te, $^{11}$C, $^{14}$C, $^{124}$I, $^{123}$I, $^{131}$I, $^{15}$O, $^{13}$N and/or $^{82}$RbCl. In yet other embodiments, the radioactive tracer element is coupled to a nucleoside or synthetic nucleoside target to form a radioactive target. In some embodiments, the nucleoside target is FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4

(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-ganciclovir and penciclovir-like side chains. Preferably the radioactive target is [$^{18}$F]FHBG (9-(4-$^{18}$F-fluoro-3-[hydroxymethyl]butyl)guanine).

Also provided herein are methods comprising: (a) determining the level of [$^{18}$F]FHBG signal in a subject; and (b) selecting the subject for treatment with a gene therapy composition wherein the level of [$^{18}$F]FHBG is at least about 2.0 SUV or at least 20% above background on a PET scan.

Additionally provided herein is a method comprising: (a) determining the level of [$^{18}$F]FHBG signal in a subject; (b) including the subject with treatment with a composition wherein the level of FHBG in the subject is greater than about 2.0 SUV on PET scan; and (c) administering to said subject an anti-cancer agent.

In some embodiments, the invention provides a method for identifying a subject that is susceptible to a cancer treatment, the method comprising: a) identifying expression of [$^{18}$F]FHBG in the subject; b) treating the subject.

Provided herein is a method of measuring HSV-TK-mediated FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4 (1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-, ganciclovir- and penciclovir-like side chains-mediated bystander effect, the method comprising: a) transducing cells with a polynucleotide encoding HSV-TK and a first fluorescent protein; b) transducing the cells with a polynucleotide encoding a second fluorescent or bioluminescent protein that is optically discernible from the first fluorescent or bioluminescent protein; c) treating the cells with an agent that becomes cytotoxic upon being phosphorylated by HSV-TK; and d) measuring the relative amount of expression of the first fluorescent protein and the second fluorescent protein. In one embodiment, step d) comprises a Perkin Elmer Plate reader, a fluorimeter; a fluorescent activated cell sorter (FACS); a cellometer; or a spectrophotometer. In another embodiment, step d) comprises measuring fluorescent output of the second fluorescent or bioluminescent protein in vivo in the subject.

Also provided herein are methods for determining the level of [$^{18}$F]FHBG signal in a subject and selecting the subject for treatment with a gene therapy composition wherein the level of [$^{18}$F]FHBG is at least about 2.0 SUV or at least 20% above background on a PET scan.

Definitions

Unless defined otherwise, all technical and scientific terms used herein have the same meaning as is commonly understood by one of skill in the art to which the invention(s) belong. All patents, patent applications, published applications and publications, GenBank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, "nucleic acid" refers to a polynucleotide containing at least two covalently linked nucleotide or nucleotide analog subunits. A nucleic acid is generally a deoxyribonucleic acid (DNA), a ribonucleic acid (RNA), or an analog of DNA or RNA. Nucleotide analogs are commercially available and methods of preparing polynucleotides containing such nucleotide analogs are known (Lin et al. (1994) *Nucl. Acids Res.* 22:5220-5234; Jellinek et al. (1995) *Biochemistry* 34:11363-11372; Pagratis et al. (1997) *Nature Biotechnol.* 15:68-73). The nucleic acid is generally single-stranded, double-stranded, or a mixture thereof. For purposes herein, unless specified otherwise, the nucleic acid is double-stranded, or it is apparent from the context.

As used herein, "DNA" is meant to include all types and sizes of DNA molecules including cDNA, plasmids and DNA including modified nucleotides and nucleotide analogs.

As used herein, "nucleotides" include nucleoside mono-, di-, and triphosphates. Nucleotides also include modified nucleotides, such as, but are not limited to, phosphorothioate nucleotides and deazapurine nucleotides and other nucleotide analogs.

The term "polynucleotide" as used herein means a polymeric form of nucleotide of any length, and includes ribonucleotides and deoxyribonucleotides. Such term also includes single- and double-stranded DNA, as well as single- and double-stranded RNA. The term also includes modified polynucleotides such as methylated or capped polynucleotides.

As used herein, the term "subject" refers to animals, plants, insects, and birds into which the large DNA molecules are introduced. Included are higher organisms, such as mammals and birds, including humans, primates, rodents, cattle, pigs, rabbits, goats, sheep, mice, rats, guinea pigs, cats, dogs, horses, chicken and others.

As used herein, "administering to a subject" is a procedure by which one or more delivery agents and/or large nucleic acid molecules, together or separately, are introduced into or applied onto a subject such that target cells which are present in the subject are eventually contacted with the agent and/or the large nucleic acid molecules.

As used herein, "delivery vector" or "delivery vehicle" or "therapeutic vector" or "therapeutic system" refers to both viral and non-viral particles that harbor and transport exogenous nucleic acid molecules to a target cell or tissue. Viral vehicles include, but are not limited to, retroviruses, adenoviruses, lentiviral viruses, herpes viruses and adeno-associated viruses. Non-viral vehicles include, but are not limited to, microparticles, nanoparticles, virosomes and liposomes. "Targeted," as used herein, refers to the use of ligands that are associated with the delivery vehicle and target the vehicle to a cell or tissue. Ligands include, but are not limited to, antibodies, receptors and collagen-binding domains.

As used herein, "delivery," which is used interchangeably with "transduction," refers to the process by which exogenous nucleic acid molecules are transferred into a cell such that they are located inside the cell. Delivery of nucleic acids is a distinct process from expression of nucleic acids.

As used herein, a "multiple cloning site (MCS)" is a nucleic acid region in a plasmid that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector.

As used herein, "origin of replication" (often termed "ori"), is a specific nucleic acid sequence at which replication is initiated. Alternatively an autonomously replicating sequence (ARS) can be employed if the host cell is yeast.

As used herein, "selectable or screenable markers" confer an identifiable change to a cell permitting easy identification of cells containing an expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. In some embodiments, screenable enzymes such as herpes simplex virus thymidine kinase (tk) or chloramphenicol acetyltransferase (CAT) are utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

As used herein, "expression" refers to the process by which nucleic acid is translated into peptides or is transcribed into RNA, which, for example, can be translated into peptides, polypeptides or proteins. If the nucleic acid is derived from genomic DNA, expression includes, if an appropriate eukaryotic host cell or organism is selected, splicing of the mRNA. For heterologous nucleic acid to be expressed in a host cell, it must initially be delivered into the cell and then, once in the cell, ultimately reside in the nucleus.

As used herein, a "therapeutic course" refers to the periodic or timed administration of the vectors disclosed herein within a defined period of time. Such a period of time is at least one day, at least two days, at least three days, at least five days, at least one week, at least two weeks, at least three weeks, at least one month, at least two months, or at least six months. Administration could also take place in a chronic manner, i.e., for an undefined period of time. The periodic or timed administration includes once a day, twice a day, three times a day or other set timed administration.

As used herein, the terms "co-administration," "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments, a therapeutic agent as disclosed in the present application will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, a therapeutic agent and the other agent(s) are administered in a single composition. In some embodiments, a therapeutic agent and the other agent(s) are admixed in the composition. In further embodiments, a therapeutic agent and the other agent(s) are administered at separate times in separate doses.

The term "host cell" denotes, for example, microorganisms, yeast cells, insect cells, and mammalian cells, that can be, or have been, used as recipients for multiple constructs for producing a delivery vector. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, "genetic therapy" involves the transfer of heterologous DNA to the certain cells, target cells, of a mammal, particularly a human, with a disorder or conditions for which therapy or diagnosis is sought. The DNA is introduced into the selected target cells in a manner such that the heterologous DNA is expressed and a therapeutic product encoded thereby is produced. In some embodiments, the heterologous DNA, directly or indirectly, mediates expression of DNA that encodes the therapeutic product. In some embodiments, the heterologous DNA encodes a product, such as a peptide or RNA that mediates, directly or indirectly, expression of a therapeutic product. In some embodiments, genetic therapy is used to deliver a nucleic acid encoding a gene product to replace a defective gene or supplement a gene product produced by the mammal or the cell in which it is introduced. In some embodiments, the introduced nucleic acid encodes a therapeutic compound, such as a growth factor or inhibitor thereof, or a tumor necrosis factor or inhibitor thereof, such as a receptor therefore, that is not generally produced in the mammalian host or that is not produced in therapeutically effective amounts or at a therapeutically useful time. In some embodiments, the heterologous DNA encoding the therapeutic product is modified prior to introduction into the cells of the afflicted host in order to enhance or otherwise alter the product or expression thereof.

As used herein, "heterologous nucleic acid sequence" is generally DNA that encodes RNA and proteins that are not normally produced in vivo by the cell in which it is expressed or that mediates or encodes mediators that alter expression of endogenous DNA by affecting transcription, translation, or other regulatable biochemical processes. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. In some embodiments, antibodies that are encoded by heterologous DNA is secreted or expressed on the surface of the cell in which the heterologous DNA has been introduced.

As used herein, the term "thymidine kinase mutant" refers to not only the specific protein described herein (as well as the nucleic acid sequences which encode these proteins), but derivatives thereof which may include various structural forms of the primary protein which retain biological activity.

As used herein, "unmutated thymidine kinase" refers to a native or wild-type thymidine kinase polypeptide sequence.

As used herein, "suicide gene" refers to a nucleic acid encoding a product, wherein the product causes cell death by itself or in the present of other compounds.

As used herein, the term "mutated" or "replaced by another nucleotide" means a nucleotide at a certain position is replaced at that position by a nucleotide other than that which occurs in the unmutated or previously mutated sequence. That is, in some instances, specific modifications may be made in different nucleotides. In some embodiments, the replacements are made such that the relevant splice donor and/or acceptor sites are no longer present in a gene.

As used herein, a "polar amino acid" refers to amino acid residues Asp (N), Cys (C), Gln (Q), Gly (G), Ser (S), Thr (T) or Tyr (Y).

As used herein, a "non-polar amino acid" refers to amino acid residues Ala (A), Ile (I), Leu (L), Met (M), Phe (F), Pro (P), Trp (W), or Val (V).

As used herein, a "basic amino acid" refers to amino acid residues Arg (R), His (H), or Lys (K).

As used herein, an "acidic amino acid" refers to amino acid residues Asp (D) or Glu (E).

Gene Therapy

Gene therapy involves the transfer of heterologous DNA to certain cells of a mammal, particularly a human, with a disorder or conditions for which therapy or diagnosis is sought. The DNA is introduced into the selected target cells in a manner such that the heterologous DNA is expressed and a therapeutic product encoded thereby is produced.

In some embodiments, the heterologous DNA, directly or indirectly, mediates expression of DNA that encodes the therapeutic product. In some embodiments, the heterologous DNA encodes a product, such as a peptide or RNA that mediates, directly or indirectly, expression of a therapeutic product. In some embodiments, the introduced nucleic acid encodes a therapeutic compound, such as a growth factor or inhibitor thereof, or a tumor necrosis factor or inhibitor thereof, such as a receptor therefore, that is not generally produced in the mammalian host or that is not produced in therapeutically effective amounts or at a therapeutically useful time.

Non-viral and viral methods have been used to deliver heterologous therapeutic DNA into the cell, including viral vector particles derived from retrovirus, adenovirus, adeno-associated viral particles, herpes virus particles, vaccinia virus, lentivirus, pox virus, Semliki virus and pseudotyped viruses.

Accordingly, provided herein are viral constructs for gene transfer to cells either in vivo, ex vivo or in vitro for gene therapy. Such viral vector particles include, but are not limited to retroviral vector particles, adenoviral vector particles, adeno-associated virus particles, herpes virus particles, pseudotyped viruses, lentiviral vector particles, pox virus vector particles, vaccinia virus vector particles and non-viral vectors. Preferably, the viral vector particle is a retroviral vector particle.

Retroviral Constructs

In some embodiments, the vector particle employed for gene therapy use is a retroviral vector particle. In still other embodiments, the retroviral vector particle is derived from Moloney Murine Leukemia Virus and is of the LN series of vectors, such as those hereinabove mentioned, and described further in Bender, et al., J. Virol., Vol. 61, pgs. 1639-1649 (1987) and Miller, et al., Biotechniques, Vol. 7, pgs 980-990 (1989). Such vectors, have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In some embodiments, the retroviral vector particle includes a modified envelope, including at least one polynucleotide encoding at least one heterologous polypeptide to be expressed in a desired cell. The heterologous polypeptide may, in one embodiment, be a therapeutic agent. The therapeutic agent is thymidine kinase, more preferably HSV-TK.

In still other embodiments, therapeutic agents include, but are not limited to, growth factors such as, for example, epidermal growth factor (EGF), vascular endothelial growth factor (VEGF), erythropoietin, G-CSF, GM-CSF, TGFα, TGF-β, and fibroblast growth factor, cytokines, including, but not limited to, interleukins and tumor necrosis factors. Other therapeutic agents include, but are not limited to, anticoagulants, anti-platelet agents, anti-inflammatory agents, tumor suppressor proteins, clotting factors, including Factor VII, Factor VIII and Factor IX, protein S, protein C, antithrombin III and von Willebrand Factor.

In some embodiments, the polynucleotide encoding the therapeutic agent is under the control of a suitable promoter. Suitable promoters which may be employed include, but are not limited to, the retroviral LTR; the SV40 promoter; the cytomegalovirus (CMV) promoter; the Rous Sarcoma Virus (RSV) promoter; the histone promoter; the polIII promoter, the β-actin promoter; inducible promoters, such as the MMTV promoter, the metallothionein promoter; heat shock promoters; adenovirus promoters; the albumin promoter; the ApoAI promoter; B19 parvovirus promoters; human globin promoters; viral thymidine kinase promoters, such as the Herpes Simplex Virus thymidine kinase promoter; retroviral LTRs; human growth hormone promoters, and the MxIFN inducible promoter. The promoter also may be the native promoter which controls the polynucleotide encoding the therapeutic agent.

The polynucleotides encoding the modified envelope polypeptide and the therapeutic agent may be placed into an appropriate vector by genetic engineering techniques known to those skilled in the art. When the modified vector is a retroviral vector particle, the polynucleotides encoding the modified envelope polypeptide and the therapeutic agent are placed into an appropriate retroviral plasmid vector.

The retroviral plasmid vector includes one on more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980-990 (1989), or any other promoter (e.g., cellular promoters such as eukaryotic cellular promoters including, but not limited to, the histone, pol III, and β-actin promoters).

Other viral promoters which may be employed include, but are not limited to, adenovirus promoters, TK promoters, and B19 parvovirus promoters. The selection of a suitable promoter will be apparent to those skilled in the art from the teachings contained herein.

In one embodiment, the retroviral plasmid vector, which includes a polynucleotide encoding the modified envelope and a polynucleotide encoding a therapeutic agent, is employed to transduce a packaging cell line to form a producer cell line, which will generate infectious retroviral vector particles. In one embodiment, the packaging cell line is a "pre-packaging" cell line which includes polynucleotides encoding the gag and pol retroviral proteins, but not the envelope, or env, protein. Such cell lines, upon transduction with the retroviral plasmid vector, generates infectious retroviral particles including the modified, or chimeric, envelope and a polynucleotide encoding the therapeutic agent. The vector may transduce the packaging cells through any means known in the art. Such means include, but are not limited to, electroporation, and use of liposomes, such as hereinabove described, and $CaPO_4$ precipitation. Such producer cells generate infectious retroviral vector particles which include the modified envelope, the wild-type retroviral envelope, a polynucleotide encoding the modified, or chimeric, envelope, and a polynucleotide encoding a therapeutic agent.

In another embodiment, there is provided a packaging cell which includes a nucleic acid sequence encoding a modified chimeric envelope in accordance with the invention, and which may further include nucleic acid sequences encoding the gag and pol proteins. A producer cell for generating viral particles which includes a modified envelope in accordance with the invention is produced by introducing into such packaging cell either a retroviral vector particle or a retroviral plasmid vector, in each case including a polynucleotide encoding a therapeutic agent. The producer cell line thus generates infectious retroviral particles including the modified chimeric envelope and the polynucleotide encoding the therapeutic agent.

Targeted Retroviral Vector Delivery

In some embodiments, provided herein are vector particles having a modified viral surface protein, such as, for example, a modified viral envelope polypeptide, for targeting the vector particle to an extracellular matrix component. The viral surface protein is modified to include a targeting polypeptide including a binding region which binds to, an extracellular matrix component.

In some embodiments, the targeting polypeptide is inserted between two consecutively numbered amino acid residues of the native (i.e., unmodified) receptor binding region of the retroviral envelope. In yet other embodiments, amino acid residues of the receptor binding region may be removed and replaced with the targeting polypeptide.

As an alternative to modifying the receptor binding region, or in addition to the modified receptor binding region, the retroviral particles may have modifications in other regions of the envelope protein such that other regions of the envelope may include the targeting polypeptide, such as, for example, the secretory signal or "leader" sequence, the hinge region, or the body portion. Such modifications may include deletions or substitutions of amino acid residues in the retroviral envelope wherein amino acid residues from regions other than the receptor binding region of the envelope are removed and replaced with the targeting polypeptide, or the targeting polypeptide is placed between consecutively numbered amino acid residues of regions other than the receptor binding region of the viral envelope.

In another alternative embodiment, the retroviral envelope, prior to modification thereof to include the targeting polypeptide which binds to the extracellular matrix component, may be an envelope which includes regions of different tropisms. For example, the retroviral envelope may be a Moloney Murine Leukemia Virus envelope which includes a gp70 protein having an ecotropic portion and an amphotropic and/or xenotropic portion.

In general, the targeting polypeptide includes a binding region which binds to an extracellular matrix component, including, but not limited to, collagen (including collagen Type I and collagen Type IV), laminin, fibronectin, elastin, glycosaminoglycans, proteoglycans, and sequences which bind to fibronectin, such as arginine-glycine-aspartic acid, or RGD, sequences. Binding regions which may be included in the targeting polypeptide include, but are not limited to, polypeptide domains which are functional domains within von Willebrand Factor or derivatives thereof, wherein such polypeptide domains bind to collagen. In one embodiment, the binding region is a polypeptide having the following structural formula: Trp-Arg-Glu-Pro-Ser-Phe-Met-Ala-Leu-Ser. (SEQ ID NO: 25).

In addition to the binding region, the targeting polypeptide may further include linker sequences of one or more amino acid residues, placed at the N-terminal and/or C-terminal of the binding region, whereby such linkers increase rotational flexibility and/or minimize steric hindrance of the modified envelope polypeptide.

HSV-TK

Thymidine kinase is a salvage pathway enzyme which phosphorylates natural nucleoside substrates as well as nucleoside analogues. Generally, thymidine kinase is used therapeutically by administration of a nucleoside analogue such as ganciclovir or acyclovir to a cell expressing thymidine kinase, wherein the thymidine kinase phosphorylates the nucleoside analogue, creating a toxic product capable of killing the cell.

Polynucleotide sequences encoding exogenous thymidine kinase as used herein may be prepared from a wide variety of thymidine kinases. In some embodiments, the thymidine kinase mutant is derived from Herpesviridae thymidine kinase including, for example, both primate herpes viruses, and non-primate herpes viruses such as avian herpes viruses. Representative examples of suitable herpes viruses include, for example, Herpes Simplex Virus (HSV) Type 1, Herpes Simplex Virus Type 2, Varicella zoster Virus, marmoset herpes virus, feline herpes virus type 1, pseudorabies virus, equine herpes virus type 1, bovine herpes virus type 1, turkey herpes virus, Marek's disease virus, herpes virus saimir and Epstein-Barr virus.

Improvements to TK Gene

Disclosed herein, in some embodiments, is a polynucleotide sequence encoding HSV-TK. In some embodiments, the polynucleotide sequence encodes a wild-type HSV-TK amino acid sequence. In some embodiments, the polynucleotide sequence encodes a mutated HSV-TK amino acid sequence.

Exemplary procedures that may be used in preparation of an optimized polynucleotide sequence provided herein include, but are not limited to: codon optimization; correction of splice sites, removal of poly-pyrimidine tracts and excess GC content; addition of single Kozak sequence, removal of unwanted Kozak sequences; inclusion of restriction sites for subcloning into retroviral or other vectors; removal of nuclear localization sequences or addition of nuclear export sequences; addition of mutation sequences; addition of double stop codon sequences; addition of tags, linkers and fusion sequences; preparation of sequence file for submission to gene synthesis company; subcloning of synthesized gene into retroviral vectors; inclusion of fluorescent protein genes into retroviral vectors; inclusion of selectable marker genes into retroviral vectors; preparation of Maxiprep plasmid DNA; transfection of retroviral producer or other cells; lab, pilot or GMP scale production of retrovirus; transduction of target cells with retrovirus; GCV or analogs pro-drug mediated cell kill assay; Hypoxanthine/Aminopterin/Thymidine (HAT) selection assay; selectable marker drug selection procedure to produce retroviral transduced cell lines; fluorescent microscopy and photography to detect and document retroviral transduced target cells; quantitative fluorescent detection of retroviral transduced target cells; Western protein expression assay; other procedures and assays as needed for HSV-TK analysis; or a combination thereof. Protocols for such methods are described herein, are commercially available or are described in the public literature and databases.

In some embodiments, described herein is a method of obtaining an improved HSV-TK sequence. In some embodiments, the method comprises: a) correction and/or removal of splice sites; and/or b) adjustment to a single Kozak sequence. Optionally, in some embodiments, the method further comprises inclusion of restriction sites for subcloning of the HSV-TK sequence. Optionally, or in addition, in some embodiments, the method further comprises removal of nuclear localization sequences.

Provided herein is a polynucleotide sequence encoding a mutated form of viral thymidine kinase from human simplex virus (HSV-TK), wherein the encoded HSV-TK is mutated at amino acid residue 25, 26, 32, 33, 167, 168, or a combination thereof, wherein the polynucleotide sequence is mutated compared to a polynucleotide sequence of SEQ ID NO: 1 or 3. In such sequences, 1, 2, 3, 4, 5, 6, 7, 8, 9, 10, 11, 12, 13, or 14 mutations may be made.

Modifications may be conservative or non-conservative mutations. A mutation may be made such that the encoded amino acid is modified to a polar, non-polar, basic or acidic amino acid.

Provided herein is a polynucleotide sequence encoding a mutated form of thymidine kinase from human simplex virus (HSV-TK), wherein the encoded HSV-TK includes a nuclear export sequence. Provided herein is a polynucleotide sequence encoding a mutated form of thymidine kinase from human simplex virus (HSV-TK), where the encoded HSV-TK is improved in function compared to wild-type HSV-TK and comprises A168H dmNES (CL system=CMV enhancer properly fused to LTR promoter regions), where NES refers to a nuclear export sequence. In one embodiment, a mutant HSV-TKA168HdmNES is a mutant HSV-TK gene for inclusion in Reximmune-C2. In one embodiment, the NES is derived from MAP Kinase Kinase (MAPKK). In yet another embodiment, the polynucleotide sequence for NES is CTGCAGAAAAAGCTGGAAGAGCTGGAACTG-GATGGC (SEQ ID NO: 23). In other embodiments, the NES polypeptide sequence is LQKKLEELELDG (SEQ ID NO: 24).

In some embodiments, disclosed herein are mutations to a polynucleotide sequence encoding Human Simplex Virus Thymidine Kinase (HSV-TK) wherein mutations are not made to the polypeptide sequence of wildtype HSV-TK.

Nucleotide positions are referred to by reference to a position in SEQ ID NO: 1 (wildtype (wt) HSV1-TK nucleotide sequence) or SEQ ID NO: 3 (HSV-TK in Reximmune-C HSV-TK; SR39 mutant and R25G-R26S Mutation of the HSV-TK nuclear localization signal (NLS)).

In one embodiment, a Sac I-Kpn I restriction sites bounding the clonable double stranded oligonucleotides of the mutant HSV-TK SR39 mutant region is provided. See, for example, SEQ ID NOS: 6 and 7, where the Sac I and Kpn I sites are shown on the left and right, respectively. Bold, underlining illustrates the sites where mutations may be made. SEQ ID NOS: 8 and 9 illustrate an exemplary sequence after cutting with Sac I and Kpn I. Exemplary forward and reverse primers that may be used to make the mutations are shown as SEQ ID NOS: 10 and 11.

Exemplary optimized HSV-TK polynucleotide sequences are provided, for example, as SEQ ID NOS: 12-22.

However, when such references are made, the invention is not intended to be limited to the exact sequence as set out in SEQ ID NO: 1 or 3, but includes variants and derivatives thereof. Thus, identification of nucleotide locations in other thymidine kinase sequences are contemplated (i.e., identification of nucleotides at positions which the skilled person would consider to correspond to positions recited in SEQ ID NO: 1 or 3).

In some embodiments, nucleotides are replaced by taking note of the genetic code such that a codon is changed to a different codon which codes for the same amino acid residue. In some embodiments, nucleotides are replaced within coding regions of a HSV-TK encoding nucleic acid sequence, yet the nucleic acid sequence maintains wild type HSV-TK protein expression.

In such embodiments, 5/21 codons contain "C or G" in third position (24%); 0/21 codons contain "C" in third position (0%); 5/21 codons contain "G" in third position (24%); and 16/21 codons contain "A or T" in third position (76%).

In yet other embodiments, 16/21 codons contain "C or G" in third position (76%); 11/21 codons contain "C" in third position (52%); 5/21 codons contain "G" in third position (24%); and 5/21 codons contain "A or T" in third position (24%).

In some embodiments, the following rare codons are not used or are avoided in the coding region of a polynucleotide encoding HSV-TK, or a variant thereof: GCG for alanine; CGA or CGT for arginine; TTA or CTA for leucine; CCG for proline; TCG for serine; ACG for threonine; and GTA for valine.

In some embodiments, altering codons as described herein results in about 2%, about 5%, about 10%, about 15%, about 20%, about 25%, about 30%, about 35%, about 40%, about 45%, about 50%, about 55%, about 60%, about 70%, about 75%, about 80%, about 85%, about 90%, about 95%, or greater percentage increase in activity.

In some embodiments, disclosed herein is a nucleic acid sequence encoding a thymidine kinase wherein at least one nucleotide corresponding to a splice donor site is replaced by another nucleotide. In further embodiments, the nucleotides of the splice acceptor sites are not altered. In some embodiments, at least one nucleotide corresponding to a splice acceptor site is replaced by another nucleotide.

In some embodiments, disclosed herein is a nucleic acid sequence encoding a thymidine kinase wherein at least one of the nucleotides corresponding to splice donor site nucleotides at positions 329 and 330 of a polynucleotide sequence (e.g., SEQ ID NO: 1 or 3) is replaced by another nucleotide. In some embodiments, both of the nucleotides at positions 327 and 555 are replaced by other nucleotides. For example, position 327 may be mutated to an amino acid residue selected from: G to A. Alternately, or in addition, position 555 may be mutated to an amino acid residue selected from: G to A. In one embodiment, the modified HSV-TK has a polynucleotide sequence of SEQ ID NO: 18, in which HSV-TK was improved in the following ways:

```
HSV-TK NESdmNLS A168H, CO & SC
                                        SEQ ID NO: 18
gtcaGCGGCCGCACCGGTACGCGTCCACCATGGCCCTGCAGAAAAGCTG

GAAGAGCTGGAACTGGATGGCAGCTACCCCGGCCACCAGCACGCCAGCGC

CTTCGACCAGGCCGCCCGCAGCCGCGGCCACAGCAACGGCAGCACCGCaC

TGCCGgCCaGGATCTCAGCAGGAGGCCACCGAGGTGCGCCCCGAGCAGAAG

ATGCCCACCCTGCTGCGCGTGTACATCGACGGaCCaCACGGCATGGGCAA

GACCACCACCACCCAGCTGCTGGTGGCCCTGGGCAGCCGCGACGACATCG

TGTACGTGCCCGAGCCCATGACCTACTGGCGCGTGCTGGGCGCCAGCGAG

ACCATCGCCAACATCTACACCCACCCAGCACCGCCTGGACCAaGGCGAGAT

CAGCGCCGGCGACGCCGCCGTGGTGATGACCAGCGCCCAGATtACaATGG

GCATGCCCTACGCCGTGACCGACGCCGTGCTGGCaCCaCACATCGGCGGC

GAGGCCGGCAGCAGCCACGCaCCaCCaCCaGCaCTGACCCTGATCTTCGA

CCGgCACCCaATCGCaCACCTGCTGTGCTACCCgGCaGCaCGCTACCTGA

TGGGCtccATGACaCCaCAaGCCGTGCTGGCCTTCGTGGCCCTGATCCCa

CCaACaCTGCCCGGCACCAACATCGTGCTGGGCGCCCTGCCCGAGGACCG

CCACATCGACCGCCTGGCCAAGCGCCAGCGCCCCGGCGAGCGCCTGGACC

TGGCCATGCTGGCCGCCATCCGCCGCGTGTACGGCCTGCTGGCCAACACC

GTGCGCTACCTGCAGTGCGGCGGCAGCTGGCGCGAGGACTGGGGCCAGCT

GAGCGGCACCGCCGTGCCaCCaCAGGGCGCCGAGCCaCAGAGCAACGCCG

GaCCaCGaCCaCACATCGGCGACACCCTGTTCACCCTGTTCCGgGCaCCa

GAGCTGCTGGCaCCaAACGGCGACCTGTACAACGTGTTCGCCTGGGCCCT

GGACGTGCTGGCCAAGCGCCTGCGCtccATGCACGTGTTCATCCTGGACT

ACGACCAGtcaCCgGCCGGCTGCCGCGACGCCCTGCTGCAGCTGACCAGC

GGCATGGTGCAGACCCACGTGACaACaCCCGGCAGCATCCCaACaATCTG

CGACCTGGCCCGCACCTTCGCCCGCGAGATGGGCGAGGCCAACTAATAGG

GATCCCTCGAGAAGCTTgtca
NES = nuclear export sequence from MAP Kinase Kinase (MAPKK)
dmNLS = double mutated HSV-TK Nuclear Localization Sequence
CO = codon optimized
SC = splice donor/acceptor site corrected at 327 and 555,
Underlined sequence
```

In some embodiments, disclosed herein is a nucleic acid sequence encoding a thymidine kinase wherein at least one of the nucleotides corresponding to splice acceptor site nucleotides at positions 554 and 555, or at least one of the nucleotides corresponding to splice acceptor site nucleotides at positions 662 and 663, or at least one of the nucleotides corresponding to splice acceptor sites at positions 541 and 542 of the wild type sequence is replaced by another nucleotide. For example, position 541 may be mutated to an amino acid residue selected from: G to A. Position 542 may be mutated to an amino acid residue selected from: G to A. Position 554 may be mutated to an amino acid residue selected from: G to A. Position 555 may be mutated to an amino acid residue selected from: G to A. Position 662 may be mutated to an amino acid residue selected from: G to A. Position 663 may be mutated to an amino acid residue selected from: G to A.

A Kozak sequence flanks the AUG start codon within mRNA and influences the recognition of the start codon by eukaryotic ribosomes. In some embodiments, a polynucleotide sequence encoding HSV-TK comprises no more than one Kozak sequence. In some embodiments, the Kozak sequence is upstream of the coding portion of the DNA sequence. In some embodiments, the Kozak sequence of a polynucleotide encoding HSV-TK is modified to produce a Kozak sequence with a higher efficiency of translation initiation in a mammalian cell. In some embodiments, modification of the Kozak sequence does not produce an amino acid substitution in the encoded HSV-TK polypeptide product. In some embodiments, modification of the Kozak sequence results in at least one amino acid substitution in the encoded HSV-TK polypeptide product. In one embodiment, the modified HSV-TK has a polynucleotide sequence of SEQ ID NO: 18 or 22.

In some embodiments, the polynucleotide sequence encoding HSV-TK comprises at least 5, 10, 15, 20, 25, 30, 35, 40, 45, 50, 55, 60, 65, 60, 75, 80, 85, 90, 95, 100 or more codon substitutions. In some embodiments, the polynucleotide sequence encoding HSV-TK comprises at least 5, 10, 15, 20, 25, 30, 35, 40, 45, 50, 55, 60, 65, 60, 75, 80, 85, 90, 95, 100 or more codon substitutions, wherein the codon substitutions comprise the substitution of a codon having a higher frequency of usage in a mammalian cell than the wild type codon at that position. However, in some embodiments, less favored codons may be chosen for individual amino acids depending upon the particular situation.

In some embodiments, the polynucleotide sequence encoding HSV-TK comprising at least 5, 10, 15, 20, 25, 30, 35, 40, 45, 50, 55, 60, 65, 60, 75, 80, 85, 90, 95, 100 or more codon substitutions has less than about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID NO: 1 or 3 wherein the sequence identity is determined over the full length of the coding sequence using a global alignment method. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises at least 5, 10, 15, 20, 25, 30, 35, 40, 45, 50, 55, 60, 65, 60, 75, 80, 85, 90, 95, 100 or more codon substitutions, wherein the codon substitutions comprise the substitution of a codon having the highest frequency of usage in a mammalian cell for the wild type codon at that position. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises at least 5, 10, 15, 20, 25, 30, 35, 40, 45, 50, 55, 60, 65, 60, 75, 80, 85, 90, 95, 100 or more codon substitutions, wherein the substituted codons have a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises less than about 45, 40, 35, 30, 25, 20 or fewer codons, wherein the codons have a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises at least 78%, 79%, 80%, 81%, 82%, 83%, 84%, 85%, 86%, 87%, 88%, 89%, 90%, 91%, 92%, 93%, 94%, 95% or more of codons having a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, or higher. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises at least 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85% or more of codons having the highest frequency of usage in a mammalian cell. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises less than about 21%, 20%, 19%, 18%, 17%, 16%, 15%, 14%, 13%, 12%, 11%, 10% or less of codons having a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25. In some embodiments, the polynucleotide sequence comprises less than about 21%, 20%, 19%, 18%, 17%, 16%, 15%, 14%, 13%, 12%, 11%, 10% or less of codons having a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a mammalian cell. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises codon substitutions, wherein at least 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed as compared to the wild type sequence. In some embodiments, the polynucleotide sequence encoding HSV-TK comprises codon substitutions, wherein at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having a higher frequency of usage in a mammalian cell as compared to the wild type sequence. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

In some embodiments, the polynucleotide sequence encoding HSV-TK comprises codon substitutions, wherein at least 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having the highest frequency of usage in a mammalian cell as compared to the wild type sequence. In some embodiments, the corresponding encoded polypeptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a HSV-TK amino acid sequence, e.g., SEQ ID NO: 2 or 4.

The viral thymidine kinase gene from the selected herpesvirus may be readily isolated and mutated as described below, in order to construct nucleic acid molecules encoding a thymidine kinase enzyme comprising one or more mutations which increases biological activity of the thymidine kinase, as compared to unmutated wild-type thymidine kinase. The biological activity of a thymidine kinase may be readily determined utilizing any of the assays known in the art, including for example, determination of the rate of nucleoside analogue uptake or determination of the rate of nucleoside or nucleoside analogue phosphorylation. In addition, thymidine kinase mutants may be readily selected which are characterized by other biological properties, such as thermostability and protein stability.

In some embodiments, the polynucleotide sequence encoding HSV-TK is modified to remove or modify a predicted signal sequence. In some embodiments, the polynucleotide is modified to remove or modify a nuclear localization sequence (NLS). In some embodiments, the polynucleotide is modified to remove the nuclear localization sequence. In some embodiments, the polynucleotide is modified to modify the NLS so that if no longer functions to localize HSV-TK exclusively to the nucleus.

In some embodiments, a HSV-TK polypeptide sequence is mutated at amino acid residues 167, 168, or both. In one example, the sequence is mutated at amino acid residue 167. In another example, the sequence is mutated at amino acid residue 168. In another example, the sequence is mutated at amino acid residues 167 and 168. Amino acid residue 167 may be mutated to serine or phenylalanine. Amino acid residue 168 may be mutated to histidine, lysine, cysteine, serine or phenylalanine. In some embodiments, a HSV-TK polypeptide sequence is mutated at amino acid residues 25 and/or 26. In amino acid residues 25 and/or 26 may be mutated to an amino acid chosen from the group consisting of: glycine, serine, and glutamate. In some embodiments, the HSV-TK polypeptide sequence is mutated at amino acid residues 32 and/or 33. Amino acid residues 32 and/or 33 may be mutated to an amino acid chosen from the group consisting of: glycine, serine, and glutamate. In some embodiments, the HSV-TK polypeptide is mutated at amino acid residues 25, 26, 32, and/or 33. Amino acid residues 25, 26, 32, and/or 33, may be mutated to an amino acid chosen from the group consisting of: glycine, serine, and glutamate.

Amino acid residue modifications may be made in comparison to a polypeptide sequence of SEQ ID NOS: 2 or 4.

In accordance with the present invention, mutant thymidine kinase enzymes which are encoded by the above-described nucleic acid molecules are provided, as well as vectors which are capable of expressing such molecules. In some embodiments, expression vectors are provided comprising a promoter operably linked to a nucleic acid molecule of the present invention. In some embodiments, the vector is a viral vector capable of directing the expression of a nucleic acid molecule. Representative examples of such viral vectors include herpes simplex viral vectors, adenoviral vectors, adenovirus-associated viral vectors, pox vectors, parvoviral vectors, baculovirus vectors and retroviral vectors. In some embodiments, viral vectors are provided which are capable of directing the expression of a nucleic acid molecule which encodes a thymidine kinase enzyme comprising one or more mutations, at least one of the mutations encoding an amino acid substitution which increases a biological activity of thymidine kinase, as compared to unmutated (i.e., wild-type) thymidine kinase.

In some embodiments, a nucleic acid molecule provided herein encodes a thymidine kinase enzyme capable of phosphorylating a nucleoside analogue at a level at least 10% greater than the level of phosphorylation of the nucleoside analogue by a wild-type thymidine kinase enzyme. In some embodiments, the thymidine kinase enzyme is capable of phosphorylating a nucleoside analogue at a level at least 15%, at least 20%, at least 25%, at least 50%, at least 75%, at least 100%, at least 150%, at least 200%, at least 300%, or at least 500% greater than the level of phosphorylation of the nucleoside analogue by a wild-type thymidine kinase enzyme. Representative examples of suitable nucleoside analogues include gancyclovir, acyclovir, famciclovir, buciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5'-dideoxyuridine, idoxuridine, AZT, AIU, dideoxycytidine and AraC. In some embodiments, the improved TK mutant lacks thymidine kinase activity.

In some embodiments, the $K_m$ value thymidine kinase activity of a disclosed HSV-TK mutant is at least 2.5 μm. In some embodiments, the $K_m$ value of a disclosed HSV-TK mutant is at least 5 μm, at least 10 μm, at least 15 μm, at least 20 μm, at least 25 μm, at least 30 μm, at least 40 μm, at least 50 μm, at least 60 μm, at least 70 μm, at least 80 μm, at least 90 μm, at least 100 μm, at least 150 μm, at least 200 μm, at least 250 μm, at least 300 μm, at least 400 μm, at least 500 μm, at least 600 μm, at least 700 μm, at least 800 μm, at least 900 μm, or at least 1000 μm. In some embodiments, the percent $K_m$ of a disclosed HSV-TK mutant compared to wild-type HSV-TK is at least 15%, at least 20%, at least 25%, at least 50%, at least 75%, at least 100%, at least 150%, at least 200%, at least 300%, or at least 500%.

Within one embodiment of the present invention, truncated derivatives of HSV-TK mutants are provided. For example, site-directed mutagenesis may be readily performed in order to delete the N-terminal 45 amino acids of a thymidine kinase mutant, thereby constructing a truncated form of the mutant which retains its biological activity.

Mutations in nucleotide sequences constructed for expression of derivatives of thymidine kinase mutants should preserve the reading frame phase of the coding sequences. Furthermore, the mutations will preferably not create complementary regions that could hybridize to produce secondary mRNA structures, such as loops or hairpins, which would adversely affect translation of the receptor mRNA. Such derivatives may be readily constructed using a wide variety of techniques, including those discussed above.

In some embodiments, a HSV-TK polypeptide sequence is mutated at amino acid residues 167, 168, or both. In one example, the sequence is mutated at amino acid residue 167. In another example, the sequence is mutated at amino acid residue 168. In another example, the sequence is mutated at amino acid residues 167 and 168. Amino acid residue 167 may be mutated to serine or phenylalanine. Amino acid residue 168 may be mutated to histidine, lysine, cysteine, serine or phenylalanine. In some embodiments, a HSV-TK polypeptide sequence is mutated at amino acid residues 25 and/or 26. In amino acid residues 25 and/or 26 may be mutated to an amino acid chosen from the group consisting of: glycine, serine, and glutamate. In some embodiments, the HSV-TK polypeptide sequence is mutated at amino acid residues 32 and/or 33. Amino acid residues 32 and/or 33 may be mutated to an amino acid chosen from the group consisting of: glycine, serine, and glutamate. In some embodiments, the HSV-TK polypeptide is mutated at amino acid residues 25, 26, 32, and/or 33. Amino acid residues 25, 26, 32, and/or 33, may be mutated to an amino acid chosen from the group consisting of: glycine, serine, and glutamate. Amino acid residue modifications may be made in comparison to a polypeptide sequence of SEQ ID NOS: 2 or 4.

In accordance with the present invention, mutant thymidine kinase enzymes which are encoded by the above-described nucleic acid molecules are provided, as well as vectors which are capable of expressing such molecules. In some embodiments, expression vectors are provided comprising a promoter operably linked to a nucleic acid molecule of the present invention. In some embodiments, the vector is a viral vector capable of directing the expression of a nucleic acid molecule. Representative examples of such viral vectors include herpes simplex viral vectors, adenoviral vectors, adenovirus-associated viral vectors, pox vectors, parvoviral vectors, baculovirus vectors and retroviral vectors. In some embodiments, viral vectors are provided which are capable of directing the expression of a nucleic acid molecule which encodes a thymidine kinase enzyme comprising one or more mutations, at least one of the mutations encoding an amino acid substitution which increases a biological activity of thymidine kinase, as compared to unmutated (i.e., wild-type) thymidine kinase.

In some embodiments, a nucleic acid molecule provided herein encodes a thymidine kinase enzyme capable of phosphorylating a nucleoside analogue at a level at least 10% greater than the level of phosphorylation of the nucleoside analogue by a wild-type thymidine kinase enzyme. In some embodiments, the thymidine kinase enzyme is capable of phosphorylating a nucleoside analogue at a level at least 15%, at least 20%, at least 25%, at least 50%, at least 75%, at least 100%, at least 150%, at least 200%, at least 300%, or at least 500% greater than the level of phosphorylation of the nucleoside analogue by a wild-type thymidine kinase enzyme. Representative examples of suitable nucleoside analogues include gancyclovir, acyclovir, famciclovir, buciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5'-dideoxyuridine, idoxuridine, AZT, AIU, dideoxycytidine and AraC. In some embodiments, the improved TK mutant lacks thymidine kinase activity.

Within one embodiment of the present invention, truncated derivatives of thymidine kinase mutants are provided. For example, site-directed mutagenesis may be readily performed in order to delete the N-terminal 45 amino acids of a thymidine kinase mutant, thereby constructing a truncated form of the mutant which retains its biological activity.

Mutations in nucleotide sequences constructed for expression of derivatives of thymidine kinase mutants should preserve the reading frame phase of the coding sequences. Furthermore, the mutations will preferably not create complementary regions that could hybridize to produce secondary mRNA structures, such as loops or hairpins, which would adversely affect translation of the receptor mRNA. Such derivatives may be readily constructed using a wide variety of techniques, including those discussed above.

Using the methods described herein, the inventors determined that the majority of the candidates for optimized HSV-TK genes appeared to be compatible with a retroviral expression system and produce biologically useful retroviral titers.

Furthermore, the optimized HSV-TK genes which incorporated most of these optimizations (SEQ ID NO: 18) exhibited pro-drug GCV enzyme activity and selectivity for their ability to kill cancer cells following retroviral transduction delivery. The mutant HSV-TK gene A168H, which was codon optimized and splice corrected appeared to have the highest GCV mediated cancer kill activity (SEQ ID NOs: 12, 16, 18, or 22). The same version of this HSV-TK gene A168H and mutated at amino acids 159-161 from LIF to IFL exhibited GCV mediated cancer cell kill activity.

The mutant HSV-TK gene A167F (SEQ ID NOs: 13, 17, or 19), which was codon optimized and splice corrected had very high GCV mediated cancer kill activity following retroviral transduction delivery, but more surprisingly had NO thymidine kinase activity as determined by expressing this gene following retroviral transduction delivery in 3T3 TK(−) cells selected with HAT medium. To our knowledge, this is the most GCV selective HSV-TK synthetic gene product for GCV activation which has no Thymidine activity (HAT assay) ever evaluated biologically.

The double mutant HSV-TK gene A167F+A168H (SEQ ID NO: 14) unexpectedly ablates both GCV and Thymidine enzyme activity by exhibiting very little GCV mediated cancer kill activity and very little thymidine activity (HAT assay), The present inventors identified that it is possible to produce functional HSV-TK fusions of genes such as bacterial cytosine deaminase, yeast cytosine deaminase, neomycin phosphotransferase and include linker sequences and retain HSV-TK GCV mediated cancer cell killing activity.

In one embodiment, a codon optimized HSV-TK gene with GCV-mediated cancer killing activity may be made which retains one or more nuclear localization sequences which is not fused to one or more other therapeutic genes.

Additional modifications to and/or evaluations of an optimized HSV-TK gene described herein may include one or more of the following: removal of known nuclear localization sequences within HSV-TK; increased pro-drug GCV enzyme activity and selectivity for their ability to kill cancer cells, evaluate the use of more tags, fusion proteins and linkers of HSV-TK to other genes and proteins, co-expression of HSV-TK optimized genes with other optimized suicide and cancer killer genes in cancer cells, include optimized HSV-TK genes in a Reximmune-C type retroviral vector system; production and testing of a Reximmune-C type GMP product, or any combination thereof.

In one embodiment, a polynucleotide sequence described herein comprises a nuclear export signal. For example, a polynucleotide sequence may comprise TK168dmNES.

In another embodiment, a retroviral vector for use in the methods described herein comprises one or more splice site modifications.

In another embodiment, a retroviral vector for use in the methods described herein comprises HSV-TK A167Fsm (SEQ ID NO: 13).

In another embodiment, a retroviral vector for use in the methods described herein comprises HSV-TK A168Hsm (SEQ ID NO: 12).

In another embodiment, a retroviral vector for use in the methods described herein comprises HSV-TK A167Fdm (SEQ ID NO: 17).

In another embodiment, a retroviral vector for use in the methods described herein comprises HSV-TK A168dm (SEQ ID NO: 16).

In another embodiment, a retroviral vector for use in the methods described herein comprises HSV-TK A167Fdm and an NES (SEQ ID NO: 19).

In another embodiment, a retroviral vector for use in the methods described herein comprises HSV-TK A168Hdm and an NES (SEQ ID NO: 18). In such an embodiment, the sequence comprises HSV-TK A168H.

In another embodiment, a retroviral vector for use in the methods described herein comprises a HSV-TK, wherein such vector comprises an upgraded substrate binding domain and a mNLS/NES set.

In another embodiment, a retroviral vector for use in the methods described herein comprises a HSV-TK, wherein the vector comprises a selectable marker, a glowing gene and/or one or more kill genes.

In another embodiment, a retroviral vector for use in the methods described herein comprises at least two modifications.

Using the methods described herein, the inventors determined that the majority of the optimized HSV-TK genes appeared to be compatible with a retroviral expression system and produce biologically useful retroviral titers.

The mutant HSV-TK gene A167F (SEQ ID NOs: 13, 17, or 19), which was codon optimized and splice corrected had very high GCV mediated cancer kill activity following retroviral transduction delivery, but more surprisingly had no thymidine kinase activity as determined by expressing this gene following retroviral transduction delivery in 3T3 TK(−) cells selected with HAT medium. This is highly GCV selective HSV-TK synthetic gene.

The double mutant HSV-TK gene A167F+A168H (SEQ ID NO: 14) exhibited very little GCV mediated cancer kill activity and very little thymidine activity; thus, a proper double mutant may have surprising null properties.

The present inventors identified that it is possible to produce functional HSV-TK fusions of genes such as bacterial cytosine deaminase, yeast cytosine deaminase, neomycin phosphotransferase and include linker sequences and retain HSV-TK GCV mediated cancer cell killing activity.

In one embodiment, a fully codon optimized HSV-TK gene with GCV-mediated cancer killing activity may be made which retains one or more nuclear localization sequences which is not fused to one or more other therapeutic genes.

Additional modifications to and/or evaluations of an optimized HSV-TH gene described herein may include one or more of the following: removal of known nuclear localization sequences within HSV-TK; increased pro-drug GCV enzyme activity and selectivity for their ability to kill cancer cells, evaluate the use of more tags, fusion proteins and linkers of HSV-TK to other genes and proteins, co-expression of HSV-TK optimized genes with other optimized suicide and cancer killer genes in cancer cells, include optimized HSV-TK genes in a Reximmune-C retroviral vector system; production and testing of a Reximmune-C GMP product, or any combination thereof.

The therapeutic vectors may be administered alone or in conjunction with other therapeutic treatments or active agents. Examples of other active agents that may be used include, but are not limited to, chemotherapeutic agents, anti-inflammatory agents, protease inhibitors, such as HIV protease inhibitors, nucleoside analogs, such as AZT. In some embodiments, the methods of treatment further comprise administering to the subject a chemotherapeutic agent, a biologic agent, or radiotherapy prior to, contemporaneously with, or subsequent to the administration of the therapeutic viral particles. One of skill in the art will appreciate that the retroviral particles described herein may be administered either by the same route as the one or more agents (e.g., the retroviral vector and the agent are both administered intravenously) or by different routes (e.g., the retroviral vector is administered intravenously and the one or more agents are administered orally).

The dosage of the therapeutic viral particles lies preferably within a range of circulating concentrations that include the $ED_{50}$ with little or no toxicity. The dosage may vary within this range depending upon the dosage form employed and the route of administration utilized. A therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection or a half-maximal inhibition) as determined in cell culture. Such information can be used to more accurately determine useful doses in humans. Levels in plasma may be measured, for example, by RT-qPCR or ddPCR methods.

An effective amount or therapeutically effective of the retroviral particles disclosed herein to be administered to a subject in need of treatment may be determined in a variety of ways. By way of example, the amount may be based on viral titer or efficacy in an animal model. Alternatively the dosing regimes used in clinical trials may be used as general guidelines.

In some embodiments, the daily dose may be administered in a single dose or in portions at various hours of the day. In some embodiments, a higher dosage may be required and may be reduced over time when the optimal initial response is obtained. In some embodiments, treatment may be continuous for days, weeks, or years, or may be at intervals with intervening rest periods. In some embodiments, the dosage is modified in accordance with other treatments the individual may be receiving. However, the method of treatment is in no way limited to a particular concentration or range of the retroviral particle and may be varied for each individual being treated and for each derivative used.

Individualization of dosage may be required to achieve the maximum effect for a given individual. In some embodiments, the dosage administered to an individual being treated varies depending on the individual's age, severity or stage of the disease and response to the course of treatment. In some embodiments, clinical parameters for determining dosage include, but are not limited to, tumor size, alteration in the level of tumor markers used in clinical testing for particular malignancies. In some embodiments, the treating physician determines the therapeutically effective amount to be used for a given individual. In some embodiments, the therapies disclosed herein are administered as often as necessary and for the period of time judged necessary by the treating physician.

The therapeutic vectors, including but not limited to the therapeutic retroviral particles that are specifically to the cell or system of interest, may be systemically or regionally (locally) delivered to a subject in need of treatment. For example, the therapeutic vectors may be systemically administered intravenously. Alternatively, the therapeutic vectors may also be administered intra-arterially. The therapeutic vectors may also be administered topically, intravenously, intra-arterially, intra-tumorally, intracolonically, intratracheally, intraperitoneally, intranasally, intravascularly, intrathecally, intracranially, intramarrowly, intrapleurally, intradermally, subcutaneously, intramuscularly, intraocularly, intraosseously and/or intrasynovially or sterotactically. A combination of delivery modes may also be used, for example, a patient may receive the therapeutic vectors both systemically and regionally (locally) to improve tumor responses with treatment of the therapeutic vectors.

In some embodiments, multiple therapeutic courses (e.g., first and second therapeutic course) are administered to a subject in need of treatment. In some embodiments, the first and/or second therapeutic course is administered intravenously. In other embodiments, the first and/or second therapeutic course is administered via intra-arterial infusion, including but not limited to infusion through the hepatic artery, cerebral artery, coronary artery, pulmonary artery, iliac artery, celiac trunk, gastric artery, splenic artery, renal artery, gonadal artery, subclavian artery, vertebral artery, axillary artery, brachial artery, radial artery, ulnar artery, carotid artery, femoral artery, inferior mesenteric artery and/or superior mesenteric artery. Intra-arterial infusion may be accomplished using endovascular procedures, percutaneous procedures or open surgical approaches. In some embodiments, the first and second therapeutic course may be administered sequentially. In yet other embodiments, the first and second therapeutic course may be administered simultaneously. In still other embodiments, the optional third therapeutic course may be administered sequentially or simultaneously with the first and second therapeutic courses.

In some embodiments, the therapeutic vectors disclosed herein may be administered in conjunction with a sequential or concurrently administered therapeutic course(s) in high doses on a cumulative basis. For example, in some embodiments, a patient in need thereof may be systemically administered, e.g., intravenously administered, with a first therapeutic course of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis. The first therapeutic course may be systemically administered. Alternatively, the first therapeutic course may be administered in a localized manner, e.g., intra-arterially, for example a patient in need thereof may be administered via intra-arterial infusion with at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis.

In yet other embodiments, a subject in need thereof may receive a combination, either sequentially or concurrently, of systemic and intra-arterial infusions administration of high doses of delivery vector. For example, a patient in need thereof may be first systemically administered with at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis, followed by an additional therapeutic course of intra-arterial infusion, e.g., hepatic arterial infusion, administered delivery vector of at least of at least $1\times10^9$ TVP, at least $1\times10^{10}$ TVP, at least $1\times10^{11}$ TVP, at least $1\times10^{12}$ TV, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP on a cumulative basis. In still another embodiment, a patient in need thereof may receive a combination of intra-arterial infusion and systemic administration of delivery vector in high doses. For example, a patient in need thereof may be first administered via intra-arterial infusion with at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis, followed by an additional therapeutic course of systemically administered delivery vector of at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP on a cumulative basis. The therapeutic courses may also be administered simultaneously, i.e., a therapeutic course of high doses of delivery vector, for example, at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis, together with a therapeutic course of intra-arterial infusion, e.g., hepatic arterial infusion, administered delivery vector of at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP on a cumulative basis.

In still other embodiments, a subject in need thereof may additionally receive, either sequentially or concurrently with the first and second therapeutic courses, additional therapeutic courses (e.g., third therapeutic course, fourth therapeutic course, fifth therapeutic course) of cumulative dose of delivery vector, for example, at least of at least $1\times10^9$ TVP, at least $1\times10^{10}$ TVP, at least $1\times10^{11}$ TVP, at least $1\times10^{12}$ TVP, at least $1\times10^{13}$ TVP, at least $1\times10^{14}$ TVP, at least $1\times10^{15}$ TVP, at least $1\times10^{16}$ TVP, at least $1\times10^{17}$ TVP, at least $1\times10^{18}$ TVP, at least $1\times10^{19}$ TVP, at least $1\times10^{20}$ TVP, at least $1\times10^{21}$ TVP or at least $1\times10^{22}$ TVP delivery vector on a cumulative basis.

In some embodiments, the subject in need of treatment is administered systemically (e.g., intravenously) a dose of at least $1\times10^{11}$ TVP, followed by the administration via intra-arterial infusion (e.g., hepatic-arterial infusion) of a dose of at least $1\times10^{11}$ TVP. In other embodiments, the patient in need of treatment may be administered systemically (e.g., intravenously) a cumulative dose of at least $1\times10^{12}$ TVP, followed by the administration via intra-arterial infusion (e.g., hepatic-arterial infusion) of a dose of at least $1\times10^{12}$ TVP. In one embodiment, the patient in need of treatment may be administered systemically (e.g., intravenously) a dose of at least $1\times10^{13}$ TVP, followed by the administration via intra-arterial infusion (e.g., hepatic-arterial infusion) of a dose of at least $1\times10^{13}$ TVP. In yet other embodiments, the patient in need of treatment may be administered systemically (e.g., intravenously) a dose of at least $1\times10^{14}$ TVP, concurrently with the administration via intra-arterial infusion (e.g., hepatic-arterial infusion) of a dose of at least $1\times10^{14}$ TVP. In still other embodiments, the patient in need of treatment may be administered systemically (e.g., intravenously) a dose of at least $1\times10^{15}$ TVP, together with the administration via intra-arterial infusion (e.g., hepatic-arterial infusion) of a dose of at least $1\times10^{15}$ TVP. In yet other embodiments, the patient in need of treatment may be administered systemically (e.g., intravenously) a dose of at least $1\times10^{16}$ TVP, concurrently with the administration via intra-arterial infusion (e.g., hepatic-arterial infusion) of a dose of at least $1\times10^{16}$ TVP. In still other embodiments, the patient in need of treatment may be administered systemically (e.g., intravenously) a dose of at least $1\times10^{13}7$ TVP, together with the administration via intra-arterial infusion (e.g., hepatic-arterial infusion) of a dose of at least $1\times10^{17}$ TVP.

A subject in need of treatment may also be administered, either systemically or localized (for example intra-arterial infusion, such as hepatic arterial infusion) a therapeutic course of delivery vector for a defined period of time. In some embodiments, the period of time may be at least one day, at least two days, at least three days, at least four days, at least five days, at least six days, at least seven days, at least one week, at least two weeks, at least three weeks, at least four weeks, at least five weeks, at least six weeks, at least seven weeks, at least eight weeks, at least 2 months, at least three months, at least four months, at least five months, at least six months, at least seven months, at least eight months, at least nine months, at least ten months, at least eleven months, at least one year, at least two years, at least three years, at least four years, or at least five years. Administration could also take place in a chronic manner, i.e., for an undefined or indefinite period of time.

Administration of the therapeutic vector may also occur in a periodic manner, e.g., at least once a day, at least twice a day, at least three times a day, at least four times a day, at least five times a day. Periodic administration of the delivery vector may be dependent upon the time of delivery vector as well as the mode of administration. For example, parenteral administration may take place only once a day over an extended period of time, whereas oral administration of the delivery vector may take place more than once a day wherein administration of the delivery vector takes place over a shorter period of time.

In one embodiment, the subject is allowed to rest 1 to 2 days between the first therapeutic course and second therapeutic course. In some embodiments, the subject is allowed to rest 2 to 4 days between the first therapeutic course and second therapeutic course. In other embodiments, the subject is allowed to rest at least 2 days between the first and second therapeutic course. In yet other embodiments, the subject is allowed to rest at least 4 days between the first and second therapeutic course. In still other embodiments, the subject is allowed to rest at least 6 days between the first and second therapeutic course. In some embodiments, the subject is allowed to rest at least 1 week between the first and second therapeutic course. In yet other embodiments, the subject is allowed to rest at least 2 weeks between the first and second therapeutic course. In one embodiment, the subject is allowed to rest at least one month between the first and second therapeutic course. In some embodiments, the subject is allowed to rest at least 1-7 days between the second therapeutic course and the optional third therapeutic course. In yet other embodiments, the subject is allowed to rest at least 1-2 weeks between the second therapeutic course and the optional third therapeutic course.

Diagnosing a Patient that is Susceptible to Thymidine Kinase Gene Therapy Treatment Imaging tests, including the use of radioactive tracers, contrast imaging technology and other imaging technology can be used to identify patients that are susceptible to gene therapy treatment, including thymidine kinase gene therapy treatment, and thus more likely to benefit from such therapeutic measures.

In a preferred embodiment, positron emission tomography (PET) scans are used to identify patients capable of transducing retroviral vector particles containing thymidine kinase constructs for expression in vivo. A PET scan produces 3-dimensional images of functional processes in the body by detecting pairs of gamma rays emitted indirectly by radioactive tracers placed on a biological active molecule. PET scans detect energy emitted by positively charged particles (positrons).

Patients administered a retroviral vector particle containing thymidine kinase polynucleotide are co-administered a radiotracer agent capable of being cleaved by expressed thymidine kinase. An example is [$^{18}$F]FHBG (9-[4-[18F]fluoro-3-(hydroxymethyl)butyl]guanine), which is a high affinity substrate for HSV-TK enzyme, with relative low affinity for mammalian TK enzymes. See Yaghoubi and Gambhir, Nat. Protocol 1:3069-75 (2006); Green et al., J. Nucl. Med. 45:1560-70 (2004). [$^{18}$F]FHBG is phosphorylated by HSV1-TK or HSV1-sr39TK, which is then trapped within cells expressing thymidine kinase enzyme. Cleavage of this substrate in vivo in patients administered retroviral vectors containing a thymidine kinase polynucleotide, including the mutated and/or optimized thymidine kinase constructs described herein, thus indicates efficient transduction of the retroviral vector particles by the subjects and patients, and thus an initial of patient or subject susceptibility to thymidine kinase-mediated gene therapy.

Alternatively, other methods for measuring viral TK activity include chemical exchange saturation transfer magnetic resonance imaging with 5-methyl-5,6-dihydrothymidine and related compounds.

Accordingly, in some embodiments disclosed herein, provided are methods and compositions for detecting thymidine kinase expression in patients administered a retroviral viral particle containing a polynucleotide encoding a thymidine kinase protein. In some embodiments, the thymidine kinase is derived from Herpesviridae thymidine kinase. In some embodiments, the thymidine kinase is HSV-TK. In other embodiments, the thymidine kinase is HSV-TK1. In still other embodiments, the thymidine kinase is an optimized version of HSV-TK1.

In some embodiments, the HSV-TK gene is codon optimized for efficient expression and/or transduction. In other embodiments, the amino terminus of the thymidine kinase is altered to remove or eliminate the nuclear localization sequence (NLS) of the viral thymidine kinase sequence. In other embodiments, the thymidine kinase nucleotide sequence includes a nuclear export sequence (NES) attached to the amino terminus. In some embodiments, the nuclear export sequence is LQKKLEELELDG (SEQ ID NO: 24).

In yet other embodiments, the thymidine kinase coding sequence is mutated to increase substrate binding of the expressed thymidine kinase protein. In still other embodiments, the thymidine kinase coding sequence includes an A168H mutation.

Other examples of substrates targeted by thymidine kinase, including HSV-TK protein, include: FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-ganciclovir and penciclovir-like side chains. Examples of radiotracers that can be used to determine if a therapeutic protein, such as thymidine kinase, is expressed in an individual treated with the thymidine kinase gene therapy vectors described herein may also include $^{18}$F, $^{64}$Cu, $^{99m}$Te, $^{11}$C, $^{14}$C, $^{124}$I, $^{123}$I, $^{131}$I, $^{15}$O, $^{13}$N and/or $^{82}$RbCl.

Clinical trials for 9-[4-$^{18}$F-fluoro-3-(hydroxymethyl)butyl]guanine (FHBG) for PET can be found on the following website: www.clinicaltrials.gov. Methods of measuring FHBG with PET in clinical use can be found in clinical trials NCT00871702, NCT00185848 and NCT01082926.

Briefly patients will receive a dose of therapeutic drug product on Day 1. On Day 3 to 6, preferably day 4, or at a time period after receiving the dose of therapeutic drug product encoding a modified HSV-TK as disclosed herein, they will be infused with [$^{18}$F]FHBG intravenously and imaged by PET scan 1-5 hours later, preferably 0.5, 1.0, 1.5, 2, 2.5, 3.0, 3.5 or 4.0 hours later or other appropriate time after administration for scanning, for accumulation in the tumor sites where HSV-1 TK is shown to be expressed. Patients that show uptake of the FHBG will be enrolled in the trial; those that do not will be excluded as disclosed herein. The amount of FHBG will be determined and based on previous studies. Additional protocols for FHBG/PET may be found, for example, in references 15-39 below.

Accordingly provided herein is are methods and compositions for measuring a tagged substrate of thymidine kinase, including HSV-TK, including FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-ganciclovir and penciclovir-like side chains, the method comprising: a) transducing cells with a polynucleotide encoding HSV-TK; b) treating the cells with a substrate of HSV-TK attached to a radioactive tracer; and c) measuring the relative amount of radioactive signal present in target tissue. In one embodiment, step c) comprises measuring the output of the radioactive tracer in vivo in the subject using PET (positron emission tomography) scanning.

Also provided herein is are methods and compositions for identifying a patient or subject capable of benefiting from gene therapy treatment, comprising measuring a tagged substrate of thymidine kinase, including HSV-TK, including FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl- and 5-(3-hydroxypropyl)-substituted pyrimidine derivatives bearing 2,3-dihydroxypropyl, acyclovir-, ganciclovir- and penciclovir-like side chains. In some embodiments, the method comprises: a) administering a gene therapy retroviral particle comprising an HSV-TK polynucleotide and transducing cells with the polynucleotide encoding HSV-thymidine kinase; b) treating the cells with a substrate of HSV-TK attached to a radioactive tracer; c) measuring the relative amount of radioactive signal present in target tissue; and d) identifying patients where the level of radioactively-labelled HSV-TK substrate is above a set threshold. In one embodiment, step c) comprises measuring the output of the radioactive tracer in vivo in the subject using PET (positron emission tomography) scanning. In some embodiments, patients capable of benefiting from a gene therapy protocol include patients or subjects exhibiting a level above a set threshold on a PET scan. In some embodiments, the level of radioactive HSV-TK substrate is at least about 2.0 SUV or at least 20% above background on a PET scan. In some embodiments, the level of radioactive HSV-TK substrate is at least about 1.9 SUV or at least 20% above background on a PET scan. In yet other embodiments, the level of radioactive HSV-TK substrate is at least about 1.0 SUV, about 1.5 SUV, about 2.0 SUV or about 2.5 SUV or more, or at least 10% above background, at least 20% above background, at least 30% above background, at least 40% above background or at least 50% above background or more on a PET scan.

In some embodiments, provided herein are methods and compositions for identifying a patient or subject in need of treatment for benign or metastatic lesions and capable of benefiting from gene therapy treatment. In some embodiments, the method for identifying patients capable of benefiting from gene therapy for the treatment of benign or metastatic lesions include measuring a tagged substrate of thymidine kinase, including HSV-TK, including FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl- and 5-(3-hydroxypropyl)-substituted pyrimidine derivatives bearing 2,3-dihydroxypropyl, acyclovir-, ganciclovir- and penciclovir-like side chains after administration of the gene therapy treatment. In some embodiments, the method comprises: a) administering a gene therapy retroviral particle comprising an HSV-TK polynucleotide and transducing cells with the polynucleotide encoding HSV-thymidine kinase; b) treating the cells with a substrate of HSV-TK attached to a radioactive tracer; c) measuring the relative amount of radioactive signal present in target tissue; d) identifying patients where the level of radioactively-labelled HSV-TK substrate is above a set threshold; and e) treatment said patient or subject with the gene therapy retroviral particle. In one embodiment, step c) comprises measuring the output of the radioactive tracer in vivo in the subject using PET (positron emission tomography) scanning. In some embodiments, patients capable of benefiting from a gene therapy protocol include patients or subjects exhibiting a level above a set threshold on a PET scan. In some embodiments, the level of [$^{18}$F]FHBG signal is at least about 2.0 SUV or at least 20% above background on a PET scan. In some embodiments, the level of radioactive HSV-TK substrate is at least about 1.9 SUV or at least 20% above background on a PET scan. In yet other embodiments, the level of radioactive HSV-TK substrate is at least about 1.0 SUV, about 1.5 SUV, about 2.0 SUV or about 2.5 SUV or more, or at least 10% above background, at least 20% above background, at least 30% above background, at least 40% above background or at least 50% above background or more on a PET scan.

Also provided herein are methods comprising: (a) determining the level of [$^{18}$F]FHBG signal in a subject; and (b) selecting the subject for treatment with a composition wherein the level of FHBG is at least about 2.0 SUV or at least 20% above background on a PET scan. In some embodiments, the level of radioactive HSV-TK substrate is at least about 1.9 SUV or at least 20% above background on a PET scan. In yet other embodiments, the level of radioactive HSV-TK substrate is at least about 1.0 SUV, about 1.5 SUV, about 2.0 SUV or about 2.5 SUV or more, or at least 10% above background, at least 20% above background, at least 30% above background, at least 40% above background or at least 50% above background or more on a PET scan.

Additionally provided herein is a method comprising: (a) determining the level of [$^{18}$F]FHBG signal in a subject; (b) excluding the subject from treatment with a composition wherein the level of FHBG in the subject is greater than about 2.0 SUV or at least above 20% above background on a PET scan; and (c) administering to said subject an anti-cancer agent. In some embodiments, the level of radioactive HSV-TK substrate is at least about 1.9 SUV or at least 20% above background on a PET scan. In yet other embodiments, the level of radioactive HSV-TK substrate is at least about 1.0 SUV, about 1.5 SUV, about 2.0 SUV or about 2.5 SUV or more, or at least 10% above background, at least 20% above background, at least 30% above background, at least 40% above background or at least 50% above background or more on a PET scan.

In some embodiments, the invention provides a method for identifying a subject that is susceptible to a cancer treatment, the method comprising: a) identifying expression of [$^{18}$F]FHBG in the subject; b) treating the subject.

Also provided herein are compositions and methods of measuring HSV-TK-mediated FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-, ganciclovir- and penciclovir-like side chains phosphorylation using a fluorescent imaging system. In some embodiments, the method comprises: a) transducing cells with a polynucleotide encoding HSV-TK and a first fluorescent protein; b) transducing the cells with a polynucleotide encoding a second fluorescent or bioluminescent protein that is optically discernible from the first fluorescent or bioluminescent protein; c) treating the cells with an agent that becomes cytotoxic upon being phosphorylated by HSV-TK; and d) measuring the relative amount of expression of the first fluorescent protein and the second fluorescent protein. In one embodiment, step d) comprises a Perkin Elmer Plate reader, a fluorimeter; a fluorescent activated cell sorter (FACS); a cellometer; or a spectrophotometer. In another embodiment, step d) comprises measuring fluorescent output of the second fluorescent or bioluminescent protein in vivo in the subject using a fluorescent or bioluminescent imaging system.

Thymidine Kinase Diagnostic Uses

In some embodiments, disclosed herein is a method of selecting a patient for therapy, or for excluding a patient from therapy. In one embodiment, the thymidine kinase gene therapy. In other embodiments, the thymidine kinase is herpes simplex virus thymidine kinase (HSV-TK). In yet other embodiments, the thymidine kinase is HSV-TK1.

As described herein, [$^{18}$F]FHBG and other HSV-TK labeled substrates may be used as a marker for selection or exclusion of subjects for gene therapy. For example, cells expressing HSV-TK after administration of a retroviral vector particle comprising a polynucleotide encoding HSV-TK will selectively phosphorylate the nucleoside analogue 9-[4-fluoro-3-(hydroxymethyl)butyl]guanine ([$^{18}$F]FHBG). See, e.g., Yaghoubi and Gambhir, Nat. Protocols 1:3069-75 (2006). [$^{18}$F]FHBG imaging above a certain threshold can then be used to identify HSV-TK positive cells and to select or exclude a patient for gene therapy.

Accordingly, in one embodiment, a subject is administered a gene therapy composition, wherein the gene therapy composition encodes an HSV-TK polypeptide. The subject is administered a labeled nucleoside analog HSV-TK substrate after a predetermined period of time, and monitored until background of the labeled substrate is reached in the subject. The label activity is measured, and compared against a scan detecting lesions in the subject. If the imaging activity: 1) is above a set threshold; and 2) correlates with the lesion location in the subject, then the subject is a candidate for HSV-TK gene therapy.

In some embodiments, the nucleoside analog is FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-, ganciclovir- and penciclovir-like side chains. In some embodiments, the label is $^{18}$F, $^{64}$Cu, $^{99m}$Te, $^{11}$C, $^{14}$C, $^{124}$I, $^{123}$I, $^{131}$I, $^{15}$O, $^{13}$N and/or $^{82}$RbCl. Preferably, the labeled nucleoside analog HSV-TK substrate is [$^{18}$F]FHBG ((9-[4-$^{18}$F-fluoro-3-(hydroxymethyl)butyl]guanine).

Figure 2:
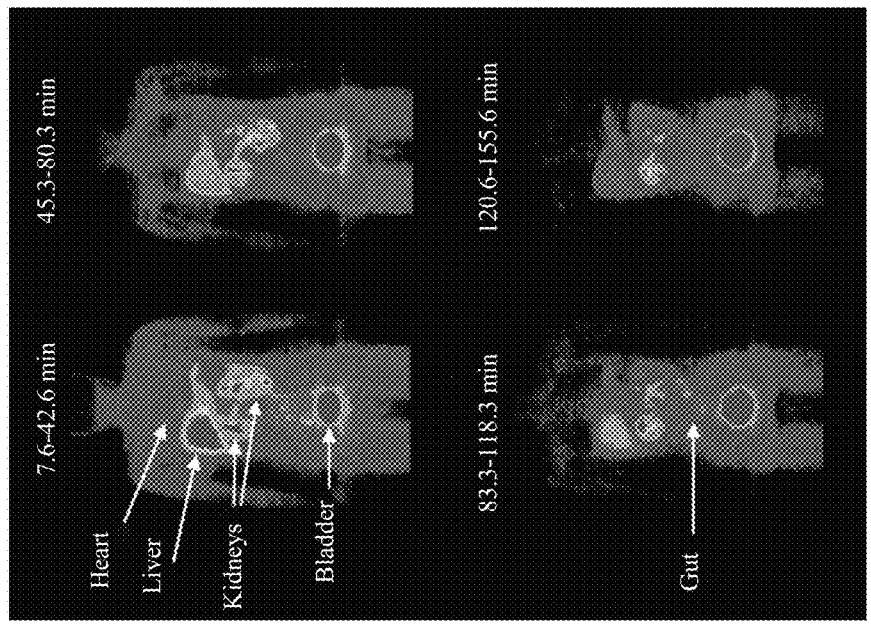
FIG. 2 is whole body coronal images of [$^{18}$F]FHBG biodistribution in a healthy human subject at four distinct time periods after 4.53 mCi i.v. injection of the [$^{18}$F]FHBG.

In some embodiments, the clearance pattern in a subject determines the length of time delay for measuring background and determining, for example, [$^{18}$F]FHBG imaging activity. In humans, for example, [$^{18}$F]FHBG background rapidly decreases from most tissues outside the lower abdomen, as seen in FIG. 2. As seen, between 7.6 and 42.6 minutes after administration of [$^{18}$F]FHBG, levels are high in the liver, kidneys and bladder. This is in contrast to the heart and lungs, for example, which show virtually no background [$^{18}$F]FHBG signal after administration. After 45.3 minutes to 80.3 minutes, [$^{18}$F]FHBG levels have decreased significantly in the liver and kidneys, with persistent high signal in the bladder. From 83.3 minutes to 155.6 minutes, levels in the liver and kidneys and decreased even further, with maintenance of high signal levels in the bladder. Accordingly, depending upon the organ and subject individual, some time may be required for background levels to decrease in order to measure HSV-TK gene expression. No time may be needed for measurement in organ systems outside of the lower abdomen region, as seen in the heart and lungs. In these organ systems, a sufficient threshold for gene therapy suitability may be, for example, at least above 1.0 SUV, at least above 1.5 SUV, at least above 2.0 SUV, at least above 2.5 SUV, at least above 3.0 SUV, at least above 3.5 SUV or at least above 4.0 SUV.

In contrast, some delay may be needed in order to image signals above background levels in, for example, the liver and kidneys. See Yaghoubi et al. Nat. Protocols at vol. 1, p. 3073. Because of the background signals in these organ systems, a sufficient threshold for determination of suitability for gene therapy treatment may be, for example, at least 10% above background, at least 15% above background, at least 20% above background, at least 25% above background, at least 30% above background, at least 35% above background, at least 40% above background, at least 45% above background, at least 50% above background, at least 55% above background, at least 60% above background, at least 65% above background, at least 70% above background, at least 75% above background, at least 80% above background, at least 85% above background, at least 90% above background, at least 95% above background or at least 100% or more above background when measured after a predetermined amount of time. For example, as seen in FIG. 2, background signals in the liver are considerably less after at least 1 to 1½ hours after administration of [$^{18}$F]FHBG. Accordingly, [$^{18}$F]FHBG signal measurements in the liver should not be taken until after [$^{18}$F]FHBG signal levels have decreased to background, approximately 1 to 1½ hours, depending upon clearance rate in each individual subject.

In some organ systems, HSV-TK gene expression may not be measurable, for example, in the bladder, where high background signal levels are maintained over time.

In other embodiments, a ratio of administered [$^{18}$F]FHBG to measured [$^{18}$F]FHBG signal is measured to determine if a subject should be included or excluded from a gene therapy protocol. For example, if a subject that is injected with, for example, 500 MBq of [$^{18}$F]FHBG and exceeds the threshold of, for example, 50 MBq of [$^{18}$F]FHBG signal, the subject is capable of producing a therapeutically effective amount of phosphorylated ganciclovir, or a derivative thereof, from a construct described herein to be therapeutic, indicating that the subject may respond in a gene therapy situation. In such an embodiment, the subject is a candidate for treatment with a gene therapy construct described herein.

In other embodiments, the subject is injected with 100-750 MBq or 100-600 MBq or 100-500 MBq or 200-500 MBq or 200-400 MBq, or 2.0 to 15.5 MBq/kg or 2.0 to 12.0 MBq/kg or 2.0 to 10.0 MBq/kg or 2.0 to 7.5 MBq/kg of [$^{18}$F]FHBG and exceeds the threshold of, for example, 10-100 MBq or 10-90 MBq or 10-80 MBq or 10-70 MBq or 10-60 MBq or 20-50 MBq or 20-40 MBq of [$^{18}$F]FHBG signal. In some embodiments, the subjected is injection with 200-500 MBq of [$^{18}$F]FHBG and exceeds the threshold of, for example, 20-50 MBq of [$^{18}$F]FHBG signal. In some embodiments, the ratio of [$^{18}$F]FHBG signal injected to [$^{18}$F]FHBG signal measured is 2:1, 5:1, 10:1, 20:1 30:1, 40:1 or 50:1. In some embodiments, the ratio of [$^{18}$F]FHBG signal injected to [$^{18}$F]FHBG signal measured is from about 2:1 to about 50:1, from about 2:1 to about 40:1, from about 5:1 to about 30:1, from about 5:1 to about 20:1, from about 5:1 to about 10:1 or about 10:1.

In another embodiment, if a subject produces sufficient phosphorylated FHBG to generate a signal of greater than 2.0 SUV or at least 20% above background on PET scan, the subject is likely to produce a therapeutically effective amount of TK from a construct described herein and the subject is likely respond in a gene therapy situation. In some embodiments, the subject may be selected for combination therapy with another anti-cancer agent or treatment described herein.

In other embodiments, the subject produces sufficient phosphorylated FHBG to generate a signal of greater than about 1.5 SUV, greater than about 2.0 SUV, greater than about 2.5 SUV, greater than about 3.0 SUV, greater than about 4.0 SUV or greater than about 5.0 SUV. In yet other embodiments, the subject generates a signal of at least 10% above background, at least 20% above background, at least 30% above background, at least 40% above background or at least 50% or more above background.

Cancers

Non-limiting examples of cancers can include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In other embodiments, the cancers to be treated are chosen from the group consisting of primary hepatocellular carcinoma, metastatic breast carcinoma to liver, metastatic pancreatic cancer to liver, metastatic gastric cancer to liver, metastatic esophageal cancer to liver, metastatic lung cancer to liver, metastatic melanoma to liver, metastatic ovarian carcinoma to liver and metastatic kidney cancer to liver.

Formulations

Pharmaceutical compositions comprising a therapeutic vector can be formulated in any conventional manner by mixing a selected amount of the therapeutic vector with one or more physiologically acceptable carriers or excipients. For example, the therapeutic vector may be suspended in a carrier such as PBS (phosphate buffered saline). The active compounds can be administered by any appropriate route, for example, orally, parenterally, intravenously, intradermally, subcutaneously, or topically, in liquid, semi-liquid or solid form and are formulated in a manner suitable for each route of administration.

In some embodiments, the therapeutic vector and physiologically acceptable salts and solvates are formulated for administration by inhalation or insufflation (either through the mouth or the nose) or for oral, buccal, parenteral or rectal administration. In some embodiments, for administration by inhalation, the therapeutic vector is delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In some embodiments, a pressurized aerosol dosage unit or a valve to deliver a metered amount. In some embodiments, capsules and cartridges (e.g., of gelatin) for use in an inhaler or insufflator are formulated containing a powder mix of a therapeutic compound and a suitable powder base such as lactose or starch.

In some embodiments, the pharmaceutical compositions are formulated for oral administration as tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). In some embodiments, the tablets are coated by methods well known in the art. In some embodiments, liquid preparations for oral administration are in the form of, for example, solutions, syrups or suspensions, or they are formulated as a dry product for constitution with water or other suitable vehicle before use. In some embodiments, such liquid preparations are prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). In some embodiments, the preparations also contain buffer salts, flavoring, coloring and sweetening agents as appropriate. In some embodiments, pharmaceutical compositions are formulated oral administration to give controlled release of the active compound. In some embodiments, the pharmaceutical compositions are formulated for buccal in the form of tablets or lozenges formulated in conventional manner.

In some embodiments, the therapeutic vector is formulated for parenteral administration by injection, e.g., by bolus injection, or continuous infusion. In some embodiments, formulations for injection are in unit dosage form, e.g., in ampoules or in multi-dose containers, with an added preservative. In some embodiments, the compositions are formulated as suspensions, solutions or emulsions in oily or aqueous vehicles. In some embodiments, the formulations comprise formulatory agents such as suspending, stabilizing and/or dispersing agents. Alternatively, in some embodiments, the active ingredient is in powder lyophilized form for constitution with a suitable vehicle, e.g., sterile pyrogen-free water, before use.

In some embodiments, the therapeutic vector is formulated as a depot preparation. In some embodiments, such long acting formulations are administered by implantation (for example, subcutaneously, intramuscularly or directly into or in close proximity to a tumor) or by intramuscular injection. Thus, for example, in some embodiments, the therapeutic compounds are formulated with suitable polymeric or hydrophobic materials (for example, as an emulsion in an acceptable oil) or ion exchange resins, or as sparingly soluble derivatives, for example, as a sparingly soluble salt.

In some embodiments, the active agents are formulated for local or topical application, such as for topical application to the skin and mucous membranes, such as in the eye, in the form of gels, creams, and lotions and for application to the eye or for intracisternal or intraspinal application. In some embodiments, such solutions, particularly those intended for ophthalmic use, are formulated as 0.01%-10% isotonic solutions, pH about 5-9, with appropriate salts. In some embodiments, the compounds are formulated as aerosols for topical application, such as by inhalation.

The concentration of active compound in the drug composition will depend on absorption, inactivation and excretion rates of the active compound, the dosage schedule, and amount administered as well as other factors known to those of skill in the art.

In some embodiments, the compositions are presented in a pack or dispenser device which comprise one or more unit dosage forms containing the active ingredient. In some embodiments, the pack may comprises metal or plastic foil, such as a blister pack. In some embodiments, the pack or dispenser device is accompanied by instructions for administration.

In some embodiments, the active agents are packaged as articles of manufacture containing packaging material, an agent provided herein, and a label that indicates the disorder for which the agent is provided.

Animal Models

In some embodiments, the retroviral vector particles, hereinabove described are administered to an animal in vivo as part of an animal model for the study of the effectiveness of a gene therapy treatment. In some embodiments, the retroviral vector particles are administered in varying doses to different animals of the same species. The animals then are evaluated for in vivo expression of the desired therapeutic or diagnostic agent. In some embodiments, from the data obtained from such evaluations, a person of ordinary skill in the art determines the amount of retroviral vector particles to be administered to a human patient.

Kits

Also provided are kits or drug delivery systems comprising the compositions for use in the methods described herein. All the essential materials and reagents required for administration of the retroviral particles disclosed herein may be assembled in a kit (e.g., packaging cell construct or cell line, cytokine expression vector). The components of the kit may be provided in a variety of formulations as described above. The one or more therapeutic retroviral particles may be formulated with one or more agents (e.g., a chemotherapeutic agent) into a single pharmaceutically acceptable composition or separate pharmaceutically acceptable compositions.

The components of these kits or drug delivery systems may also be provided in dried or lyophilized forms. When reagents or components are provided as a dried form, reconstitution generally is by the addition of a suitable solvent, which may also be provided in another container means.

Container means of the kits may generally include at least one vial, test tube, flask, bottle, syringe and/or other container means, into which the at least one substance can be placed.

The kits disclosed herein may also comprise instructions regarding the dosage and or administration information for the retroviral particle. Instructions can include instructions for practicing any of the methods described herein including treatment methods. Instructions can additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

In some embodiments, the kits or drug delivery systems include a means for containing the vials in close confinement for commercial sale such as, e.g., injection or blow-molded plastic containers into which the desired vials are retained. Irrespective of the number or type of containers, the kits may also comprise, or be packaged with, an instrument for assisting with the injection/administration or placement of the ultimate complex composition within the body of a subject. Such an instrument may be an applicator, inhalant, syringe, pipette, forceps, measured spoon, eye dropper or any such medically approved delivery vehicle.

Packages and kits can further include a label specifying, for example, a product description, mode of administration and/or indication of treatment. Packages provided herein can include any of the compositions as described herein. The package can further include a label for treating one or more diseases and/or conditions.

The term "packaging material" refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method described herein. A kit can include a compound in a pack, or dispenser together with instructions for administering the compound in a method described herein.

EXAMPLES

In order that those in the art may be better able to practice the compositions and methods described herein, the following examples are provided for illustration purposes.

Example 1: Clinical Trial

A dose escalation trial was conducted to evaluate the safety, pharmacokinetics, and pharmacodynamics of Reximmune-C2 (Thymidine Kinase and GM-CSF Genes) in refractory subjects with primary hepatocellular carcinoma or tumors metastatic to the liver.

Background and Rationale

Reximmune-C2 is comprised of a genetic delivery platform containing an internal payload that encodes for therapeutic proteins of interest. The genetic delivery platform has been dosed in over 280 subjects worldwide; approximately 270 subjects were treated with the vector containing dnG1 as a payload (Rexin-G) and 16 subjects with thymidine kinase (vTK) and the immune stimulator Granulocyte Macrophage Colony Stimulating Factor (GM-CSF) as a payload (Reximmune-C). The genetic delivery platform is a highly engineered non-recombinant Mouse Moloney Viral vector (MoMLV). Previously, a Phase 1 dose escalation trial was performed investigating the combination of Rexin-G and Reximmune-C in subjects with refractory primary or metastatic solid tumors (Genevieve Trial). This proposed Phase I clinical trial (entitled Genevieve 2 Trial) is an extension of a trial undertaken investigating Reximmune-C2 alone—without the Rexin-G—utilizing an improved form of thymidine kinase in a thymidine kinase plus GM-CSF combination.

In the original Genevieve trial, sixteen subject were recruited over 3 dose levels with the mean exposure in the highest dose group being $8.0 \times 10^{10}$ cfus (# of pts=7) and the longest duration 6 cycles (range of cycles 3-6). For Part A of the study, treatment consisted of a previously determined safe and effective (optimal) dose of Rexin-G, and escalating doses of Reximmune-C. Specifically, Rexin-G, $2 \times 10^{11}$ cfu, on Days 1, 3, 5, 8, 10 and 12, Reximmune-C, 1.0, 2.0 or $3.0 \times 10^{10}$ cfu on Day 3 (Dose Levels I, II, III respectively), and valacyclovir at 1 gm p.o. three times a day on Days 6-19, as one cycle. For the Part B part of the study, subjects who had no toxicity or in whom toxicity had resolved to Grade 1 or less could receive additional cycles of therapy up to a total of 6 treatment cycles.

There were no dose-limiting toxicities at any dose level. Unrelated adverse events were reported for the 16 subjects in the study, but the number of events was low (in most cases 1 or 2 occurrences per preferred term), and most were Grade 1 or 2. Related non-serious adverse events occurred in 2 subjects and both were Grade 2. Four subjects experienced serious adverse events, all of which were deemed not related to the study drug.

The rationale for continuation of this Phase 1 trial is that: (1) thymidine kinase itself could prove to be an effective anticancer agent particularly in subjects whose tumors demonstrate a bystander effect; (2) administration of the genetic delivery platform to date to an international group of subjects has demonstrated a very high degree of safety; and (3) biodistribution in animals suggests a high biodistribution to the liver. Moreover, the addition of GM-CSF could contribute to an immunological effect and enhanced tumor cell kill through tumor associated antigens through recruitment of the appropriate immune cells.

The biodistribution of the viral particles is highest to the liver, followed by spleen, then lung—this is the rationale for focusing initially on hepatocellular tumors where the dose intensity should be the highest. There is also a high clinical unmet need for effective anticancer agents for these cancers.

It is understood that the embodiments disclosed herein are not limited to the particular methods and components and other processes described as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Example 2: TK Diagnostic Assay for Gene Therapy Applications

Animal and human studies have previously shown the utility of measuring vTK expression by PET imaging using [$^{18}$F]-FHBG. These imaging tools will be utilized as a personalized surrogate test in accessing appropriate dosing and exposure and used in the IB portion to determine which subjects have the best opportunity to benefit from the drug candidates.

Figure 3:
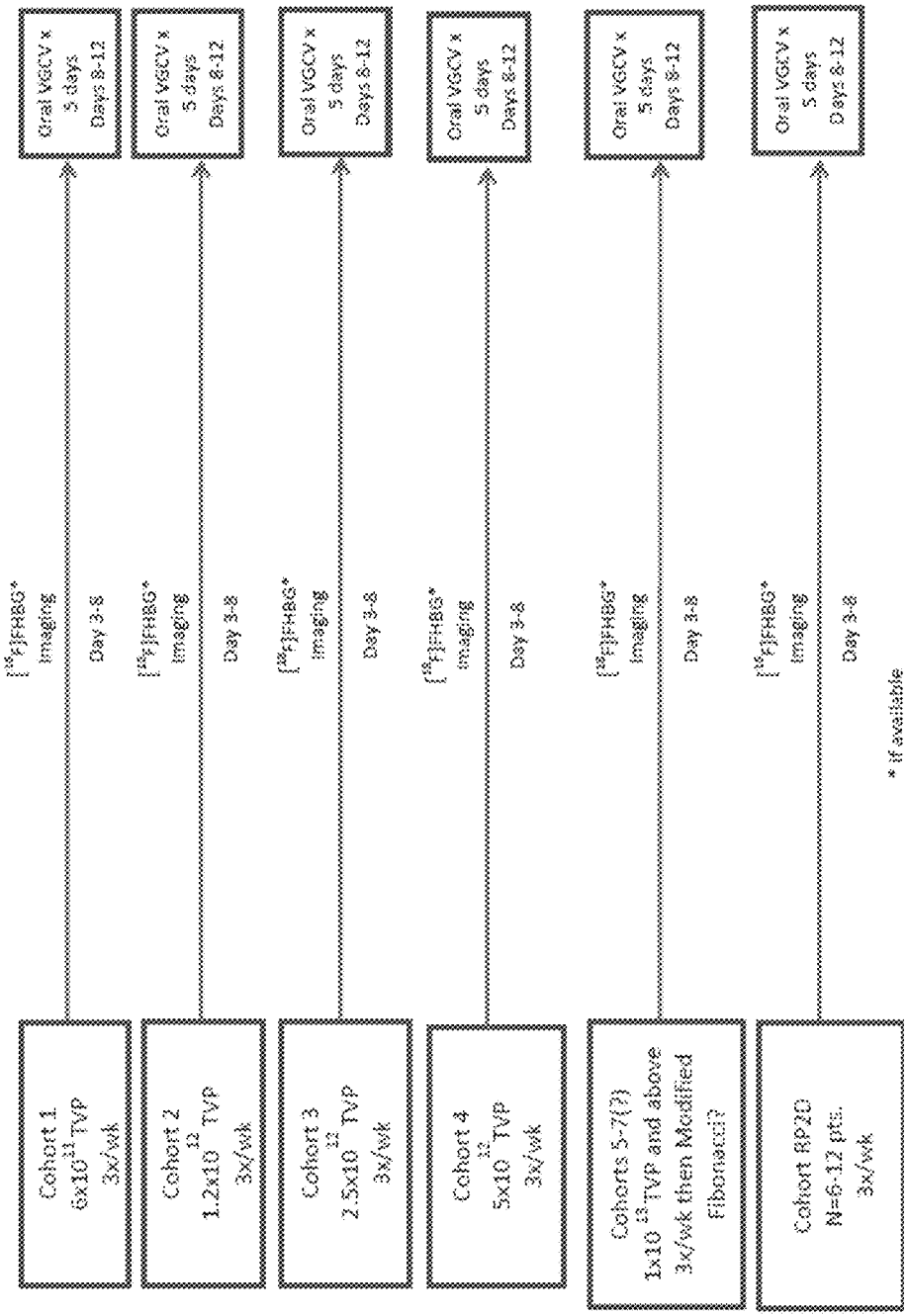
FIG. 3 is a schematic for a Phase IA clinical trial.
Figure 4:
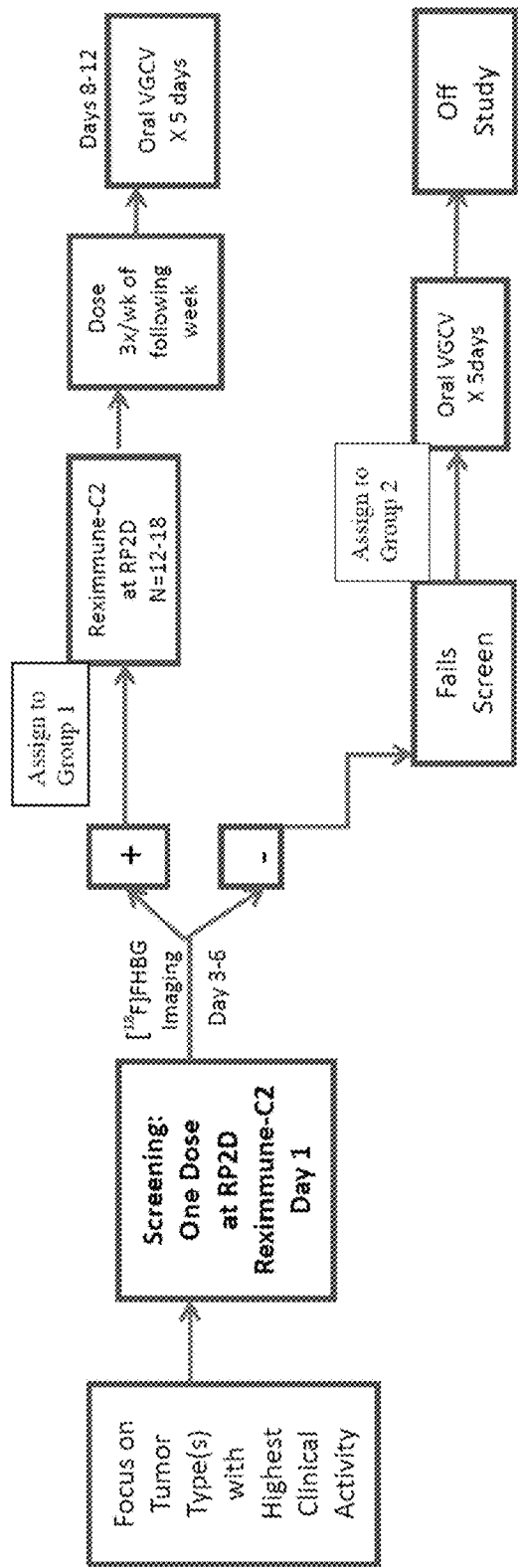
FIG. 4 is a schematic for a Phase IB clinical trial.
Figure 5:
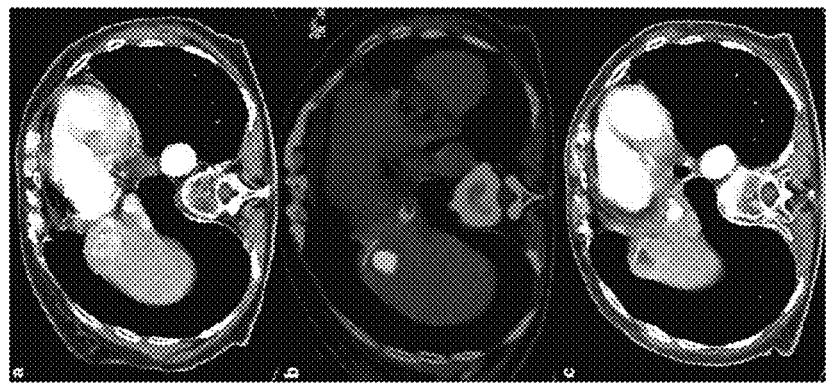
FIG. 5 is a patient's response to treatment with HSV-TK in AAV retroviral vector particle.
Figure 6:
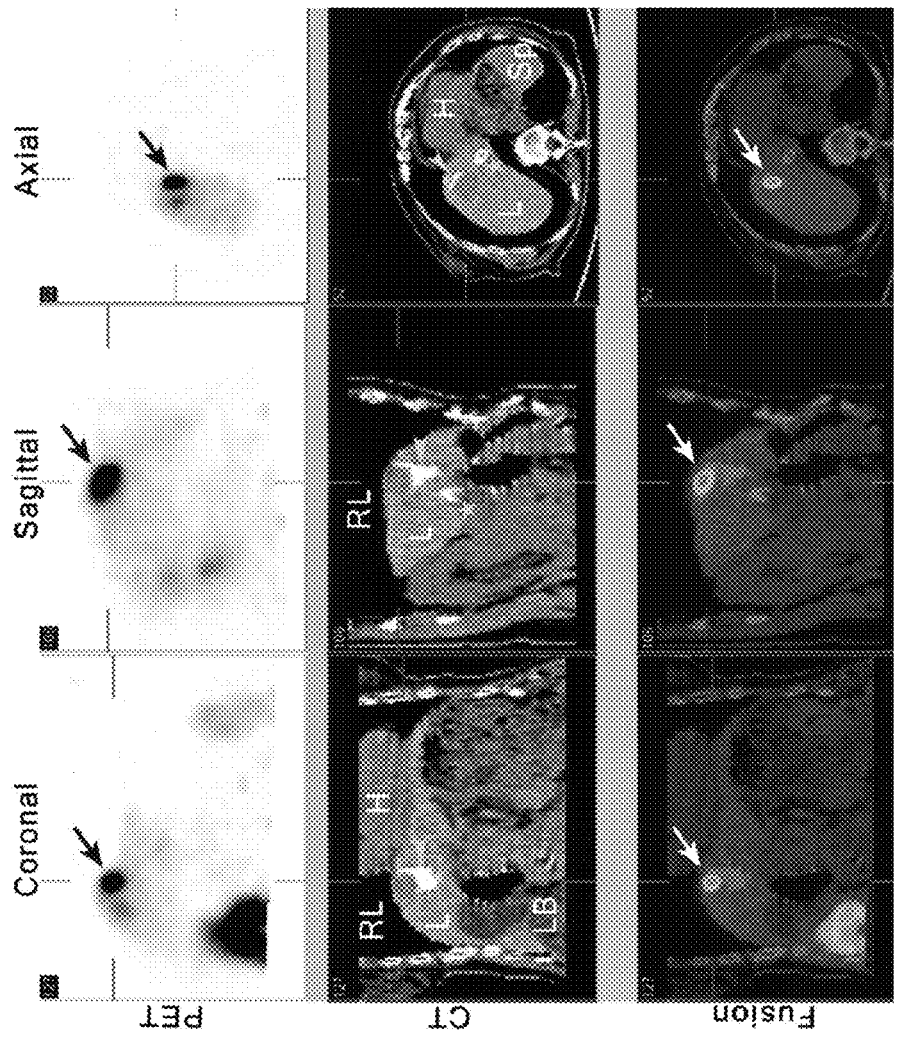
FIG. 6 measuring the response of a patient to administration of [$^{18}$F]FHBG in PET Scan (top panel), CT Scan (middle panel) and fusion of signals (bottom panel).
Figure 7:
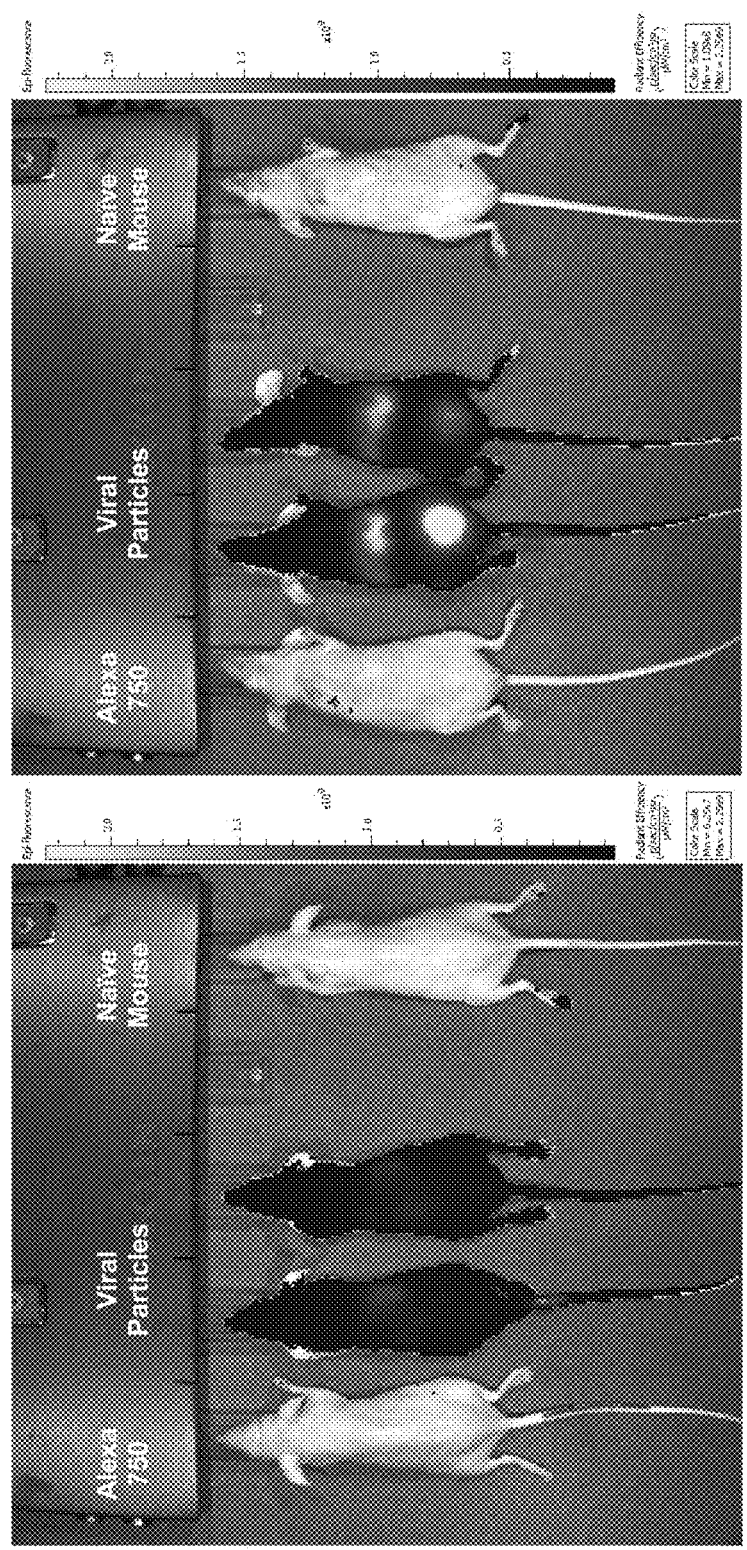
FIG. 7 is a fluorescent image of the biodistribution of the HSV-TK retroviral vector particles in animals.
Figure 8:
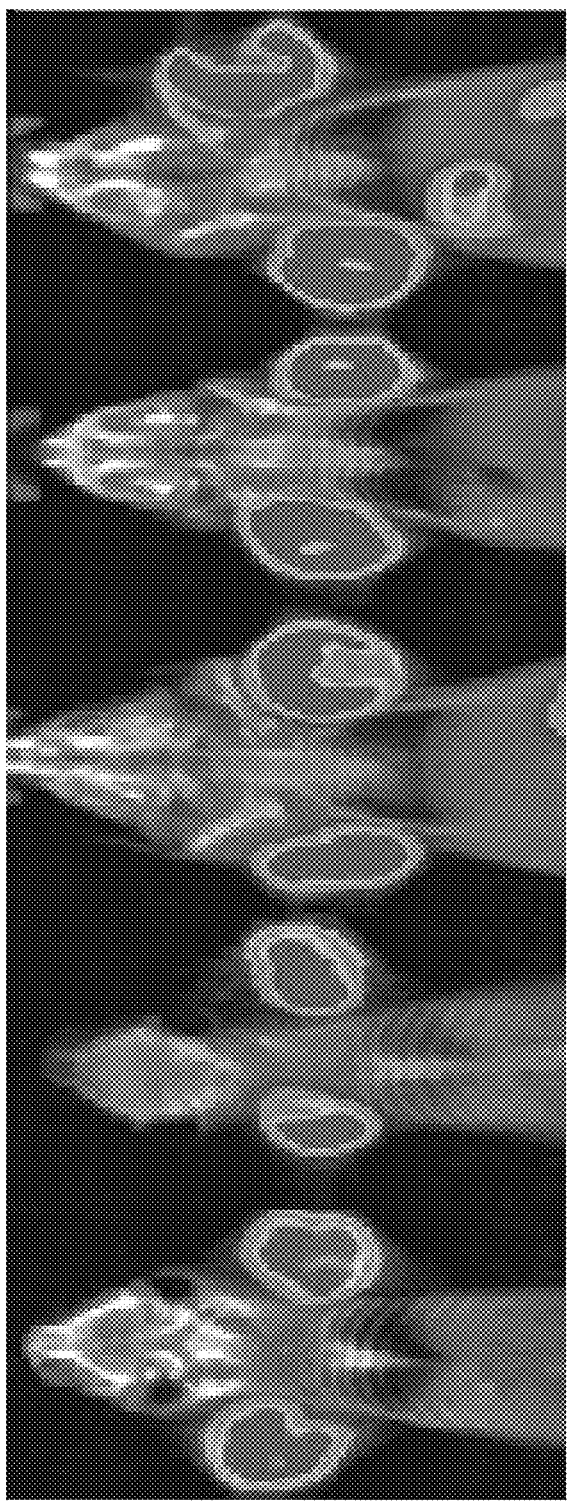
FIG. 8 is a comparison of coronal three hour images of 5 mm slices in rats administered Reximmune C1 and C2. The tumor on the left expressed Reximmune-C2 and on the right is Reximmune-C1.
Figure 9:
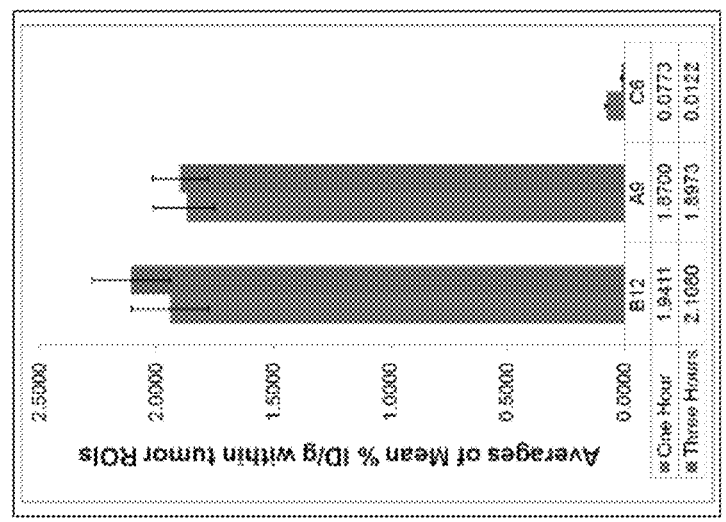
FIG. 9 is a graphical representation of FIG. 8, showing the averages of the mean within tumors for one and three hour images. Error bars are standard error of the averages. B12 is the Reximmune-C2 expressing tumor and A9 the Reximmune-C1 expressing tumor. C6 is the native cell line tumor.

This clinical trial is divided into two phases: Phase IA in which Reximmune-C2 was administered as a single intravenous dose on three out of five days and the presence of the HSV-TK-m2 expression potentially monitored by [$^{18}$F]FHBG PET scanning after 3-8 days (Schematic for Phase IA is illustrated in FIG. 3). Valganciclovir (the oral form of ganciclovir) dosing is initiated on day 8 for 5 days irrespective of the PET scan results. An approximately one week drug holiday follows. Each cycle will be of three weeks duration.

There will be three patients in the first and subsequent cohorts until a patient experiences Dose Limiting Toxicity (DLT) or two instances of NCI-CTC Grade 2 toxicities attributed to the study drug (except nausea/vomiting, fatigue, anorexia, alopecia, or anemia). If there are no DLTs, patients will move to the next dose level. If there is a DLT, the cohort will be expanded to 6 patients and the dose level will not be exceeded if 2 or more patients exhibit DLTs.

Once the Maximum Administered Dose (MAD) is reached, a modified Fibonacci schedule will be followed starting with the cohort dose which had no DLTs and continuing until dose-limiting toxicities are observed in two patients at a dose level. Once the Recommended Phase 2 Dose (RP2D) is defined, 6-12 patients will be recruited.

Phase IB is designed to explore the activity of Reximmune-C2 in patients of a defined tumor type and stage based on the Phase IA data and who are [$^{18}$F]FHBG scan positive day three to six after one dose (RP2D) of Reximmune-C2. If the scan is positive, the patient is accepted into the Phase IB treatment phase of the protocol and the RP2D is given as three doses within 5 days, followed by 5 days of valganciclovir beginning on day 8 of that phase, followed by a one week drug holiday. Each cycle is of three week duration. Patients who have a negative [$^{18}$F]FHBG PET scan after one single dose of Reximmune-C2 will be dosed with 5 days of valganciclovir and will not continue in the study.

The patient DLT will be defined as the occurrence of any of the following events which is attributed to Reximmune-C2 and occurring during the first cycle (3 weeks) of drug administration:

Grade 4 neutropenia (i.e., absolute neutrophil count (ANC)<500 cells/mm$^3$) for 7 or more consecutive days or febrile neutropenia (i.e., fever ≥38.5° C. with an ANC<1000 cells/mm$^3$); Grade 4 thrombocytopenia (<25,000 cells/mm$^3$ or bleeding episode requiring platelet transfusion); Grade 3 or greater nausea and/or vomiting despite the use of adequate/maximal medical intervention and/or prophylaxis; Any Grade 3 or greater non-hematological toxicity (except Grade 3 injection site reaction, alopecia, fatigue); Retreatment delay of more than 3 weeks due to delayed recovery from a toxicity related to treatment with Reximmune-C2; and Grade 3 or greater hypersensitivity reaction despite the appropriate use of premedications (by Common Toxicity Criteria defined as "symptomatic bronchospasm, requiring parenteral medications(s), with or without urticaria; allergy-related edema-angioedema").

Reximmune-C2 is infused intravenously over 15-60 minutes (depending on the dose) via an infusion pump. Reximmune-C2 is provided in 30 ml vials stored at −80° C.±10° C.

In this Phase I trial, the safety, pharmacokinetics, and pharmacodynamics of escalating doses of Reximmune-C2 will be investigated. The maximum tolerated dose will be identified and a recommended Phase 2 dose will be defined for Reximmune C2. Any antitumor activity and clinical responses to Reximmune-C2 treatment will be described.

The starting dose in this trial is based on: human clinical safety experience with the related vector platform drug products Rexin-G and Reximmune-C and the results of the 21 day rat GLP toxicology study for Reximmune-C2.

Objectives

The primary objective of the study is to determine the maximum tolerated dose (MTD), dose limiting toxicity (DLT), safety, and a recommended Phase 2 dose (RP2D) of Reximmune-C2 administered over a three week cycle consisting of a series of three doses given intravenously within five days in week 1, followed by 5 daily doses of valganciclovir in week 2 in patients enrolled in this study who have been diagnosed with advanced primary or metastatic tumors to the liver.

Secondary objectives include: (i) evaluation of the plasma pharmacokinetics of Reximmune-C2; (ii) assessment of the surrogate of HSV-TK-m2 protein expression from Reximmune-C2 via serial [$^{18}$F]FHBG PET and/or SPECT imaging; (iii) description and assessment of any preliminary evidence of anti-tumor activity of Reximmune-C2; and (iv) to provide clinical research testing for antibodies to retrovector gp70 env, replication-competent retrovirus in peripheral blood lymphocytes (PBLs); vector integration into genomic DNA of PBLs, and circulating hGM-CSF protein.

Methods

Study Design: Parallel group, open label dose escalation, three-center clinical trial.

Stratification: None.

Therapy: Reximmune-C2 will be administered as an intravenous infusion to separate patients. In Phase IA—investigating Reximmune-C2—the dose will be escalated among cohorts of patients until DLT is observed. At the RP2D, additional patients will be recruited. In Phase IB patients will be pre-screened by [$^{18}$F]FHBG PET for expression of the HSV-TK-m2. Those that express HSV-TK-m2 will receive additional doses of Reximmune-C2. Patients will not be pre-medicated unless hypersensitivity reactions occur.

Statistical Methods: Descriptive statistics will be used for statistical analysis.

Sample Size Determination: Precise sample size cannot be defined, as it is dependent on the observed toxicity. For each schedule, cohorts of three to six subjects will be treated at each dose level until the MTD is defined. Once the MTD is identified, this dose level will be expanded to a maximum of 12 patients who will be treated to better define the tolerability and pharmacokinetics of the dose and schedule. It is expected that 45-70 subjects will be enrolled, with 33 to 46 in the IA portion.

Enrollment Criteria

Subjects must meet all of the following inclusion criteria to be eligible for randomization into the study:

1. Diagnosis of histologically documented, advanced stage, primary or metastatic adult solid tumors in the liver that are refractory to standard therapy or for which no curative standard therapy exists.
2. Evidence of radiographically measurable or evaluable disease.
3. All acute toxic effects of any prior radiotherapy, chemotherapy, or surgical procedures must have resolved to National Cancer Institute (NCI) Common Toxicity Criteria (CTC) (Version 4.0) Grade <1.
4. Age must be >18 years.
5. Last dose of antineoplastic therapy except for hormonal therapy must be >21 days. External beam radiotherapy must have been <25% bone marrow-containing skeleton.
6. Patients may be Hepatitis B and C positive. (Patients may continue their antiviral medications).
7. Patients may have intracranial metastases of any number if they have been brain irradiated and stable for 6 weeks. Patients may be taking anti-seizure medicines but must not be on steroids.
8. Karnofsky performance status must be ≥70.
9. Life expectancy of at least 3 months.
10. Patients must be able to travel to St. Luke's Medical Center for the PET scans.
11. Required baseline laboratory data include:

| | |
|---|---|
| Absolute neutrophil count (ANC) | ≥1,500/mm³ [SI units 10⁹/L] |
| Platelets | ≥75,000/mm³ [SI units 10⁹/L] |
| Hemoglobin | ≥8.0 gm/dL [SI units mmol/L] |
| Serum Creatinine | ≤1.5 × laboratory upper limit of normal (L-ULN) |
| Bilirubin | ≤2.0 mg/dL |
| Alkaline phosphatase | ≤5 × L-ULN |
| AST, ALT | ≤5 × L-ULN |
| LDH | ≤5 × L-ULN |
| Pregnancy test (females of childbearing potential) | Negative within 7 days of starting Protocol |

12. Signed informed consent indicating that they are aware of the neoplastic nature of their disease and have been informed of the procedures to be followed, the experimental nature of the therapy, alternatives, potential benefits, side effects, risks, and discomforts.
13. Willing and able to comply with scheduled visits, treatment plan, and laboratory tests.

The presence of any of the following will exclude a subject from study enrollment 1. Concurrent therapy with any anticancer therapy including any other investigational agent.
2. Known intracranial edema or a CVA within 6 weeks of screening.
3. Pregnant or breast-feeding women. Female subjects must agree to use effective contraception, must be surgically sterile, or must be postmenopausal. Male subjects must agree to use effective contraception or be surgically sterile. The definition of effective contraception will be based on the judgment of the Investigator or a designated associate. All at-risk female subjects must have a negative pregnancy test within 7 days prior to the start of study treatment.
4. Clinically significant cardiac disease (New York Heart Association, Class III or IV).
5. Dementia or altered mental status that would prohibit informed consent.
6. Other severe, acute, or chronic medical or psychiatric condition or laboratory abnormality that may increase the risk associated with study participation or study drug administration or may interfere with the interpretation of study results and, in the judgment of the Principal Investigator, would make the subject inappropriate for this study.
7. Known side effects to antivirals in the ganciclovir class.
8. Patients who are known to be HIV positive.
9. Patient must not be taking steroids at the time of screening.

Rationale for the Starting Dose and Schedule

Reximmune-C has been dosed in 16 patients over a range of 1.0, 2.0 or $3.0 \times 10^{10}$ cfu (Dose Levels I, II, III respectively on day 3 of the cycle). There were no dose-limiting toxicities at any dose level. Unrelated adverse events were reported for the 16 patients in the study, but the number of events was low (in most cases 1 or 2 occurrences per preferred term), and most were Grade 1 or 2. Related nonserious adverse events occurred in 2 patients and both were Grade 2. Four patients experienced serious adverse events, all of which were deemed not related to the study drug. The trial was closed prior to determining the optimal dose and schedule of Reximmune-C. In this trial, the new Genevieve-2 Trial, initial dosing will be based on the 21 day toxicology and the HSV-TK-m1 study. Future dosing will proceed using total viral particles (TVP) which is a more accurate measure of titer than cfu per mL.

The schedule is based on the rationale that Reximmune-C2 exposure will not transduce all of the tumor cells. Therefore, patients will be dosed three times in a cycle over a period of 5 days.

The time between exposure to GDS and the expression of HSV-TK-m2 (and hGM-CSF) is estimated to be 48 to 72 hours. Therefore, 72 hours after the third dose of Reximmune-C2, valganciclovir will be initiated. The dose (which will be adjusted for renal function) will be given at conventional antiviral dose levels. Due to the potential toxicity of valganciclovir and the published observations that 5 days of ganciclovir should be sufficient to kill the majority of cells containing HSV-TK-m2, 5 days of therapy was chosen. Due to the potential toxicity of both Reximmune-C2 and valganciclovir, this will be followed by an approximately 9 day drug holiday. The hGM-CSF may be at sufficient concentrations at the time of valganciclovir addition to influence the presentation of any tumor associated antigens (TAAs) that may appear during tumor cell apoptosis.

Plasma samples will be taken after the first and third doses in Cycle One and after the first dose in Cycle Two for pharmacokinetics.

As distribution is primarily to the liver, toxicities will be carefully monitored there and because of the implications, the bone marrow.

This clinical protocol calls for the administration of Reximmune-C2 via intravenous infusion to patients with advanced malignancies, either primary hepatocellular or tumors metastatic to the liver. There will be two parts: Phase IA (dose escalation 3 doses/week every three weeks) and Phase IB (pre-screening after one dose of Reximmune-C2 and an [$^{18}$F]FHBG scan). If the PET scan is positive, the patient will continue on study. If the PET scan is negative, the patient will receive 5 days of valganciclovir and will not continue in the trial. For Phase IA, dose escalation will follow an accelerated titration design, incorporating three patients per dose level until either one instance of DLT or two instances of NCI-CTC Grade 2 toxicities attributed to the study drug (except nausea/vomiting, fatigue, anorexia, alopecia or anemia) are observed. Thereafter, dosing in the clinical protocol will follow a modified Fibonacci schedule until dose-limiting toxicities are achieved.

Trial Design

This is a Phase 1, open-label, four center, dose-escalating trial. The dose will be increased until DLT is observed, and the MTD is defined.

Reximmune-C2 will be administered as an IV infusion over 15-60 minutes. It is anticipated that 33-70 patients will be treated during the course of the study.

For Phase IA, the dose of Reximmune-C2 will be escalated from $6.0 \times 10^{11}$ TVP. In the accelerated dose escalation phase, cohorts of three patients will be enrolled at each dose level. The dose escalation increment will be 100% until a DLT or two CTC Grade 2 or greater toxicities are observed. When the accelerated dose escalation ends, the dose escalation for a new patient in the standard dose escalation will follow a modified Fibonacci scheme (i.e., dose increments of 67%, 50%, 40%, 33% and 25%). A minimum of three patients per dose level will be enrolled. For Phase IB, the dose of Reximmune-C2 will be the RP2D. DLT will be assessed. If a DLT is observed in ≥2 out of six patients at a dose level, there will be no further dose escalation; this dose level will define the maximum administered dose (MAD).

The dose just below the MAD will be considered the MTD. Once the MTD is defined, this dose level can be expanded to a maximum of twelve patients to further characterize the pharmacokinetic and pharmacodynamic parameters and suitability as a recommended dose for Phase 2 clinical studies.

Treatment of Patients

Only qualified personnel who are familiar with procedures that minimize undue exposure to themselves and to the environment should undertake the preparation, handling, and safe disposal of biotherapeutic agents in an appropriate environment.

Reximmune C2 is a Moloney Murine replication incompetent retrovector particle containing the genes encoding for a HSV-TK-m2 and hGM-CSF. The drug product contains DMEM (low glucose), RD-Retrovector Particles, L-glutamine, Sodium pyruvate, human serum albumin, n-butyric acid, Pulmozyme®, magnesium and other excipients.

Drug product is available in one vial size: 30 mL type 1 clear glass vials with a 20 mm finish (containing 25 mL of $\geq 1.0 \times 10^{10}$ TVP). The vials are closed with 20 mm Teflon coated serum stoppers and 20 mm flip-off lacquered flip tops.

Reximmune-C2 will be administered intravenously by infusion pump over 15 minutes up to a volume of 100 mL, from >100 mL to 200 mL over 30 minutes, from >200 mL to 300 mL over 45 minutes, and from >300 mL to 400 mL over 60 minutes. Volumes over 400 mL will be administered at a rate determined by the Investigator and the Gleneagles Medical Monitor. Once the MTD has been identified for the schedule, the time of administration may be changed, if indicated (and as agreed between the Investigator and the Gleneagles Medical Monitor).

Valganciclovir is administered orally, and should be taken with food. Serum creatinine or creatinine clearance levels should be monitored carefully. Dosage adjustment is required based on creatinine clearance as shown in the Table below. Valganciclovir dosing may begin on day 7 to 9 of the cycle but must be given for 5 consecutive days.

Creatinine clearance can be calculated from serum creatinine by the following formula:

For males={(140−age[years])×(body weight [kg])}/ {(72)×(0.011×serum creatinine [micromol/L])}

For females=0.85×male value.

TABLE I

Valganciclovir Dosing for Renally Impaired Patients

| Cr CL (ml/min) | Dose Day 1 | Dose Days 2-5 |
|---|---|---|
| ≥60 ml/min | 900 mg (two 450 mg tablets) bid | 900 mg (two 450 mg tablets) qday |
| 40-59 ml/min | 450 mg bid | 450 mg qday |
| 25-39 ml/min | 450 mg | 450 mg Day 3 and Day 5 |
| 10-24 ml/min | 450 mg | 450 mg Day 4 |
| ≤10 ml/min | Not recommended | Not recommended |

The purpose of the Phase 1 study is to establish the MTD, DLT, safety and a RP2D of the investigational agent. Toxic effects are thus the primary study endpoint and will be assessed continuously. Response information will be obtained if patients have disease that can readily be measured and re-assessed. These assessments will be made with every cycle. Furthermore, a response must be noted between two examinations at least 6 weeks apart in order to be documented as a confirmed response to therapy.

Evaluable for toxicity—All patients will be evaluable for toxicity if they receive any study drug.

Evaluable for response—All patients who have received at least a single cycle of treatment and had tumor re-assessment will be considered evaluable for response. In addition, those patients who develop early progressive disease will also be considered evaluable for response. Patients on therapy for at least two cycles of treatment will have their response evaluated.

The determination of antitumor efficacy will be based on objective tumor assessments made according to the Immune-Related Response Criteria (irRC) system of evaluation and treatment decisions by the Investigator will be based on these assessments.

Given the presence of the GM-CSF transgene in Reximmune-C2 and the possibility of an immune response contributing to the tumor effect, the Immune response Criteria will be utilized for clinical response. The reasons for using The immune Response Criteria vs RECIST 1.1 are as follows: (1) the appearance of measurable anti-tumor activity may take longer for immune therapies than for cytotoxic therapies; (2) responses to immune therapy occur after conventional PD; (3) discontinuation of immune therapy may not be appropriate in some cases, unless PD is confirmed (as is usually done for response); (4) allowance for "clinically insufficient" PD (e.g. small new lesions in the presence of other responsive lesions) is recommended; and (5) durable SD may represent antitumor activity.

The comparisons between RECIST 1.1 and the Immune-Related Response Criteria are listed below:

TABLE II

Comparison of WHO RECIST and Immune-Related Response Criteria

| | WHO | irRC |
|---|---|---|
| New measurable lesions (i.e., ≥5 × 5 mm) | Always represent PD | Incorporated into tumor burden |
| New, nonmeasurable lesions (i.e., <5 × 5 mm) | Always represent PD | Do not define progression (but preclude irCR) |
| Non-index lesions | Changes contribute to defining BOR of CR, PR, SD, and PD | Contribute to defining irCR (complete disappearance required) |
| CR | Disappearance of all lesions in two consecutive observations not less than 4 wk apart | Disappearance of all lesions in two consecutive observations not less than 4 wk apart |
| PR | ≥50% decrease in SPD of all index lesions compared with baseline in two observations at least 4 wk apart, in absence of new lesions or unequivocal progression of non-index lesions | ≥50% decrease in tumor burden compared with baseline in two observations at least 4 wk apart |
| SD | 50% decrease in SPD compared with baseline cannot be established nor 25% increase compared with nadir, in absence of new lesions or unequivocal progression of non-index lesions | 50% decrease in tumor burden compared with baseline cannot be established nor 25% increase compared with nadir |
| PD | At least 25% increase in SPD compared with nadir and/or unequivocal progression of non-index lesions and/or appearance of new lesions (any any single time point) | At least 25% increase in tumor burden compared with nadir (at any single time point) in two consecutive observations at least 4 wk apart |

Timing and Type of Assessments

All baseline imaging-based tumor assessments are to be performed within 14 days prior to the start of treatment. For the purposes of this study, all patients' tumor assessments should be re-evaluated starting 9 weeks after initiation of treatment and every 6 weeks thereafter (e.g., Week 9, Week 15, Week 21, etc.) for both Phase IA and Phase IB. All patients with responding tumors (irCR or irPR) must have the response confirmed no less than 6 weeks after the first documentation of response. All patients with tumor progression must have progression confirmed no less than 6 weeks after the first documentation of progression.

The same method of assessment and the same technique should be used to characterize each identified and reported lesion at baseline and during follow-up. Imaging-based evaluation is preferred to evaluation by clinical examination when both methods have been used to assess the antitumor effect of treatment. All measurements should be recorded in metric notation.

CT and CT/PET are the methods for tumor assessments. Conventional CT should be performed with cuts of 10 mm or less in slice thickness contiguously. Spiral CT should be performed using a 5 mm contiguous reconstruction algorithm. This applies to the chest, abdomen, and pelvis.

Chest CT will used for assessment of pulmonary lesions.

Clinical lesions will only be considered measurable when they are superficial (e.g., skin nodules, palpable lymph nodes). In the case of skin lesions, documentation by color photography including a ruler to estimate the size of the lesion is recommended.

[$^{18}$F]FHBG PET-CT scans will be obtained after the patient receives the first three doses of Reximmune-C2 (cycle 1) in Phase IA and after the screening dose of Reximmune-C2 in Phase IB. In Phase IA additional [$^{18}$F]FHBG PET-CT scans can be obtained in subsequent cycles at the discretion of the Investigator and with approval of the Medical Monitor.

Ultrasound should not be used to measure tumor lesions that are clinically not easily accessible for objective response evaluation, e.g., visceral lesions. It is a possible alternative to clinical measurements of superficial palpable nodes, SC lesions, and thyroid nodules. Ultrasound might also be useful to confirm the complete disappearance of superficial lesions usually assessed by clinical examination.

Endoscopy, laparoscopy, and radionuclide scan should not be used for response assessment.

All patients' files and radiological images must be available for source verification and may be submitted for extramural review for final assessment of antitumor activity.

Measurability of Tumor Lesions

At baseline, tumor lesions will be categorized by the Investigator as measurable or non-measurable by the criteria as described below:

Measurable: Lesions that can be accurately measured in at least one dimension (longest diameter to be recorded) as ≥20 mm with conventional techniques or as ≥10 mm with spiral CT scan. Clinical lesions will only be considered measurable when they are superficial (e.g., skin nodules, palpable lymph nodes).

Non-Measurable: All other lesions, including small lesions (longest diameter <20 mm with conventional techniques or <10 mm with spiral CT scan) and bone lesions, leptomeningeal disease, ascites, pleural or pericardial effusions, lymphangitis of the skin or lung, abdominal masses that are not confirmed and followed by imaging techniques, cystic lesions, previously irradiated lesions, and disease documented by indirect evidence only (e.g., by laboratory tests such as alkaline phosphatase).

Note:

Cytology and histology: If measurable disease is restricted to a solitary lesion, its neoplastic nature should be confirmed by cytology/histology.

Response to therapy may also be assessed by independent, central, radiologic blinded review.

Recording Tumor Measurements

All measurable lesions up to a maximum of 10 lesions, representative of all involved organs, should be identified as target lesions and measured and recorded at baseline and at the stipulated intervals during treatment. Target lesions should be selected on the basis of their size (lesion with the longest diameters) and their suitability for accurate repetitive measurements (either by imaging techniques or clinically).

The longest diameter will be recorded for each target lesion. The sum of the longest diameter for all target lesions will be calculated and recorded as the baseline. The sum of the longest diameters is to be used as reference to further characterize the objective tumor response of the measurable dimension of the disease during treatment. All measurements should be recorded in metric notation in centimeters.

All other lesions (or sites of disease) should be identified as non-target lesions and should also be recorded at baseline. Measurements are not required and these lesions should be followed as "present" or "absent."

Definitions of Tumor Response

Immune-Related Response Criteria criteria will be followed for assessment of tumor response.

Determination of Overall Response by Immune-Related Response Criteria

Target Lesions for Solid Tumors

Complete response (irCR) is defined as the disappearance of all lesions (whether measurable or not, and no new lesions); confirmation by a repeat, consecutive assessment no less than 6 weeks from the date first documented.

Partial response (irPR) is defined as a >50% decrease in tumor burden relative to baseline confirmed by a consecutive assessment at least 6 weeks after the first documentation.

Progressive disease (irPD) is defined as a >25% increase in tumor burden relative to nadir (minimum recorded tumor burden) confirmed by a repeat, consecutive assessment no less than 6 weeks from the date first documented lesions recorded since the treatment started, or the appearance of one or more new lesions.

Stable Disease (irSD) is defined as not meeting the criteria for irCR or irPR, in absence of irPD.

Non-Target Lesions for Solid Tumors

The cytological confirmation of the neoplastic origin of any effusion that appears or worsens during treatment when the measurable tumor has met criteria for response or irSD is mandatory to differentiate between response or irSD and irPD.

Confirmation of Tumor Response

To be assigned a status of irPR or irCR, changes in tumor measurements in patients with responding tumors must be confirmed by repeat studies that should be performed ≥6 weeks after the criteria for response are first met. In the case of irSD, follow-up measurements must have met the irSD criteria at least once after study entry at a minimum interval of 6 weeks. When both target and non-target lesions are present, individual assessments will be recorded separately. The overall assessment of response will involve all parameters as depicted in Table III.

The best overall response is the best response recorded from the start of the treatment until disease progression/recurrence (taking as a reference for tumor progression the smallest measurements recorded since the treatment started).

The patient's best response assignment will depend on the achievement of both measurement and confirmation criteria.

Patients will be defined as being not evaluable (NE) for response if there is no post-randomization oncologic assessment. These patients will be counted as failures in the analysis of tumor response data.

Clinical Efficacy Assessment: Performance Status.

Patients will be graded according to the Karnofsky performance status scale as described in Table IV.

TABLE IV

Karnofsky Performance Status Criteria

| Grade | Criterion |
| --- | --- |
| 100 | Normal, no complaints, no evidence of disease |
| 90 | Able to carry on normal activity, minor signs or symptoms of disease |
| 80 | Normal activity with effort, some signs or symptoms of disease |
| 70 | Care for self. Unable to carry on normal activities or to do active work |
| 60 | Requires occasional assistance, but is able to care for most of his/her needs |
| 50 | Requires considerable assistance and frequent medical care |
| 40 | Disabled, requires special care and assistance |
| 30 | Severely disabled, hospitalization is indicated although death not imminent |
| 20 | Hospitalization necessary, very sick, active supportive treatment necessary |
| 10 | Moribund, fatal processes progressing rapidly |
| 0 | Death |

Tumor Marker Response

Method of Assessment

While not a fully validated measure of efficacy in many malignancies, serial determinations of tumor markers may allow evaluation of an easily performed, inexpensive, quantitative, clinical tool as a potential additional means for following the course of the illness during therapy.

A tumor marker decrease or increase will not be assessed as an objective measure of outcome. In particular, a rising tumor marker value will not be considered in the definition of tumor progression, but should prompt a repeat radiographic evaluation to document whether or not radiographic tumor progression has occurred.

Calculated Endpoint Definitions

Survival is defined as the time from date of first study drug treatment to date of death. In the absence of confirmation of death, survival time will be censored at the last date of follow-up.

Tumor response rate is defined as the proportion of patients who have any evidence of objective irCR or irPR.

TTP is defined as the time from treatment to first confirmed documentation of tumor progression or to death due to any cause. For patients who do not have objective evidence of tumor progression and who are either removed from study treatment or are given antitumor treatment other than the study treatment, TTP will be censored. A tumor marker increase meeting criteria for tumor marker progression does not constitute adequate objective evidence of tumor progression. However, such a tumor marker increase should prompt a repeat radiographic evaluation to document whether or not objective tumor progression has occurred.

TTF is defined as the time from treatment to first confirmed documentation of tumor progression, or to off-treatment date, or to death due to any cause, whichever comes first. Patients who are still on treatment at the time of the analysis and patients who are removed from therapy by their physicians during an objective response and who, at the off-treatment date, have no evidence for objective tumor progression will not be considered to have experienced treatment failure, unless the withdrawal is due to the occurrence of a medical event. For these patients, TTF will be censored at the off-study date. Censoring for TTF will also be performed in those patients who are given antitumor treatment, other than the study treatment, before the first of objective tumor progression, off-study date, or death. A tumor marker increase meeting criteria for tumor marker progression does not constitute adequate objective evidence of treatment failure. However, such a tumor marker increase should prompt a repeat radiographic evaluation to document whether or not objective tumor progression (and thus treatment failure) has occurred.

Time to first definitive performance status worsening is the time from treatment until the last time the performance status was no worse than at baseline or to death, due to any cause, in the absence of previous documentation of definitive confirmed performance status worsening. For patients who do not have definitive performance status worsening and who are either removed from study or are given antitumor treatment other than the study treatment, definitive performance status worsening will be censored.

Time to first definitive weight loss is defined as the time from treatment until the last time the percent weight decrease from baseline was <5% or to death due to any cause in the absence of previous documentation of definitive weight loss. For patients who do not have definitive weight loss and who are either removed from study or are given antitumor treatment other than study treatment, definitive weight loss will be censored.

Additional evaluations of the data may include best objective response, confirmed and unconfirmed objective response rate, duration of study treatment, time to first occurrence of new lesions, time to tumor response, stable disease at 24 weeks, and rate of progression free survival at 24 weeks. Data may be evaluated by RECIST 1.1 criteria, if needed.

Treatment Administration Assessment

For both Phase IA and IB: dose intensity is defined as the total dose/cycle times the number of weeks between start of treatment and last treatment plus 13 days.

Percent relative dose intensity is defined as the proportion of the actual dose intensity divided by the planned dose intensity for that same period of time.

ABBREVIATIONS

ALT Alanine aminotransferase
ANC Absolute neutrophil count
AST Aspartate aminotransferase
AUC Area under the plasma concentration-time curve
BSA Body surface area (mg/m$^2$)
CL Systemic plasma clearance
C$_{max}$ Peak plasma concentration
CR Complete response
CRF Case report form
CT Computerized tomography
CTC Common Toxicity Criteria
DLT Dose Limiting Toxicities
EOI End of infusion
FDA Food and Drug Administration
G-CSF Granulocyte-colony stimulating factor (filgrastim, Neupogen®)
GCP Good clinical practice
GM-CSF Granulocyte-macrophage colony-stimulating factor (sargramostim, Leukine®)
HIV Human Immunodeficiency Virus
HR Hazard ratio
IEC Independent Ethics Committee
i.p. Intraperitoneal
IRB Institutional Review Board
IV Intravenous, intravenously
LD$_{10}$ or LD$_{50}$ Dose that is lethal to 10% or 50% of animals
LDH Lactate dehydrogenase
MAD Maximum Administered Dose
MRI Magnetic resonance imaging
MTD Maximum tolerated dose
NCI National Cancer Institute
NE Not evaluable for tumor response
NOAEL No Observed Adverse Effect Level
Non-CR Non-complete response
Non-PD Non-progressive disease
PBMC Peripheral Blood Mononuclear Cells
PCE Propylene Glycol: Cremophor® EL: Ethanol
PD Progressive disease
PR Partial response
SAER-S Serious Adverse Event Report-Study
SC Subcutaneous, subcutaneously
SD Stable disease
STD$_{10}$ Dose that is severely toxic to 10% of animals
TTP Time to Progression
TTF Time to Failure
T$_{1/2}$ Half-life
T$_{max}$ Time of maximum plasma concentration
V$_{ss}$ Steady state volume of distribution While preferred embodiments have been shown and described herein, it will be obvious to those skilled in the art that such embodiments are provided by way of example only. Numerous variations, changes, and substitutions will now occur to those skilled in the art without departing from the disclosed embodiments. It should be understood that various alternatives to the embodiments described herein may be employed in practicing the embodiments. It is intended that the following claims define the scope of the embodiments and that methods and structures within the scope of these claims and their equivalents be covered thereby.

REFERENCES

1. Lentivirus-based DsRed-2-transfected pancreatic cancer cells for deep in vivo imaging of metastatic disease. Yu Z, Zhou J, Hoffman R M., Methods Mol Biol. 2012; 872: 69-83. doi: 10.1007/978-1-61779-797-2_5.
2. Color-coded real-time subcellular fluorescence imaging of the interaction between cancer and host cells in live mice. Yamauchi K, Tome Y, Yamamoto N, Hayashi K, Kimura H, Tsuchiya H, Tomita K, Bouvet M, Hoffman R M. Anticancer Res. 2012 January; 32(1):39-43.
3. Lentivirus-based DsRed-2-transfected pancreatic cancer cells for deep in vivo imaging of metastatic disease. Zhou J, Yu Z, Zhao S, Hu L, Zheng J, Yang D, Bouvet M, Hoffman R M. J Surg Res. 2009 November; 157(1):63-70. doi: 10.1016/j.jss.2008.08.027. Epub 2008 Oct. 9.
4. Fluorescent LYVE-1 antibody to image dynamically lymphatic trafficking of cancer cells in vivo. McElroy M, Hayashi K, Garmy-Susini B, Kaushal S, Varner J A, Moossa A R, Hoffman R M, Bouvet M. J Surg Res. 2009 January; 151(1):68-73. doi: 10.1016/j.jss.2007.12.769. Epub 2008 Jan. 18.
5. Lentiviral reporter constructs for fluorescence tracking of the temporospatial pattern of Smad3 signaling. Stuelten C H, Kamaraju A K, Wakefield L M, Roberts A B. Biotechniques. 2007 September; 43(3):289-90, 292, 294.
6. Subcellular imaging in the live mouse. Hoffman R M, Yang M. Nat. Protoc. 2006; 1(2):775-82.
7. In vivo color-coded imaging of the interaction of colon cancer cells and splenocytes in the formation of liver metastases. Bouvet M, Tsuji K, Yang M, Jiang P, Moossa A R, Hoffman R M. Cancer Res. 2006 Dec. 1; 66(23): 11293-7.
8. Dual-color imaging of nuclear-cytoplasmic dynamics, viability, and proliferation of cancer cells in the portal vein area. Tsuji K, Yamauchi K, Yang M, Jiang P, Bouvet M, Endo H, Kanai Y, Yamashita K, Moossa A R, Hoffman R M. Cancer Res. 2006 Jan. 1; 66(1):303-6.
9. FL-CTL assay: fluorolysometric determination of cell-mediated cytotoxicity using green fluorescent protein and red fluorescent protein expressing target cells. Chen K, Chen L, Zhao P, Marrero L, Keoshkerian E, Ramsay A, Cui Y. J Immunol Methods. 2005 May; 300(1-2):100-14.
10. Murine leukemia virus (MLV) replication monitored with fluorescent proteins. Sliva K, Erlwein O, Bittner A, Schnierle B S. Virol J. 2004 Dec. 20; 1:14.
11. Real-time whole-body imaging of an orthotopic metastatic prostate cancer model expressing red fluorescent protein. Yang M, Jiang P, Yamamoto N, Li L, Geller J, Moossa A R, Hoffman R M. Prostate. 2005 Mar. 1; 62(4):374-9.
12. Cellular dynamics visualized in live cells in vitro and in vivo by differential dual-color nuclear-cytoplasmic fluorescent-protein expression. Yamamoto N, Jiang P, Yang M, Xu M, Yamauchi K, Tsuchiya H, Tomita K, Wahl G M, Moossa A R, Hoffman R M. Cancer Res. 2004 Jun. 15; 64(12):4251-6.
13. In vivo imaging with fluorescent proteins: the new cell biology. Hoffman R M. Acta Histochem. 2004; 106(2): 77-87.
14. Real-time imaging of individual fluorescent-protein color-coded metastatic colonies in vivo. Yamamoto N, Yang M, Jiang P, Xu M, Tsuchiya H, Tomita K, Moossa A R, Hoffman R M. Clin Exp Metastasis. 2003; 20(7): 633-8.
15. Yaghoubi S, Barrio J R, Dahlbom M, Iyer M, Namavari M, Satyamurthy N, Goldman R, Herschman H R, Phelps M E, Gambhir S S. Human pharmacokinetic and dosimetry studies of [(18)F]FHBG: a reporter probe for imaging herpes simplex virus type-1 thymidine kinase reporter gene expression. J Nucl Med. 2001 August; 42(8):1225-34.
16. Pañeda A, Collantes M, Beattie S G, Otano I, Snapper J, Timmermans E, Guembe L, Petry H, Lanciego J L, Benito A, Prieto J, Rodriguez-Pena M S, Peñuelas I, Gonzalez-Aseguinolaza G. Adeno-associated virus liver transduction efficiency measured by in vivo [$^{18}$F]FHBG positron emission tomography imaging in rodents and nonhuman primates. Hum Gene Ther. 2011 August; 22(8):999-1009. doi: 10.1089/hum.2010.190. Epub 2011 Apr. 6.
17. Johnson M, Karanikolas B D, Priceman S J, Powell R, Black M E, Wu H M, Czernin J, Huang S C, Wu L. Titration of variant HSV1-tk gene expression to determine the sensitivity of [$^{18}$F]FHBG PET imaging in a prostate tumor. J Nucl Med. 2009 May; 50(5):757-64. doi: 10.2967/jnumed.108.058438. Epub 2009 Apr. 16.
18. Peñuelas I, Mazzolini G, Boán J F, Sangro B, Martí-Climent J, Ruiz M, Ruiz J, Satyamurthy N, Qian C, Barrio J R, Phelps M E, Richter J A, Gambhir S S, Prieto J. Positron Emission Tomography Imaging of Adenoviral-Mediated Transgene Expression in Liver Cancer Patients Gastro (2005) 128:1787.
19. Sangro B, Mazzolini G, Ruiz M, Ruiz J, Quiroga J, Herrero I, Qian C, Benito A, Larrache J, Olagüe C, Boan J, Peñuelas I, Sádaba B, Prieto J. A phase I clinical trial of thymidine kinase-based gene therapy in advanced hepatocellular carcinoma Can. Gene Ther. (2010) 17: 837-843.
20. Willmann J K, Paulmurugan R, Rodriguez-Porcel M, Stein W, Brinton T J, Connolly A J, Nielsen C H, Lutz A M, Lyons J, Ikeno F, Suzuki Y, Rosenberg J, Chen I Y, Wu J C, Yeung A C, Yock P, Robbins R C, Gambhir S S. Imaging gene expression in human mesenchymal stem cells: from small to large animals. Radiology. 2009 July; 252(1):117-27. doi: 10.1148/radiol.2513081616. Epub 2009 Apr. 14. PubMed PMID: 19366903; PubMed Central PMCID: PMC2702468.
21. Yaghoubi S S, Jensen M C, Satyamurthy N, Budhiraja S, Paik D, Czernin J, Gambhir S S. Noninvasive detection of therapeutic cytolytic T cells with [$^{18}$F]FHBG PET in a patient with glioma. Nat Clin Pract Oncol. 2009 January; 6(1):53-8. doi: 10.1038/ncponc1278. Epub 2008 Nov. 18. PubMed PMID: 19015650; PubMed Central PMCID: PMC3526373.
22. Roelants V, Labar D, de Meester C, Havaux X, Tabilio A, Gambhir S S, Di Ianni M, Bol A, Bertrand L, Vanoverschelde J L. Comparison between adenoviral and retroviral vectors for the transduction of the thymidine kinase PET reporter gene in rat mesenchymal stem cells. J Nucl Med. 2008 November; 49(11):1836-44. doi: 10.2967/jnumed.108.052175. Erratum in: J Nucl Med. 2009 January; 50(1):17. PubMed PMID: 18984872.
23. Lee S W, Padmanabhan P, Ray P, Gambhir S S, Doyle T, Contag C, Goodman S B, Biswal S. Stem cell-mediated accelerated bone healing observed with in vivo molecular and small animal imaging technologies in a model of skeletal injury. J Orthop Res. 2009 March; 27(3):295-302. doi: 10.1002/jor.20736. PubMed PMID: 18752273.
24. Chin F T, Namavari M, Levi J, Subbarayan M, Ray P, Chen X, Gambhir S S. Semiautomated radiosynthesis and biological evaluation of [$^{18}$F]FEAU: a novel PET imaging agent for HSV1-tk/sr39tk reporter gene expression. Mol Imaging Biol. 2008 March-April; 10(2):82-91. Epub 2007 Dec. 22. PubMed PMID: 18157580.
25. Yaghoubi S S, Gambhir S S. PET imaging of herpes simplex virus type 1 thymidine kinase (HSV1-tk) or mutant HSV1-sr39tk reporter gene expression in mice and humans using [$^{18}$F]FHBG. Nat Protoc. 2006; 1(6):3069-75. PubMed PMID: 17406570.
26. Deroose C M, De A, Loening A M, Chow P L, Ray P, Chatziioannou A F, Gambhir S S. Multimodality imaging of tumor xenografts and metastases in mice with combined small-animal PET, small-animal CT, and bioluminescence imaging. J Nucl Med. 2007 February; 48(2): 295-303. PubMed PMID: 17268028; PubMed Central PMCID: PMC3263830.
27. Kim S J, Doudet D J, Studenov A R, Nian C, Ruth T J, Gambhir S S, McIntosh C H. Quantitative micro positron emission tomography (PET) imaging for the in vivo determination of pancreatic islet graft survival. Nat Med. 2006 December; 12(12):1423-8. Epub 2006 Dec. 3. PubMed PMID: 17143277.
28. Yaghoubi S S, Couto M A, Chen C C, Polavaram L, Cui G, Sen L, Gambhir S S. Preclinical safety evaluation of [$^{18}$F]FHBG: a PET reporter probe for imaging herpes 28. simplex virus type 1 thymidine kinase (HSV1-tk) or mutant HSV1-sr39tk's expression. J Nucl Med. 2006 April; 47(4):706-15. PubMed PMID: 16595506.
29. Xiong Z, Cheng Z, Zhang X, Patel M, Wu J C, Gambhir S S, Chen X. Imaging chemically modified adenovirus for targeting tumors expressing integrin alphavbeta3 in living mice with mutant herpes simplex virus type 1 thymidine kinase PET reporter gene. J Nucl Med. 2006 January; 47(1):130-9. PubMed PMID: 16391197.
30. Shu C J, Guo S, Kim Y J, Shelly S M, Nijagal A, Ray P, Gambhir S S, Radu C G, Witte O N. Visualization of a primary anti-tumor immune response by positron emission tomography. Proc Natl Acad Sci USA. 2005 Nov. 29; 102(48):17412-7. Epub 2005 Nov. 17. PubMed PMID: 16293690; PubMed Central PMCID: PMC1283986.
31. Sen L, Gambhir S S, Furukawa H, Stout D B, Linh Lam A, Laks H, Cui G. Noninvasive imaging of ex vivo intracoronarily delivered nonviral therapeutic transgene expression in heart. Mol Ther. 2005 July; 12(1):49-57. PubMed PMID: 15963920.
32. Yaghoubi S S, Barrio J R, Namavari M, Satyamurthy N, Phelps M E, Herschman H R, Gambhir S S. Imaging progress of herpes simplex virus type 1 thymidine kinase suicide gene therapy in living subjects with positron emission tomography. Cancer Gene Ther. 2005 March; 12(3):329-39. PubMed PMID: 15592447.
33. Miyagawa M, Anton M, Haubner R, Simoes M V, Städele C, Erhardt W, Reder S, Lehner T, Wagner B, Noll S, Noll B, Grote M, Gambhir S S, Gansbacher B, Schwaiger M, Bengel F M. PET of cardiac transgene expression: comparison of 2 approaches based on herpesviral thymidine kinase reporter gene. J Nucl Med. 2004 November; 45(11):1917-23. PubMed PMID: 15534063.
34. Green L A, Nguyen K, Berenji B, Iyer M, Bauer E, Barrio J R, Namavari M, Satyamurthy N, Gambhir S S. A tracer kinetic model for [$^{18}$F]FHBG for quantitating herpes simplex virus type 1 thymidine kinase reporter gene expression in living animals using PET. J Nucl Med. 2004 September; 45(9):1560-70. PubMed PMID: 15347725.
35. Wu J C, Chen I Y, Wang Y, Tseng J R, Chhabra A, Salek M, Min J J, Fishbein M C, Crystal R, Gambhir S S. Molecular imaging of the kinetics of vascular endothelial growth factor gene expression in ischemic myocardium. Circulation. 2004 Aug. 10; 110(6):685-91. PubMed PMID: 15302807.
36. Su H, Forbes A, Gambhir S S, Braun J. Quantitation of cell number by a positron emission tomography reporter gene strategy. Mol Imaging Biol. 2004 May-June; 6(3): 139-48. PubMed PMID: 15193248.
37. Chen I Y, Wu J C, Min J J, Sundaresan G, Lewis X, Liang Q, Herschman H R, Gambhir S S. Micro-positron emission tomography imaging of cardiac gene expression in rats using bicistronic adenoviral vector-mediated gene delivery. Circulation. 2004 Mar. 23; 109(11):1415-20. Epub 2004 Mar. 8. PubMed PMID: 15007006.
38. Sundaresan G, Paulmurugan R, Berger F, Stiles B, Nagayama Y, Wu H, Gambhir S S. MicroPET imaging of Cre-loxP-mediated conditional activation of a herpes simplex virus type 1 thymidine kinase reporter gene. Gene Ther. 2004 April; 11(7):609-18. PubMed PMID: 14724687.
39. Green L A, Yap C S, Nguyen K, Barrio J R, Namavari M, Satyamurthy N, Phelps M E, Sandgren E P, Herschman H R, Gambhir S S. Indirect monitoring of endogenous gene expression by positron emission tomography (PET) imaging of reporter gene expression in transgenic mice. Mol Imaging Biol. 2002 January; 4(1):71-81. PubMed PMID: 14538050.
40. Ghosh P. Reproducible quantification in PET-CT: Clinical relevance and technological approaches. White Paper Siemens (February 2012).
41. Shankar L. K. et al. Consensus recommendations for the use of 18F-FDG as an indicator of therapeutic response in National Cancer Institute trials. J. Nucl. Med. 2006 June; 47:1059-66.
42. Bar-Shir A. et al. Transforming thymidine into a magnetic resonance imaging probe for gene expression. J. Am. Chem. Soc. 2013 January; 135:1617-24.
43. Muller U. et al. Synthesis and pre-clinical evaluation of a new C-6 alkylated pyrimidine derivative as a PET imaging agent for HSV1-tk gene expression. Am. J. Nucl. Med. Mol. Imaging 2013; 3:71-84.
44. Mescic A. et al. C-5 hydroxyethyl and hydroxypropyl acyclonucleosides as substrates for thymidine kinase of Herpes simplex virus type 1 (HSV-1 TK): Syntheses and biological evaluation. Molecules 2013; 18:5104-24.

```
SEQUENCES

SEQ ID NO: 1: wild type HSV1-TK nucleotide sequence
atggcttcgtaccccggccatcaacacgcgtctgcgttcgaccaggctgcgcgttctcgcggccatagcaaccgacgtac
ggcgttgcgccctcgccggcagcaagaagccacggaagtccgcccggagcagaaaatgcccacgctactgcgggtttata
tagacggtccccacgggatggggaaaaccaccaccacgcaactgctggtggccctgggttcgcgcgacgatatcgtctac
gtacccgagccgatgacttactggcgggtgcttgggggcttccgagacaatcgcgaacatctacaccacaacaccgcct
cgaccagggtgagatatcggccggggacgcggcggtggtaatgacaagcgcccagataacaatgggcatgccttatgccg
tgaccgacgccgttctggctcctcatatcgggggggaggctgggagctcacatgccccgcccccggccctcaccctcatc
ttcgaccgccatcccatcgccgccctcctgtgctacccggccgcgcggtaccttatgggcagcatgacccccaggccgt
gctggcgttcgtggccgttcatcccgccgaccttgcccggcaccaacatcgtgcttgctggtcttgccaaacgcctccgt
tcgaccgcctggccaaacgccagcgccccggcgagcggctggacctggctatgctggctgcgattcgccgcgtttacggg
ctacttgccaatacggtgcggtatctgcagtgcggcgggtcgtggcgggaggactggggacagcttcggggacggccgt
gccgccccagggtgccgagccccagagcaacgcgggccacgacccatatcggggacacgttattaccctgtttcggg
ccccccgagttgctggccccaacggcgacctgtataacgtgtttgcctgggccttggacgtcttggccaaacgcctccgt
tccatgcacgtctttatcctggattacgaccaatcgcccgccggctgccgggacgccctgctgcaacttacctccgggat
ggtccagacccacgtcaccaccccggctccataccgacgatatgcgacctggcgcgcacgtttgcccgggagatgggg
aggctaactga SEQ ID NO: 2: wild type HSV1-TK amino acid sequence
MASYPGHQHASAFDQAARSRGHSNRRTALRPRRQQEATEVRPEQKMPTLLRVYIDGPHGMGKTTTTQLLVALGSRDDIVY
VPEPMTYWRVLGASETIANIYTTQHRLDQGEISAGDAAVVMTSAQITMGMPYAVTDAVLAPHIGGEAGSSHAPPPALTLI
FDRHPIAALLCYPAARYLMGSMTPQAVLAFVALIPPTLPGTNIVLGALPEDRHIDRLAKRQRPGERLDLAMLAAIRRVYG
LLANTVRYLQCGGSWREDWGQLSGTAVPPQGAEPQSNAGPRPHIGDTLFTLFRAPELLAPNGDLYNVFAWALDVLAKRLR
SMHVFILDYDQSPAGCRDALLQLTSGMVQTHVTTPGSIPTICDLARTFAREMGEAN
```

SEQUENCES

SEQ ID NO: 3: HSV-TK in Reximmune-C HSV-TK; SR 39 mutant and R25G-R265 Mutation of NLS atggcctcgtaccccggccatcaacacgcgtctgcgttcgaccaggctgcgcgttctcgcggccatagcaacg
gatccacggcgttgcgccctcgccggcagcaagaagccacggaagtccgcccggagcagaaaatgcccacgct
actgcgggtttatatagacggtccccacgggatggggaaaaccaccaccacgcaactgctggtggccctgggt
tcgcgcgacgatatcgtctacgtacccgagccgatgacttactggcgggtgctgggggcttccgagacaatcg
cgaacatctacaccacacaacaccgcctcgaccagggtgagatatcggccggggacgcggcggtggtaatgac
aagcgcccagataacaatgggcatgccttatgccgtgaccgacgccgttctggctcctcatatcggggggggag
gctgggagctcacatgccccgcccccggccctcaccatcttcctcgaccgccatcccatcgccttcatgctgt
gctaccggccgcgcggtaccttatgggcagcatgaccccccaggccgtgctggcgttcgtggccctcatccc
gccgaccttgcccggcaccaacatcgtgcttgggcccttccggaggacagacacatcgaccgcctggccaaa
cgccagcgccccggcgagcggctggacctggctatgctggctgcgattcgccgcgtttacgggctacttgcca
atacggtgcggtatctgcagtgcggcgggtcgtggcgggaggactgggacagctttcggggacggccgtgcc
gccccagggtgccgagcccagagcaacgcgggcccacgaccccatatcggggacacgttatttaccctgttt
cggggcccccgagttgctggcccccaacggcgacctgtataacgtgtttgcctgggccttggacgtcttggcca
aacgcctccgttccatgcacgtctttatcctggattacgaccaatcgcccgccggctgccgggacgccctgct
gcaacttacctccgggatggtccagacccacgtcaccaccccggctccataccgacgatatgcgacctggcg
cgcacgtttgcccgggagatgggggaggctaactga SEQ ID NO: 4 (amino acid sequence encoded by SEQ ID NO: 3)
MASYPGHQHASAFDQAARSRGHSNGSTALRPRRQQEATEVRPEQKMPTLLRVYIDGPHGMGKTTTTQLLVALG
SRDDIVYVPEPMTYWRVLGASETIANIYTTQHRLDQGEISAGDAAVVMTSAQITMGMPYAVTDAVLAPHIGGE
AGSSHAPPPALTIFLDRHPIAFMLCYPAARYLMGSMTPQAVLAFVALIPPTLPGTNIVLGALPEDRHIDRLAK
RQRPGERLDLAMLAAIRRVYGLLANTVRYLQCGGSWREDWGQLSGTAVPPQGAEPQSNAGPRPHIGDTLFTLF
RAPELLAPNGDLYNVFAWALDVLAKRLRSMHVFILDYDQSPAGCRDALLQLTSGMVQTHVTTPGSIPTICDLA
RTFAREMGEAN SEQ ID NO: 5: HSV-TK Sites to mutate are in bold, underlining (HSV-TK nuclear localization sequence, RR, and Substrate Binding Domain, LIF and AAL

```
atggcctcgtaccccggccatcaacacgcgtctgcgttcgaccaggctgcgcgttctcgc              60
 M  A  S  Y  P  G  H  Q  H  A  S  A  F  D  Q  A  A  R  S  R
ggccatagcaaccgacgtacggcgttgcgccctcgccggcagcaagaagccacggaagtc             120
 G  H  S  N  R  R  T  A  L  R  P  R  R  Q  Q  E  A  T  E  V
cgcccggagcagaaaatgcccacgctactgcgggtttatatagacggtccccacgggatg             180
 R  P  E  Q  K  M  P  T  L  L  R  V  Y  I  D  G  P  H  G  M
gggaaaaccaccaccacgcaactgctggtggccctgggttcgcgcgacgatatcgtctac             240
 G  K  T  T  T  T  Q  L  L  V  A  L  G  S  R  D  D  I  V  Y
gtacccgagccgatgacttactggcgggtgctgggggcttccgagacaatcgcgaacatc             300
 V  P  E  P  M  T  Y  W  R  V  L  G  A  S  E  T  I  A  N  I
tacaccacacaacaccgcctcgaccagggtgagatatcggccggggacgcggcggtggta             360
 Y  T  T  Q  H  R  L  D  Q  G  E  I  S  A  G  D  A  A  V  V
atgacaagcgcccagataacaatgggcatgccttatgccgtgaccgacgccgttctggct             420
 M  T  S  A  Q  I  T  M  G  M  P  Y  A  V  T  D  A  V  L  A
cctcatatcgggggggaggctgggagctcacatgccccgcccccggccctcaccctcatc             480
 P  H  I  G  G  E  A  G  S  S  H  A  P  P  P  A  L  T  L  I
ttcgaccgccatcccatcgccgccctctgtgctaccggccgcgcggtaccttatgggc               540
 F  D  R  H  P  I  A  A  L  C  Y  P  A  A  R  Y  L  M  G
agcatgaccccccaggccgtgctggcgttcgtggccctcatcccgccgaccttgcccggc             600
 S  M  T  P  Q  A  V  L  A  F  V  A  L  I  P  P  T  L  P  G
accaacatcgtgcttgggcccttccggaggacagacacatcgaccgcctggccaaacgc              660
 T  N  I  V  L  G  A  L  P  E  D  R  H  I  D  R  L  A  K  R
cagcgccccggcgagcggctggacctggctatgctggctgcgattcgccgcgtttacggg             720
 Q  R  P  G  E  R  L  D  L  A  M  L  A  A  I  R  R  V  Y  G
ctacttgccaatacggtgcggtatctgcagtgcggcgggtcgtggcgggaggactgggga             780
 L  L  A  N  T  V  R  Y  L  Q  C  G  G  S  W  R  E  D  W  G
cagctttcggggacggccgtgccgccccagggtgccgagcccagagcaacgcgggccca             840
 Q  L  S  G  T  A  V  P  P  Q  G  A  E  P  Q  S  N  A  G  P
cgaccccatatcggggacacgttatttaccctgtttcggggcccccgagttgctggcccc             900
 R  P  H  I  G  D  T  L  F  T  L  F  R  A  P  E  L  L  A  P
aacggcgacctgtataacgtgtttgcctgggccttggacgtcttggccaaacgcctccgt             960
 N  G  D  L  Y  N  V  F  A  W  A  L  D  V  L  A  K  R  L  R
tccatgcacgtctttatcctggattacgaccaatcgcccgccggctgccgggacgccctg            1020
 S  M  H  V  F  I  L  D  Y  D  Q  S  P  A  G  C  R  D  A  L
ctgcaacttacctccgggatggtccagacccacgtcaccaccccggctccataccgacg             1080
 L  Q  L  T  S  G  M  V  Q  T  H  V  T  T  P  G  S  I  P  T
atatgcgacctggcgcgcacgtttgcccgggagatgggggaggctaactga
 I  C  D  L  A  R  T  F  A  R  E  M  G  E  A  N  *
```

SEQ ID NOS: 6 and 7: Sac I-Kpn I (SR39) mutant region
GAGCTCACATGCCCCGCCCCCGGCCCTCACCATCTTCCTCGACCGCCATCCCATCGCC-
CTCGAGTGTACGGGGCGGGGGCCGGGAGTGGTAGAAGGAGCTGGCGGTAGGGTAGCGG-
Sac I -TTCATGCTGTGCTACCCGGCCGCGCGGTACC (SEQ ID NO: 6)
-AAGTACGACACGATGGGCCGGCGCGCCATGG (SEQ ID NO: 7)
                                     Kpn I -continued

| SEQUENCES |
|---|

```
Kpn I  GGTACC G    G T A C / C GTAC-3'
               C / C A T G   G

Sac I  GAGCTC G    A G C T / C AGCT-3'
               C / T C G A   G

SEQ ID NOS: 8 and 9: Sac I-Kpn I (SR39) mutant region (cut)
CACATGCCCCGCCCCGGCCCTCACCATCTTCCTCGACCGCCATCCCATCGCCTTCATG
TCGAGTGTACGGGGCGGGGCCGGGAGTGGTAGAAGGAGCTGGCGGTAGGGTAGCGGAA
Sac I(cut)

CTGTGCTACCCGGCCGCGCGGTAC   (SEQ ID NO: 8)
GTACGACACGATGGGCCGGC       (SEQ ID NO: 9)
                   Kpn I (cut)

Kpn I  GGTACC G    G T A C / C GTAC-3'
               C / C A T G   G

SEQ ID NOS: 10 and 11: Primers
SR39sackpn F1
5' CACATGCCCCGCCCCGGCCCTCACCATCTTCCTCGACCGCCATCCCATCGCCTTCATGCTGTGCTACCCG
GCCGCGCGGTAC 3' (SEQ ID NO: 10)

SR39sackpn R1
5' CGCGCGGCCGGGTAGCACAGCATGAAGGCGATGGGATGGCGGTCGAGGAAGATGGTGAGGGCCGGGGCGG
GGCATGTGAGCT 3' (SEQ ID NO: 11)

SEQ ID NO: 12 Gene #3 mHSV-TK CO A168H (LIF . . . AHL): Length: 1185
GTCAGCGGCCGCACCGGTACGCGTCCACCATGGCCAGCTACCCCGGCCACCAGCACGCCAGCGCCTT
CGACCAGGCCGCCCGCAGCCGCGGCCACAGCAACGGCAGCACCGCACTGCGGCCACGGCGCCAGCAG
GAGGCCACCGAGGTGCGCCCCGAGCAGAAGATGCCCACCCTGCTGCGCGTGTACATCGACGGACCAC
ACGGCATGGGCAAGACCACCACCACCCAGCTGCTGGTGGCCCTGGGCAGCCGCGACGACATCGTGTA
CGTGCCCGAGCCCATGACCTACTGGCGCGTGCTGGGCGCCAGCGAGACCATCGCCAACATCTACACC
ACCCAGCACCGCCTGGACCAAGGCGAGATCAGCGCCGGCGACGCCGCCGTGGTGATGACCAGCGCCC
AGATTACAATGGGCATGCCCTACGCCGTGACCGACGCCGTGCTGGCACCACACATCGGCGGCGAGGC
CGGCAGCAGCCACGCACCACCACCAGCACTGACCCTGATCTTCGACCGGCACCCAATCGCACACCTG
CTGTGCTACCCGGCAGCACGCTACCTGATGGGCTCCATGACACCACAAGCCGTGCTGGCCTTCGTGG
CCCTGATCCCACCAACACTGCCCGGCACCAACATCGTGCTGGGCGCCCTGCCCGAGGACCGCCACAT
CGACCGCCTGGCCAAGCGCCAGCGCCCCGGCGAGCGCCTGGACCTGGCCATGCTGGCCGCCATCCGC
CGCGTGTACGGCCTGCTGGCCAACACCGTGCGCTACCTGCAGTGCGGCGGCAGCTGGCGCGAGGACT
GGGGCCAGCTGAGCGGCACCGCCGTGCCACCACAGGGCGCCGAGCCACAGAGCAACGCCGGACCACG
ACCACACATCGGCGACACCCTGTTCACCCTGTTCCGGGCACCAGAGCTGCTGGCACCAAACGGCGAC
CTGTACAACGTGTTCGCCTGGGCCCTGGACGTGCTGGCCAAGCGCCTGCGCTCCATGCACGTGTTCA
TCCTGGACTACGACCAGTCACCGGCCGGCTGCCGCGACGCCCTGCTGCAGCTGACCAGCGGCATGGT
GCAGACCCACGTGACAACACCCGGCAGCATCCCAACAATCTGCGACCTGGCCCGCACCTTCGCCCGC
GAGATGGGCGAGGCCAACTAATAGGGATCCCTCGAGAAGCTTGTCA SEQ ID NO: 13 Gene #4 mHSV-TK CO TK A167F (LIF . . . FAL): Length: 1185
GTCAGCGGCCGCACCGGTACGCGTCCACCATGGCCAGCTACCCCGGCCACCAGCACGCCAGCGCCTT
CGACCAGGCCGCCCGCAGCCGCGGCCACAGCAACGGCAGCACCGCACTGCGGCCACGGCGCCAGCAG
GAGGCCACCGAGGTGCGCCCCGAGCAGAAGATGCCCACCCTGCTGCGCGTGTACATCGACGGACCAC
ACGGCATGGGCAAGACCACCACCACCCAGCTGCTGGTGGCCCTGGGCAGCCGCGACGACATCGTGTA
CGTGCCCGAGCCCATGACCTACTGGCGCGTGCTGGGCGCCAGCGAGACCATCGCCAACATCTACACC
ACCCAGCACCGCCTGGACCAAGGCGAGATCAGCGCCGGCGACGCCGCCGTGGTGATGACCAGCGCCC
AGATTACAATGGGCATGCCCTACGCCGTGACCGACGCCGTGCTGGCACCACACATCGGCGGCGAGGC
CGGCAGCAGCCACGCACCACCACCAGCACTGACCCTGATCTTCGACCGGCACCCAATCTTCGCACTG
CTGTGCTACCCGGCAGCACGCTACCTGATGGGCTCCATGACACCACAAGCCGTGCTGGCCTTCGTGG
CCCTGATCCCACCAACACTGCCCGGCACCAACATCGTGCTGGGCGCCCTGCCCGAGGACCGCCACAT
CGACCGCCTGGCCAAGCGCCAGCGCCCCGGCGAGCGCCTGGACCTGGCCATGCTGGCCGCCATCCGC
CGCGTGTACGGCCTGCTGGCCAACACCGTGCGCTACCTGCAGTGCGGCGGCAGCTGGCGCGAGGACT
GGGGCCAGCTGAGCGGCACCGCCGTGCCACCACAGGGCGCCGAGCCACAGAGCAACGCCGGACCACG
ACCACACATCGGCGACACCCTGTTCACCCTGTTCCGGGCACCAGAGCTGCTGGCACCAAACGGCGAC
CTGTACAACGTGTTCGCCTGGGCCCTGGACGTGCTGGCCAAGCGCCTGCGCTCCATGCACGTGTTCA
TCCTGGACTACGACCAGTCACCGGCCGGCTGCCGCGACGCCCTGCTGCAGCTGACCAGCGGCATGGT
GCAGACCCACGTGACAACACCCGGCAGCATCCCAACAATCTGCGACCTGGCCCGCACCTTCGCCCGC
GAGATGGGCGAGGCCAACTAATAGGGATCCCTCGAGAAGCTTGTCA SEQ ID NO: 14 Gene #5 mHSV-TK CO dual mutant A167F-A168H (LIF . . . FHL):
Length: 1185
GTCAGCGGCCGCACCGGTACGCGTCCACCATGGCCAGCTACCCCGGCCACCAGCACGCCAGCGCCTT
CGACCAGGCCGCCCGCAGCCGCGGCCACAGCAACGGCAGCACCGCACTGCGGCCACGGCGCCAGCAG
GAGGCCACCGAGGTGCGCCCCGAGCAGAAGATGCCCACCCTGCTGCGCGTGTACATCGACGGACCAC
ACGGCATGGGCAAGACCACCACCACCCAGCTGCTGGTGGCCCTGGGCAGCCGCGACGACATCGTGTA
CGTGCCCGAGCCCATGACCTACTGGCGCGTGCTGGGCGCCAGCGAGACCATCGCCAACATCTACACC
ACCCAGCACCGCCTGGACCAAGGCGAGATCAGCGCCGGCGACGCCGCCGTGGTGATGACCAGCGCCC
AGATTACAATGGGCATGCCCTACGCCGTGACCGACGCCGTGCTGGCACCACACATCGGCGGCGAGGC
CGGCAGCAGCCACGCACCACCACCAGCACTGACCCTGATCTTCGACCGGCACCCAATCTTCCACCTG
```

| SEQUENCES |
| --- |
| CTGTGCTACCCGGCAGCACGCTACCTGATGGGCTCCATGACACCACAAGCCGTGCTGGCCTTCGTGG
CCCTGATCCCACCAACACTGCCCGGCACCAACATCGTGCTGGGCGCCCTGCCCGAGGACCGCCACAT
CGACCGCCTGGCCAAGCGCCAGCGCCCCGGCGAGCGCCTGGACCTGGCCATGCTGGCCGCCATCCGC
CGCGTGTACGGCCTGCTGGCCAACACCGTGCGCTACCTGCAGTGCGGCGGCAGCTGGCGCGAGGACT
GGGGCCAGCTGAGCGGCACCGCCGTGCCACCACAGGGCGCCGAGCCACAGAGCAACGCCGGACCACG
ACCACACATCGGCGACACCCTGTTCACCCTGTTCCGGGCACCAGAGCTGCTGGCACCAAACGGCGAC
CTGTACAACGTGTTCGCCTGGGCCCTGGACGTGCTGGCCAAGCGCCTGCGCTCCATGCACGTGTTCA
TCCTGGACTACGACCAGTCACCGGCCGGCTGCCGCGACGCCCTGCTGCAGCTGACCAGCGGCATGGT
GCAGACCCACGTGACAACACCCGGCAGCATCCCAACAATCTGCGACCTGGCCCGCACCTTCGCCCGC
GAGATGGGCGAGGCCAACTAATAGGGATCCCTCGAGAAGCTTGTCA |

SEQ ID NO: 15 Gene #6 mHSV-TK CO MB-IFL A168H (IFL . . . AHL): Length: 1185
GTCAGCGGCCGCACCGGTACGCGTCCACCATGGCCAGCTACCCCGGCCACCAGCACGCCAGCGCCTT
CGACCAGGCCGCCCGCAGCCGCGGCCACAGCAACGGCAGCACCGCACTGCGGCCACGGCGCCAGCAG
GAGGCCACCGAGGTGCGCCCCGAGCAGAAGATGCCCACCCTGCTGCGCGTGTACATCGACGGACCAC
ACGGCATGGGCAAGACCACCACCACCCAGCTGCTGGTGGCCCTGGGCAGCCGCGACGACATCGTGTA
CGTGCCCGAGCCCATGACCTACTGGCGCGTGCTGGGCGCCAGCGAGACCATCGCCAACATCTACACC
ACCCAGCACCGCCTGGACCAAGGCGAGATCAGCGCCGGCGACGCCCGCCGTGGTGATGACCAGCGCCC
AGATTACAATGGGCATGCCCTACGCCGTGACCGACGCCGTGCTGGCACCACACATCGGCGGCGAGGC
CGGCAGCAGCCACGCACCACCACCAGCACTGACCATCTTCCTGGACCGGCACCCAATCGCACACCTG
CTGTGCTACCCGGCAGCACGCTACCTGATGGGCTCCATGACACCACAAGCCGTGCTGGCCTTCGTGG
CCCTGATCCCACCAACACTGCCCGGCACCAACATCGTGCTGGGCGCCCTGCCCGAGGACCGCCACAT
CGACCGCCTGGCCAAGCGCCAGCGCCCCGGCGAGCGCCTGGACCTGGCCATGCTGGCCGCCATCCGC
CGCGTGTACGGCCTGCTGGCCAACACCGTGCGCTACCTGCAGTGCGGCGGCAGCTGGCGCGAGGACT
GGGGCCAGCTGAGCGGCACCGCCGTGCCACCACAGGGCGCCGAGCCACAGAGCAACGCCGGACCACG
ACCACACATCGGCGACACCCTGTTCACCCTGTTCCGGGCACCAGAGCTGCTGGCACCAAACGGCGAC
CTGTACAACGTGTTCGCCTGGGCCCTGGACGTGCTGGCCAAGCGCCTGCGCTCCATGCACGTGTTCA
TCCTGGACTACGACCAGTCACCGGCCGGCTGCCGCGACGCCCTGCTGCAGCTGACCAGCGGCATGGT
GCAGACCCACGTGACAACACCCGGCAGCATCCCAACAATCTGCGACCTGGCCCGCACCTTCGCCCGC
GAGATGGGCGAGGCCAACTAATAGGGATCCCTCGAGAAGCTTGTCA SEQ ID NO: 16 Gene #1 HSV-TK A168H dmNLS CO SC: Length: 1185
GTCAGCGGCCGCACCGGTACGCGTCCACCATGGCCAGCTACCCCGGCCACCAGCACGCCAGCGCCTT
CGACCAGGCCGCCCGCAGCCGCGGCCACAGCAACGGCAGCACCGCACTGCGGCCAGGATCTCAGCAG
GAGGCCACCGAGGTGCGCCCCGAGCAGAAGATGCCCACCCTGCTGCGCGTGTACATCGACGGACCAC
ACGGCATGGGCAAGACCACCACCACCCAGCTGCTGGTGGCCCTGGGCAGCCGCGACGACATCGTGTA
CGTGCCCGAGCCCATGACCTACTGGCGCGTGCTGGGCGCCAGCGAGACCATCGCCAACATCTACACC
ACCCAGCACCGCCTGGACCAAGGCGAGATCAGCGCCGGCGACGCCCGCCGTGGTGATGACCAGCGCCC
AGATTACAATGGGCATGCCCTACGCCGTGACCGACGCCGTGCTGGCACCACACATCGGCGGCGAGGC
CGGCAGCAGCCACGCACCACCACCAGCACTGACCCTGATCTTCGACCGGCACCCAATCGCACACCTG
CTGTGCTACCCGGCAGCACGCTACCTGATGGGCTCCATGACACCACAAGCCGTGCTGGCCTTCGTGG
CCCTGATCCCACCAACACTGCCCGGCACCAACATCGTGCTGGGCGCCCTGCCCGAGGACCGCCACAT
CGACCGCCTGGCCAAGCGCCAGCGCCCCGGCGAGCGCCTGGACCTGGCCATGCTGGCCGCCATCCGC
CGCGTGTACGGCCTGCTGGCCAACACCGTGCGCTACCTGCAGTGCGGCGGCAGCTGGCGCGAGGACT
GGGGCCAGCTGAGCGGCACCGCCGTGCCACCACAGGGCGCCGAGCCACAGAGCAACGCCGGACCACG
ACCACACATCGGCGACACCCTGTTCACCCTGTTCCGGGCACCAGAGCTGCTGGCACCAAACGGCGAC
CTGTACAACGTGTTCGCCTGGGCCCTGGACGTGCTGGCCAAGCGCCTGCGCTCCATGCACGTGTTCA
TCCTGGACTACGACCAGTCACCGGCCGGCTGCCGCGACGCCCTGCTGCAGCTGACCAGCGGCATGGT
GCAGACCCACGTGACAACACCCGGCAGCATCCCAACAATCTGCGACCTGGCCCGCACCTTCGCCCGC
GAGATGGGCGAGGCCAACTAATAGGGATCCCTCGAGAAGCTTGTCA SEQ ID NO: 17 Gene #2 HSV-TK A167F dmNLS CO SC: Length: 1185
GTCAGCGGCCGCACCGGTACGCGTCCACCATGGCCAGCTACCCCGGCCACCAGCACGCCAGCGCCTT
CGACCAGGCCGCCCGCAGCCGCGGCCACAGCAACGGCAGCACCGCACTGCGGCCAGGATCTCAGCAG
GAGGCCACCGAGGTGCGCCCCGAGCAGAAGATGCCCACCCTGCTGCGCGTGTACATCGACGGACCAC
ACGGCATGGGCAAGACCACCACCACCCAGCTGCTGGTGGCCCTGGGCAGCCGCGACGACATCGTGTA
CGTGCCCGAGCCCATGACCTACTGGCGCGTGCTGGGCGCCAGCGAGACCATCGCCAACATCTACACC
ACCCAGCACCGCCTGGACCAAGGCGAGATCAGCGCCGGCGACGCCCGCCGTGGTGATGACCAGCGCCC
AGATTACAATGGGCATGCCCTACGCCGTGACCGACGCCGTGCTGGCACCACACATCGGCGGCGAGGC
CGGCAGCAGCCACGCACCACCACCAGCACTGACCCTGATCTTCGACCGGCACCCAATCTTCGCACTG
CTGTGCTACCCGGCAGCACGCTACCTGATGGGCTCCATGACACCACAAGCCGTGCTGGCCTTCGTGG
CCCTGATCCCACCAACACTGCCCGGCACCAACATCGTGCTGGGCGCCCTGCCCGAGGACCGCCACAT
CGACCGCCTGGCCAAGCGCCAGCGCCCCGGCGAGCGCCTGGACCTGGCCATGCTGGCCGCCATCCGC
CGCGTGTACGGCCTGCTGGCCAACACCGTGCGCTACCTGCAGTGCGGCGGCAGCTGGCGCGAGGACT
GGGGCCAGCTGAGCGGCACCGCCGTGCCACCACAGGGCGCCGAGCCACAGAGCAACGCCGGACCACG
ACCACACATCGGCGACACCCTGTTCACCCTGTTCCGGGCACCAGAGCTGCTGGCACCAAACGGCGAC
CTGTACAACGTGTTCGCCTGGGCCCTGGACGTGCTGGCCAAGCGCCTGCGCTCCATGCACGTGTTCA
TCCTGGACTACGACCAGTCACCGGCCGGCTGCCGCGACGCCCTGCTGCAGCTGACCAGCGGCATGGT
GCAGACCCACGTGACAACACCCGGCAGCATCCCAACAATCTGCGACCTGGCCCGCACCTTCGCCCGC
GAGATGGGCGAGGCCAACTAATAGGGATCCCTCGAGAAGCTTGTCA SEQ ID NO: 18 Gene #3 HSV-TK A168H NESdmNLS CO SC: Length: 1221
GTCAGCGGCCGCACCGGTACGCGTCCACCATGGGCCCTGCAGAAAAGCTGGAAGAGCTGGAACTGGA
TGGCAGCTACCCCGGCCACCAGCACGCCAGCGCCTTCGACCAGGCCGCCCGCAGCCGCGGCCACAGC
AACGGCAGCACCGCACTGCGGCCAGGATCTCAGCAGGAGGCCACCGAGGTGCGCCCCGAGCAGAAGA
TGCCCACCCTGCTGCGCGTGTACATCGACGGACCACACGGCATGGGCAAGACCACCACCACCCAGCT
GCTGGTGGCCCTGGGCAGCCGCGACGACATCGTGTACGTGCCCGAGCCCATGACCTACTGGCGCGTG

| SEQUENCES |
|---|
| CTGGGCGCCAGCGAGACCATCGCCAACATCTACACCACCCAGCACCGCCTGGACCAAGGCGAGATCA
GCGCCGGCGACGCCGCCGTGGTGATGACCAGCGCCCAGATTACAATGGGCATGCCCTACGCCGTGAC
CGACGCCGTGCTGGCCACCACACATCGGCGGCGAGGCCGGCAGCAGCCACGCACCACCAGCACTG
ACCCTGATCTTCGACCGGCACCCAATCGCACACCTGCTGTGCTACCCGGCAGCACGCTACCTGATGG
GCTCCATGACACCACAAGCCGTGCTGGCCTTCGTGGCCCTGATCCCACCAACACTGCCCGGCACCAA
CATCGTGCTGGGCGCCCTGCCCGAGGACCGCCACATCGACCGCCTGGCCAAGCGCCAGCGCCCCGGC
GAGCGCCTGGACCTGGCCATGCTGGCCGCCATCCGCCGCGTGTACGGCCTGCTGGCCAACACCGTGC
GCTACCTGCAGTGCGGCGGCAGCTGGCGCGAGGACTGGGGCCAGCTGAGCGGCACCGCCGTGCCACC
ACAGGGCGCCGAGCCACAGAGCAACGCCGGACCACGACCACACATCGGCGACACCCTGTTCACCCTG
TTCCGGGCACCAGAGCTGCTGGCACCAAACGGCGACCTGTACAACGTGTTCGCCTGGGCCCTGGACG
TGCTGGCCAAGCGCCTGCGCTCCATGCACGTGTTCATCCTGGACTACGACCAGTCACCGGCCGGCTG
CCGCGACGCCCTGCTGCAGCTGACCAGCGGCATGGTGCAGACCCACGTGACAACACCCGGCAGCATC
CCAACAATCTGCGACCTGGCCCGCACCTTCGCCCGCGAGATGGGCGAGGCCAACTAATAGGGATCCC
TCGAGAAGCTTGTCA

SEQ ID NO: 19 Gene #4 HSV-TK A167F NESdmNLS CO SC: Length: 1221
GTCAGCGGCCGCACCGGTACGCGTCCACCATGGCCCTGCAGAAAAAGCTGGAAGAGCTGGAACTGGA
TGGCAGCTACCCCGGCCACCAGCACGCCAGCGCCTTCGACCAGGCCGCCCGCAGCCGCGGCCACAGC
AACGGCAGCACCGCACTGCGGCCAGGATCTCAGCAGGAGGCCACCGAGGTGCGCCCCGAGCAGAAGA
TGCCCACCCTGCTGCGCGTGTACATCGACGGACCACACGGCATGGGCAAGACCACCACCAGCTG
GCTGGTGGCCCTGGGCAGCCGCGACGACATCGTGTACGTGCCCGAGCCCATGACCTACTGGCGCGTG
CTGGGCGCCAGCGAGACCATCGCCAACATCTACACCACCCAGCACCGCCTGGACCAAGGCGAGATCA
GCGCCGGCGACGCCGCCGTGGTGATGACCAGCGCCCAGATTACAATGGGCATGCCCTACGCCGTGAC
CGACGCCGTGCTGGCCACCACACATCGGCGGCGAGGCCGGCAGCAGCCACGCACCACCAGCACTG
ACCCTGATCTTCGACCGGCACCCAATCTTCGCACTGCTGTGCTACCCGGCAGCACGCTACCTGATGG
GCTCCATGACACCACAAGCCGTGCTGGCCTTCGTGGCCCTGATCCCACCAACACTGCCCGGCACCAA
CATCGTGCTGGGCGCCCTGCCCGAGGACCGCCACATCGACCGCCTGGCCAAGCGCCAGCGCCCCGGC
GAGCGCCTGGACCTGGCCATGCTGGCCGCCATCCGCCGCGTGTACGGCCTGCTGGCCAACACCGTGC
GCTACCTGCAGTGCGGCGGCAGCTGGCGCGAGGACTGGGGCCAGCTGAGCGGCACCGCCGTGCCACC
ACAGGGCGCCGAGCCACAGAGCAACGCCGGACCACGACCACACATCGGCGACACCCTGTTCACCCTG
TTCCGGGCACCAGAGCTGCTGGCACCAAACGGCGACCTGTACAACGTGTTCGCCTGGGCCCTGGACG
TGCTGGCCAAGCGCCTGCGCTCCATGCACGTGTTCATCCTGGACTACGACCAGTCACCGGCCGGCTG
CCGCGACGCCCTGCTGCAGCTGACCAGCGGCATGGTGCAGACCCACGTGACAACACCCGGCAGCATC
CCAACAATCTGCGACCTGGCCCGCACCTTCGCCCGCGAGATGGGCGAGGCCAACTAATAGGGATCCC
TCGAGAAGCTTGTCA SEQ ID NO: 20 Gene #5 HSV-TK A168H NESdmNLS JCO SC: Length: 1221
GTCAGCGGCCGCACCGGTACGCGTCCACCATGGCTCTGCAGAAAAAGCTGGAAGAGCTGGAACTGGA
TGGCTCTTATCCTGGACATCAGCATGCTTCTGCTTTTGATCAGGCTGCCAGATCTAGAGGACATTCT
AATGGCAGCACAGCACTGCGGCCAGGATCTCAGCAGGAAGCTACAGAAGTGAGACCTGAACAGAAAA
TGCCTACACTGCTGAGAGTGTATATTGATGGACCACATGGAATGGGAAAAACAACCACAACCCAGCT
GCTGGTGGCTCTCGGATCTAGAGATGATATTGTGTATGTGCCTGAACCTATGACATATTGGAGAGTG
CTGGGAGCTTCTGAAACAATTGCTAATATCTATACAACACAGCATAGACTGGATCAAGGAGAAATTT
CTGCCGGAGATGCTGCCGTGGTGATGACATCTGCTCAGATTACAATGGGAATGCCTTATGCTGTGAC
AGATGCTGTGCTGGCCACCACATATTGGAGGCGAAGCTGGAAGCTCTCATGCACCACCACCAGCACTG
ACACTGATTTTTGATCGGCATCCAATTGCACATCTGCTGTGTTATCCGGCAGCAAGATATCTGATGG
GAAGCATGACACCACAAGCCGTGCTGGCTTTTGTGGCTCTGATTCCACCAACACTGCCTGGAACAAA
CATCGTGCTGGGAGCTCTGCCTGAAGATAGACATATCGATCGGCTGGCCAAACGGCAGAGACCTGGA
GAACGGCTGGATCTGGCCATGCTGGCTGCCATTCGGAGAGTGTATGCCTGCTGGCTAACACAGTGA
GATATCTGCAGTGTGGAGGCTCTTGGAGAGAGGATTGGGGACAGCTGTCTGGCACAGCTGTGCCACC
ACAGGGAGCCGAACCACAGAGCAATGCTGGACCACGACCACATATCGGAGACACACTGTTTACACTG
TTTCGGGCACCAGAACTGCTGGCACCAAATGGAGACCTGTACAACGTGTTTGCCTGGGCTCTGGATG
TGCTGGCTAAACGGCTGAGATCTATGCATGTGTTTATCCTGGACTATGATCAGTCACCGGCCGGATG
TCGCGATGCCCTGCTGCAGCTGACATCTGGGATGGTGCAGACACATGTGACAACACCTGGATCTATC
CCAACAATCTGTGATCTGGCTAGAACATTCGCTAGGGAGATGGGAGAGGCCAACTAATGAGGATCCC
TCGAGAAGCTTGTCA SEQ ID NO: 21 Gene #6 HSV-TK A167F NESdmNLS JCO SC: Length: 1221
GTCAGCGGCCGCACCGGTACGCGTCCACCATGGCTCTGCAGAAAAAGCTGGAAGAGCTGGAACTGGA
TGGCTCTTATCCTGGACATCAGCATGCTTCTGCTTTTGATCAGGCTGCCAGATCTAGAGGACATTCT
AATGGCAGCACAGCACTGCGGCCAGGATCTCAGCAGGAAGCTACAGAAGTGAGACCTGAACAGAAAA
TGCCTACACTGCTGAGAGTGTATATTGATGGACCACATGGAATGGGAAAAACAACCACAACCCAGCT
GCTGGTGGCTCTCGGATCTAGAGATGATATTGTGTATGTGCCTGAACCTATGACATATTGGAGAGTG
CTGGGAGCTTCTGAAACAATTGCTAATATCTATACAACACAGCATAGACTGGATCAAGGAGAAATTT
CTGCCGGAGATGCTGCCGTGGTGATGACATCTGCTCAGATTACAATGGGAATGCCTTATGCTGTGAC
AGATGCTGTGCTGGCCACCACATATTGGAGGCGAAGCTGGAAGCTCTCATGCACCACCACCAGCACTG
ACACTGATTTTTGATCGGCATCCAATTTTCGCACTGCTGTGTTATCCGGCAGCAAGATATCTGATGG
GAAGCATGACACCACAAGCCGTGCTGGCTTTTGTGGCTCTGATTCCACCAACACTGCCTGGAACAAA
CATCGTGCTGGGAGCTCTGCCTGAAGATAGACATATCGATCGGCTGGCCAAACGGCAGAGACCTGGA
GAACGGCTGGATCTGGCCATGCTGGCTGCCATTCGGAGAGTGTATGCCTGCTGGCTAACACAGTGA
GATATCTGCAGTGTGGAGGCTCTTGGAGAGAGGATTGGGGACAGCTGTCTGGCACAGCTGTGCCACC
ACAGGGAGCCGAACCACAGAGCAATGCTGGACCACGACCACATATCGGAGACACACTGTTTACACTG
TTTCGGGCACCAGAACTGCTGGCACCAAATGGAGACCTGTACAACGTGTTTGCCTGGGCTCTGGATG
TGCTGGCTAAACGGCTGAGATCTATGCATGTGTTTATCCTGGACTATGATCAGTCACCGGCCGGATG
TCGCGATGCCCTGCTGCAGCTGACATCTGGGATGGTGCAGACACATGTGACAACACCTGGATCTATC
CCAACAATCTGTGATCTGGCTAGAACATTCGCTAGGGAGATGGGAGAGGCCAACTAATGAGGATCCC
TCGAGAAGCTTGTCA |

SEQUENCES

SEQ ID NO: 22 HSV-TK dmNLS A168H, CO & SC
dmNLS = double mutated Nuclear Localization Sequence
CO = codon optimized
SC = splice corrected at 327 and 555
Kozak Sequence, Underlined

```
gtcaGCGGCCGCACCGGTACGCGTCCACCATGGCCAGCTACCCCGGCCACCAGCACGCCAGCGCCTT
CGACCAGGCCGCCCGCAGCCGCGGCCACAGCAACGGCAGCACCGCaCTGCGgCCaGGATCTCAGCAG
GAGGCCACCGAGGTGCGCCCCGAGCAGAAGATGCCCACCCTGCTGCGCGTGTACATCGACGGaCCaC
ACGGCATGGGCAAGACCACCACCACCCAGCTGCTGGTGGCCCTGGGCAGCCGCGACGACATCGTGTA
CGTGCCCGAGCCCATGACCTACTGGCGCGTGCTGGGCGCCAGCGAGACCATCGCCAACATCTACACC
ACCCAGCACCGCCTGGACCAaGGCGAGATCAGCGCCGGCGACGCCGCCGTGGTGATGACCAGCGCCC
AGATTAaCaATGGGCATGCCCTACGCCGTGACCGACGCCGTGCTGGCaCCaCACATCGGCGGCGAGGC
CGGCAGCAGCCACGCaCCaCCaCCaGCaCTGACCCTGATCTTCGACCGgCACCCaATCGCaCACCTG
CTGTGCTACCCgGCaGCaCGCTACCTGATGGGCtccATGCaCCaCAaGCCGTGCTGGCCTTCGTGG
CCCTGATCCCaCCaCaCTGCCCGGCACCAACATCGTGCTGGGCGCCCTGCCCGAGGACCGCCACAT
CGACCGCCTGGCCAAGCGCCAGCGCCCCGGCGAGCGCCTGGACCTGGCCATGCTGGCCGCCATCCGC
CGCGTGTACGGCCTGCTGGCCAACACCGTGCGCTACCTGCAGTGCGGCGGCAGCTGGCGCGAGGACT
GGGGCCAGCTGAGCGGCACCGCCGTGCCaCCaCAGGGCGCCGAGCCaCAGAGCAACGCCGGaCCaCG
aCCaCACATCGGCGACACCCTGTTCACCCTGTTCCGgGCaCCaGAGCTGCTGGCaCCaAACGGCGAC
CTGTACAACGTGTTCGCCTGGGCCCTGGACGTGCTGGCCAAGCGCCTGCGCtccATGCACGTGTTCA
TCCTGGACTACGACCAGtcaCCgGCCGGCTGCCGCGACGCCCTGCTGCAGCTGACCAGCGGCATGGT
GCAGACCCACGTGACaAaCCCGGCAGCATCCCaACaATCTGCGACCTGGCCCGCACCTTCGCCCGC
GAGATGGGCGAGGCCAACTAATAGGGATCCCTCGAGAAGCTTgtca
```

SEQ ID NO: 23-MAP Kinase Kinase Nuclear Export Polynucleotide Sequence
CTGCAGAAAAAGCTGGAAGAGCTGGAACTGGATGGC SEQ ID NO: 24-MAP Kinase Kinase Nuclear Export Polypeptide Sequence
LQKKLEELELDG SEQ ID NO: 25-Targeting Moiety
WREPSFMALS

---

What is claimed is:

1. A method for identifying a patient capable of benefiting from gene therapy treatment for tumor lesions, and treating the patient in need of treatment thereof by decreasing tumor burden in the patient, the method comprising:
   a) administering a sufficient quantity of a first injection or infusion of a gene therapy retroviral vector particle comprising an HSV-thymidine kinase (HSV-TK) polynucleotide comprising a nuclear export sequence to a target tissue in the patient, and transducing cells from the target tissue with the polynucleotide encoding HSV-TK, thereby expressing HSV-TK in the transduced cells, wherein the HSV-TK polynucleotide encodes a mutated form of human HSV-TK comprising mutations at amino acid residues 32 and 33 and at least one of amino acid residues 25, 26, or 168, wherein the amino acid residues correspond to positions 32, 33, 25, 26, and 168 of SEQ ID NO: 2, wherein amino acid residues 32 and 33 are each independently mutated to an amino acid chosen from the group consisting of: glycine, serine, and glutamic acid, and wherein the mutated form of human HSV-TK increases cell kill activity relative to a wild-type thymidine kinase;

b) administering to said patient a substrate of HSV-TK attached to a radioactive tracer;

c) measuring the relative amount of radioactive tracer signal present in the target tissue;

d) identifying if the level of radioactive tracer signal is above a certain threshold;

e) determining the location of tumor lesions in the patient to determine whether the tumor lesion co-localizes with the measured radioactive tracer signal in step (c); and f) administering said patient with a second injection or infusion of the gene therapy retroviral vector particle comprising the HSV-TK polynucleotide comprising the nuclear export sequence of step a) and a substrate of HSV-TK that is not attached to a radioactive tracer for treatment if (i) the measured radioactive tracer signal of step (c) in the patient is above the certain threshold, and (ii) the location of the measured radioactive signal co-localizes with tumor lesions as in step (e);

wherein the gene therapy retroviral vector particle is administered systemically, and wherein the administering of step f) treats the patient in need thereof.

2. The method of claim 1, wherein the substrate of HSV-TK is chosen from the group consisting of FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpyrimidine-2,4(1H,3H)-dione), ganciclovir, valganciclovir, acyclovir, valacyclovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-, ganciclovir- and penciclovir-like side chains.

3. The method of claim 1, wherein the substrate of HSV-TK is FHBG (9-[4-fluoro-3-(hydroxymethyl)butyl]guanine).

4. The method of claim 1, wherein the radioactive tracer is $^{18}$F, $^{64}$Cu, $^{99m}$Tc, $^{11}$C, $^{14}$C, $^{124}$I, $^{123}$I, $^{131}$I, $^{15}$O, $^{13}$N and/or $^{82}$RbCl.

5. The method of claim 1, wherein the radioactive tracer is $^{18}$F.

6. The method of claim 1, wherein the HSV-TK substrate attached to a radioactive tracer is [$^{18}$F]FHBG (9-(4-$^{18}$F-fluoro-3-(hydroxymethyl)butyl]guanine).

7. The method of claim 1, wherein the radioactive tracer signal is measured using positron emission tomography (PET) scanning.

8. The method of claim 7, wherein the threshold level is at least above 2.0 SUV (standardized uptake value) or at least 20% above background on a PET scan.

9. The method of claim 7, wherein the threshold level is between about 1.0 SUV and about 3.0 SUV.

10. The method of claim 8 or 9, wherein the HSV-TK retroviral particle comprises a second therapeutic polynucleotide.

11. The method of claim 1, wherein the viral nuclear localization sequence (NLS) of the encoded HSV-TK polynucleotide is mutated.

12. The method of claim 1, wherein the HSV-TK polynucleotide comprises the nuclear export sequence (NES) at or near the amino terminus of the expressed human HSV-TK protein.

13. The method of claim 1, wherein the HSV-TK polynucleotide is mutated to increase substrate binding of the expressed human HSV-TK protein.

14. The method of claim 13, wherein the mutation is A168H.

15. The method of claim 13, further comprising mutating the HSV-TK polynucleotide to remove the viral nuclear localization sequence (NLS).

16. The method of claim 1, wherein the HSV-TK polynucleotide is SEQ ID NO: 18.

17. The method of claim 16, wherein the gene therapy retroviral vector particle further comprises a polynucleotide encoding for a targeting protein expressed on the viral envelope.

18. The method of claim 17, wherein the targeting protein binds to collagen, laminin, fibronectin, elastin, glycosaminoglycans, proteoglycans or RGD.

19. The method of claim 17, wherein the targeting protein binds to collagen.

20. The method of claim 19, wherein the targeting protein is SEQ ID NO: 25.

21. The method of claim 1, wherein the HSV-TK polynucleotide encodes a mutated form of human HSV-TK comprising mutations at amino acid residues 32 and 33 and at least one of amino acid residues 25 or 26, wherein the amino acid residues correspond to positions 32, 33, 25, and 26 of SEQ ID NO: 2.

22. The method of claim 1, wherein the HSV-TK polynucleotide encodes a mutated form of human HSV-TK comprising mutations at amino acid residues 32, 33 and 168, wherein the amino acid residues correspond to positions 32, 33, and 168 of SEQ ID NO: 2.

23. The method of claim 1, wherein amino acid residues 25 and 26 are mutated to an amino acid chosen from the group consisting of: glycine, serine, and glutamic acid.

24. The method of claim 1, wherein amino acid residue 168 is mutated to an amino acid selected from the group consisting of: histidine, lysine, cysteine, serine, and phenylalanine.

* * * * *

SEQUENCE LISTING

<160> NUMBER OF SEQ ID NOS: 25

<210> SEQ ID NO 1
<211> LENGTH: 1131
<212> TYPE: DNA
<213> ORGANISM: Herpes simplex virus 1

<400> SEQUENCE: 1

```
atggcttcgt accccggcca tcaacacgcg tctgcgttcg accaggctgc gcgttctcgc      60
ggccatagca accgacgtac ggcgttgcgc cctcgccggc agcaagaagc cacggaagtc     120 cgccccggagc agaaaatgcc cacgctactg cgggtttata tagacggtcc ccacgggatg    180
gggaaaacca ccaccacgca actgctggtg gccctgggtt cgcgcgacga tatcgtctac     240
gtacccgagc cgatgactta ctggcgggtg ctgggggctt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg gggggaggc tgggagctca catgccccgc cccggccct caccctcatc      480 ttcgaccgcc atcccatcgc cgccctcctg tgctacccgg ccgcgcggta ccttatgggc     540
agcatgaccc cccaggccgt gctggcgttc gtggccctca tcccgccgac cttgcccggc     600
accaacatcg tgcttgggggc ccttccggag acagacaca tcgaccgcct ggccaaacgc     660
cagcgccccg gcgagcggct ggacctggct atgctggctg cgattcgccg cgtttacggg     720
ctacttgcca atacggtgcg gtatctgcag tgcggcgggt cgtggcggga ggactgggga     780
cagctttcgg ggacggccgt gccgccccag ggtgccgagc cccagagcaa cgcgggccca     840
```

```
cgaccccata tcggggacac gttatttacc ctgtttcggg cccccgagtt gctggccccc      900
aacggcgacc tgtataacgt gtttgcctgg gccttggacg tcttggccaa acgcctccgt      960
tccatgcacg tctttatcct ggattacgac caatcgcccg ccggctgccg ggacgccctg     1020
ctgcaactta cctccgggat ggtccagacc cacgtcacca cccccggctc cataccgacg     1080
atatgcgacc tggcgcgcac gtttgcccgg gagatggggg aggctaactg a             1131
```

<210> SEQ ID NO 2
<211> LENGTH: 376
<212> TYPE: PRT
<213> ORGANISM: Herpes simplex virus 1

<400> SEQUENCE: 2

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Pro Glu Gln Lys Met Pro Thr
            35                  40                  45

Leu Leu Arg Val Tyr Ile Asp Gly Pro His Gly Met Gly Lys Thr Thr
        50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
```

```
                325                 330                 335

Arg Asp Ala Leu Leu Gln Leu Thr Ser Gly Met Val Gln Thr His Val
        340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
        370                 375

<210> SEQ ID NO 3
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggcctcgt accccggcca tcaacacgcg tctgcgttcg accaggctgc gcgttctcgc      60
ggccatagca acggatccac ggcgttgcgc cctcgccggc agcaagaagc cacggaagtc     120
cgcccggagc agaaaatgcc cacgctactg cgggtttata tagacggtcc ccacgggatg     180
gggaaaacca ccaccacgca actgctggtg gccctgggtt cgcgcgacga tatcgtctac     240
gtacccgagc cgatgactta ctggcgggtg ctgggggctt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg gggggaggc tgggagctca catgccccgc cccggccct caccatcttc       480 ctcgaccgcc atcccatcgc cttcatgctg tgctacccgg ccgcgcggta ccttatgggc     540
agcatgaccc ccaggccgt gctggcgttc gtggccctca tcccgccgac cttgcccggc     600
accaacatcg tgcttggggc ccttccggag acagacaca tcgaccgcct ggccaaacgc      660
cagcgccccg cgagcggct ggacctggct atgctggctg cgattcgccg cgtttacggg      720
ctacttgcca atacggtgcg gtatctgcag tgcggcgggt cgtggcggga ggactgggga     780
cagctttcgg ggacggccgt gccgccccag ggtgccgagc ccagagcaa cgcgggccca      840 cgacccata tcgggacac gttatttacc ctgtttcggg ccccgagtt gctggccccc       900 aacggcgacc tgtataacgt gtttgcctgg gccttgacg tcttggccaa cgcctccgt      960 tccatgcacg tctttatcct ggattacgac caatcgcccg ccggctgccg ggacgccctg    1020
ctgcaactta cctccgggat ggtccagacc cacgtcacca ccccggctc ataccgacg      1080 atatgcgacc tggcgcgcac gtttgcccgg gagatggggg aggctaactg a             1131

<210> SEQ ID NO 4
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Ser Tyr Pro Gly His Gln His Ala Ser Ala Phe Asp Gln Ala
1               5                   10                  15

Ala Arg Ser Arg Gly His Ser Asn Gly Ser Thr Ala Leu Arg Pro Arg
            20                  25                  30

Arg Gln Gln Glu Ala Thr Glu Val Arg Pro Glu Gln Lys Met Pro Thr
        35                  40                  45
```

Leu Leu Arg Val Tyr Ile Asp Gly Pro His Gly Met Gly Lys Thr Thr
 50                  55                  60

Thr Thr Gln Leu Leu Val Ala Leu Gly Ser Arg Asp Asp Ile Val Tyr
 65                  70                  75                  80

Val Pro Glu Pro Met Thr Tyr Trp Arg Val Leu Gly Ala Ser Glu Thr
                 85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
130                 135                 140

Gly Glu Ala Gly Ser Ser His Ala Pro Pro Ala Leu Thr Ile Phe
145                 150                 155                 160

Leu Asp Arg His Pro Ile Ala Phe Met Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
                195                 200                 205

Pro Glu Asp Arg His Ile Asp Arg Leu Ala Lys Arg Gln Arg Pro Gly
            210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
                260                 265                 270

Glu Pro Gln Ser Asn Ala Gly Pro Arg Pro His Ile Gly Asp Thr Leu
            275                 280                 285

Phe Thr Leu Phe Arg Ala Pro Glu Leu Leu Ala Pro Asn Gly Asp Leu
290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
                340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
370                 375

<210> SEQ ID NO 5
<211> LENGTH: 1131
<212> TYPE: DNA
<213> ORGANISM: Herpes simplex virus 1
<220> FEATURE:
<221> NAME/KEY: CDS
<222> LOCATION: (1)..(1128)

<400> SEQUENCE: 5 atg gcc tcg tac ccc ggc cat caa cac gcg tct gcg ttc gac cag gct    48
Met Ala Ser Tyr Pro Gly His Gln His Ala Ser Ala Phe Asp Gln Ala
 1               5                  10                  15

```
gcg cgt tct cgc ggc cat agc aac cga cgt acg gcg ttg cgc cct cgc      96
Ala Arg Ser Arg Gly His Ser Asn Arg Arg Thr Ala Leu Arg Pro Arg
         20                  25                  30 cgg cag caa gaa gcc acg gaa gtc cgc ccg gag cag aaa atg ccc acg     144
Arg Gln Gln Glu Ala Thr Glu Val Arg Pro Glu Gln Lys Met Pro Thr
     35                  40                  45 cta ctg cgg gtt tat ata gac ggt ccc cac ggg atg ggg aaa acc acc     192
Leu Leu Arg Val Tyr Ile Asp Gly Pro His Gly Met Gly Lys Thr Thr
 50                  55                  60 acc acg caa ctg ctg gtg gcc ctg ggt tcg cgc gac gat atc gtc tac     240
Thr Thr Gln Leu Leu Val Ala Leu Gly Ser Arg Asp Asp Ile Val Tyr
65                  70                  75                  80 gta ccc gag ccg atg act tac tgg cgg gtg ctg ggg gct tcc gag aca     288
Val Pro Glu Pro Met Thr Tyr Trp Arg Val Leu Gly Ala Ser Glu Thr
                 85                  90                  95 atc gcg aac atc tac acc aca caa cac cgc ctc gac cag ggt gag ata     336
Ile Ala Asn Ile Tyr Thr Thr Gln His Arg Leu Asp Gln Gly Glu Ile
             100                 105                 110 tcg gcc ggg gac gcg gcg gtg gta atg aca agc gcc cag ata aca atg     384
Ser Ala Gly Asp Ala Ala Val Val Met Thr Ser Ala Gln Ile Thr Met
         115                 120                 125 ggc atg cct tat gcc gtg acc gac gcc gtt ctg gct cct cat atc ggg     432
Gly Met Pro Tyr Ala Val Thr Asp Ala Val Leu Ala Pro His Ile Gly
     130                 135                 140 ggg gag gct ggg agc tca cat gcc ccg ccc ccg gcc ctc acc ctc atc     480
Gly Glu Ala Gly Ser Ser His Ala Pro Pro Pro Ala Leu Thr Leu Ile
145                 150                 155                 160 ttc gac cgc cat ccc atc gcc gcc ctc ctg tgc tac ccg gcc gcg cgg     528
Phe Asp Arg His Pro Ile Ala Ala Leu Leu Cys Tyr Pro Ala Ala Arg
                 165                 170                 175 tac ctt atg ggc agc atg acc ccc cag gcc gtg ctg gcg ttc gtg gcc     576
Tyr Leu Met Gly Ser Met Thr Pro Gln Ala Val Leu Ala Phe Val Ala
             180                 185                 190 ctc atc ccg ccg acc ttg ccc ggc acc aac atc gtg ctt ggg gcc ctt     624
Leu Ile Pro Pro Thr Leu Pro Gly Thr Asn Ile Val Leu Gly Ala Leu
         195                 200                 205 ccg gag gac aga cac atc gac cgc ctg gcc aaa cgc cag cgc ccc ggc     672
Pro Glu Asp Arg His Ile Asp Arg Leu Ala Lys Arg Gln Arg Pro Gly
     210                 215                 220 gag cgg ctg gac ctg gct atg ctg gct gcg att cgc cgc gtt tac ggg     720
Glu Arg Leu Asp Leu Ala Met Leu Ala Ala Ile Arg Arg Val Tyr Gly
225                 230                 235                 240 cta ctt gcc aat acg gtg cgg tat ctg cag tgc ggc ggg tcg tgg cgg     768
Leu Leu Ala Asn Thr Val Arg Tyr Leu Gln Cys Gly Gly Ser Trp Arg
                 245                 250                 255 gag gac tgg gga cag ctt tcg ggg acg gcc gtg ccg ccc cag ggt gcc     816
Glu Asp Trp Gly Gln Leu Ser Gly Thr Ala Val Pro Pro Gln Gly Ala
             260                 265                 270 gag ccc cag agc aac gcg ggc cca cga ccc cat atc ggg gac acg tta     864
Glu Pro Gln Ser Asn Ala Gly Pro Arg Pro His Ile Gly Asp Thr Leu
         275                 280                 285 ttt acc ctg ttt cgg gcc ccc gag ttg ctg gcc ccc aac ggc gac ctg     912
Phe Thr Leu Phe Arg Ala Pro Glu Leu Leu Ala Pro Asn Gly Asp Leu
     290                 295                 300 tat aac gtg ttt gcc tgg gcc ttg gac gtc ttg gcc aaa cgc ctc cgt     960
Tyr Asn Val Phe Ala Trp Ala Leu Asp Val Leu Ala Lys Arg Leu Arg
305                 310                 315                 320 tcc atg cac gtc ttt atc ctg gat tac gac caa tcg ccc gcc ggc tgc    1008
Ser Met His Val Phe Ile Leu Asp Tyr Asp Gln Ser Pro Ala Gly Cys
                 325                 330                 335
```

```
cgg gac gcc ctg ctg caa ctt acc tcc ggg atg gtc cag acc cac gtc    1056
Arg Asp Ala Leu Leu Gln Leu Thr Ser Gly Met Val Gln Thr His Val
        340                 345                 350 acc acc ccc ggc tcc ata ccg acg ata tgc gac ctg gcg cgc acg ttt    1104
Thr Thr Pro Gly Ser Ile Pro Thr Ile Cys Asp Leu Ala Arg Thr Phe
        355                 360                 365 gcc cgg gag atg ggg gag gct aac tga                                1131
Ala Arg Glu Met Gly Glu Ala Asn
        370             375

<210> SEQ ID NO 6
<211> LENGTH: 89
<212> TYPE: DNA
<213> ORGANISM: Herpes simplex virus 1

<400> SEQUENCE: 6
gagctcacat gccccgcccc cggccctcac catcttcctc gaccgccatc ccatcgcctt    60
catgctgtgc tacccggccg cgcggtacc                                      89

<210> SEQ ID NO 7
<211> LENGTH: 89
<212> TYPE: DNA
<213> ORGANISM: Herpes simplex virus 1

<400> SEQUENCE: 7
ctcgagtgta cggggcgggg gccgggagtg gtagaaggag ctggcggtag ggtagcggaa    60
gtacgacacg atgggccggc gcgccatgg                                      89

<210> SEQ ID NO 8
<211> LENGTH: 83
<212> TYPE: DNA
<213> ORGANISM: Herpes simplex virus 1

<400> SEQUENCE: 8
cacatgcccc gccccggcc ctcaccatct tcctcgaccg ccatcccatc gccttcatgc    60
tgtgctaccc ggccgcgcgg tac                                            83

<210> SEQ ID NO 9
<211> LENGTH: 79
<212> TYPE: DNA
<213> ORGANISM: Herpes simplex virus 1

<400> SEQUENCE: 9
tcgagtgtac ggggcggggg ccgggagtgg tagaaggagc tggcggtagg gtagcggaag    60
tacgacacga tgggccggc                                                 79

<210> SEQ ID NO 10
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cacatgcccc gccccggcc ctcaccatct tcctcgaccg ccatcccatc gccttcatgc    60
tgtgctaccc ggccgcgcgg tac                                            83

<210> SEQ ID NO 11
<211> LENGTH: 83
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgcgcggccg ggtagcacag catgaaggcg atgggatggc ggtcgaggaa gatggtgagg    60
gccgggggcg gggcatgtga gct                                            83

<210> SEQ ID NO 12
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gtcagcggcc gcaccggtac gcgtccacca tggccagcta ccccggccac cagcacgcca    60
gcgccttcga ccaggccgcc cgcagccgcg ccacagcaa cggcagcacc gcactgcggc   120
cacggcgcca gcaggaggcc accgaggtgc gccccgagca gaagatgccc accctgctgc   180
gcgtgtacat cgacggacca cacggcatgg gcaagaccac caccacccag ctgctggtgg   240
ccctgggcag ccgcgacgac atcgtgtacg tgccccgagcc catgacctac tggcgcgtgc   300
tgggcgccag cgagaccatc gccaacatct acaccaccca gcaccgcctg gaccaaggcg   360
agatcagcgc cggcgacgcc gccgtggtga tgaccagcgc ccagattaca atgggcatgc   420
cctacgccgt gaccgacgcc gtgctggcac cacacatcgg cggcgaggcc ggcagcagcc   480
acgcaccacc accagcactg accctgatct tcgaccggca cccaatcgca cacctgctgt   540
gctaccggcc agcacgctac ctgatgggct ccatgacacc acaagccgtg ctggccttcg   600
tggccctgat cccaccaaca ctgccccggca ccaacatcgt gctgggcgcc ctgcccgagg   660
accgccacat cgaccgcctg ccaagcgcc agcgcccccgg cgagcgcctg gacctggcca   720
tgctggccgc catccgccgc gtgtacggcc tgctggccaa caccgtgcgc tacctgcagt   780
gcggcggcag ctggcgcgag gactgggggcc agctgagcgg caccgccgtg ccaccacagg   840
gcgccgagcc acagagcaac gccggaccac gaccacacat cggcgacacc ctgttcaccc   900
tgttccgggc accagagctg ctggcaccaa acggcgacct gtacaacgtg ttcgcctggg   960
ccctggacgt gctggccaag cgcctgcgct ccatgcacgt gttcatcctg gactacgacc  1020
agtcaccggc cggctgccgc gacgccctgc tgcagctgac cagcggcatg gtgcagaccc  1080
acgtgacaac cccggcagc atcccaacaa tctgcgacct ggcccgcacc ttcgcccgcg  1140
agatgggcga ggccaactaa tagggatccc tcgagaagct tgtca                  1185

<210> SEQ ID NO 13
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gtcagcggcc gcaccggtac gcgtccacca tggccagcta ccccggccac cagcacgcca    60
gcgccttcga ccaggccgcc cgcagccgcg ccacagcaa cggcagcacc gcactgcggc   120
cacggcgcca gcaggaggcc accgaggtgc gccccgagca gaagatgccc accctgctgc   180
```

```
gcgtgtacat cgacggacca cacggcatgg gcaagaccac caccacccag ctgctggtgg      240
ccctgggcag ccgcgacgac atcgtgtacg tgcccgagcc catgacctac tggcgcgtgc      300
tgggcgccag cgagaccatc gccaacatct acaccaccca gcaccgcctg gaccaaggcg      360
agatcagcgc cggcgacgcc gccgtggtga tgaccagcgc ccagattaca atgggcatgc      420
cctacgccgt gaccgacgcc gtgctggcac acacatcgg cggcgaggcc ggcagcagcc       480
acgcaccacc accagcactg accctgatct tcgaccggca cccaatcttc gcactgctgt      540 gctaccggc agcacgctac ctgatgggct ccatgacacc acaagccgtg ctggccttcg       600
tggccctgat cccaccaaca ctgcccgca ccaacatcgt gctgggcgcc ctgcccgagg       660
accgccacat cgaccgcctg gccaagcgcc agcgccccgg cgagcgcctg gacctggcca      720
tgctggccgc catccgccgc gtgtacggcc tgctggccaa caccgtgcgc tacctgcagt      780
gcggcggcag ctggcgcgag gactggggcc agctgagcgg caccgccgtg ccaccacagg      840
gcgccgagcc acagagcaac gccggaccac gaccacacat cggcgacacc ctgttcaccc      900
tgttccgggc accagagctg ctggcaccaa acggcgacct gtacaacgtg ttcgcctggg      960
ccctggacgt gctggccaag cgcctgcgct ccatgcacgt gttcatcctg gactacgacc     1020
agtcaccggc cggctgccgc gacgccctgc tgcagctgac cagcggcatg gtgcagaccc     1080
acgtgacaac acccggcagc atcccaacaa tctgcgacct ggcccgcacc ttcgcccgcg     1140
agatgggcga ggccaactaa tagggatccc tcgagaagct tgtca                     1185
```

<210> SEQ ID NO 14
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
gtcagcggcc gcaccggtac gcgtccacca tggccagcta ccccggccac cagcacgcca       60
gcgccttcga ccaggccgcc cgcagccgcg ccacagcaa cggcagcacc gcactgcggc       120
cacggcgcca gcaggaggcc accgaggtgc gccccgagca gaagatgccc accctgctgc      180
gcgtgtacat cgacggacca cacggcatgg gcaagaccac caccacccag ctgctggtgg      240
ccctgggcag ccgcgacgac atcgtgtacg tgcccgagcc catgacctac tggcgcgtgc      300
tgggcgccag cgagaccatc gccaacatct acaccaccca gcaccgcctg gaccaaggcg      360
agatcagcgc cggcgacgcc gccgtggtga tgaccagcgc ccagattaca atgggcatgc      420
cctacgccgt gaccgacgcc gtgctggcac acacatcgg cggcgaggcc ggcagcagcc       480
acgcaccacc accagcactg accctgatct tcgaccggca cccaatcttc cacctgctgt      540 gctaccggc agcacgctac ctgatgggct ccatgacacc acaagccgtg ctggccttcg       600
tggccctgat cccaccaaca ctgcccgca ccaacatcgt gctgggcgcc ctgcccgagg       660
accgccacat cgaccgcctg gccaagcgcc agcgccccgg cgagcgcctg gacctggcca      720
tgctggccgc catccgccgc gtgtacggcc tgctggccaa caccgtgcgc tacctgcagt      780
gcggcggcag ctggcgcgag gactggggcc agctgagcgg caccgccgtg ccaccacagg      840
gcgccgagcc acagagcaac gccggaccac gaccacacat cggcgacacc ctgttcaccc      900
tgttccgggc accagagctg ctggcaccaa acggcgacct gtacaacgtg ttcgcctggg      960
ccctggacgt gctggccaag cgcctgcgct ccatgcacgt gttcatcctg gactacgacc     1020
```
agtcaccggc cggctgccgc gacgccctgc tgcagctgac cagcggcatg gtgcagaccc  1080
acgtgacaac acccggcagc atcccaacaa tctgcgacct ggcccgcacc ttcgcccgcg  1140
agatgggcga ggccaactaa tagggatccc tcgagaagct tgtca  1185

<210> SEQ ID NO 15
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gtcagcggcc gcaccggtac gcgtccacca tggccagcta ccccggccac cagcacgcca   60
gcgccttcga ccaggccgcc cgcagccgcg gccacagcaa cggcagcacc gcactgcggc  120
cacggcgcca gcaggaggcc accgaggtgc gccccgagca agagatgccc accctgctgc  180
gcgtgtacat cgacggacca cacggcatgg gcaagaccac caccacccag ctgctggtgg  240
ccctgggcag ccgcgacgac atcgtgtacg tgcccgagcc catgacctac tggcgcgtgc  300
tgggcgccag cgagaccatc gccaacatct acaccaccca gcaccgcctg gaccaaggcg  360
agatcagcgc cggcgacgcc gccgtggtga tgaccagcgc ccagattaca atgggcatgc  420
cctacgccgt gaccgacgcc gtgctggcac acacatcgg cggcgaggcc ggcagcagcc  480
acgcaccacc accagcactg accatcttcc tggaccggca cccaatcgca cacctgctgt  540 gctaccggc agcacgctac ctgatgggct ccatgacacc acaagccgtg ctggccttcg  600
tggccctgat cccaccaaca ctgcccggca ccaacatcgt gctgggcgcc ctgcccgagg  660
accgccacat cgaccgcctg gccaagcgcc agcgcccegg cgagcgcctg gacctggcca  720
tgctggccgc catccgccgc gtgtacggcc tgctggccaa caccgtgcgc tacctgcagt  780
gcggcggcag ctggcgcgag gactggggcc agctgagcgg caccgccgtg ccaccacagg  840
gcgccgagcc acagagcaac gccggaccac gaccacacat cggcgacacc ctgttcaccc  900
tgttccgggc accagagctg ctggcaccaa acggcgacct gtacaacgtg ttcgcctggg  960
ccctggacgt gctggccaag cgcctgcgct ccatgcacgt gttcatcctg gactacgacc  1020
agtcaccggc cggctgccgc gacgccctgc tgcagctgac cagcggcatg gtgcagaccc  1080
acgtgacaac acccggcagc atcccaacaa tctgcgacct ggcccgcacc ttcgcccgcg  1140
agatgggcga ggccaactaa tagggatccc tcgagaagct tgtca  1185

<210> SEQ ID NO 16
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gtcagcggcc gcaccggtac gcgtccacca tggccagcta ccccggccac cagcacgcca   60
gcgccttcga ccaggccgcc cgcagccgcg gccacagcaa cggcagcacc gcactgcggc  120
caggatctca gcaggaggcc accgaggtgc gccccgagca agagatgccc accctgctgc  180
gcgtgtacat cgacggacca cacggcatgg gcaagaccac caccacccag ctgctggtgg  240
ccctgggcag ccgcgacgac atcgtgtacg tgcccgagcc catgacctac tggcgcgtgc  300

```
tgggcgccag cgagaccatc gccaacatct acaccaccca gcaccgcctg gaccaaggcg      360
agatcagcgc cggcgacgcc gccgtggtga tgaccagcgc ccagattaca atgggcatgc      420
cctacgccgt gaccgacgcc gtgctggcac acacatcgg cggcgaggcc ggcagcagcc       480
acgcaccacc accagcactg accctgatct tcgaccggca cccaatcgca cacctgctgt      540 gctaccggc agcacgctac ctgatgggct ccatgacacc acaagccgtg ctggccttcg       600
tggccctgat cccaccaaca ctgcccggca ccaacatcgt gctgggcgcc ctgcccgagg      660
accgccacat cgaccgcctg gccaagcgcc agcgccccgg cgagcgcctg gacctggcca      720
tgctggccgc catccgccgc gtgtacggcc tgctggccaa caccgtgcgc tacctgcagt      780
gcggcggcag ctggcgcgag gactgggggcc agctgagcgg caccgccgtg ccaccacagg     840
gcgccgagcc acagagcaac gccggaccac gaccacacat cggcgacacc ctgttcaccc     900
tgttccgggc accagagctg ctggcaccaa acggcgacct gtacaacgtg ttcgcctggg     960
ccctggacgt gctggccaag cgcctgcgct ccatgcacgt gttcatcctg gactacgacc     1020
agtcaccggc cggctgccgc gacgccctgc tgcagctgac cagcggcatg gtgcagaccc     1080
acgtgacaac acccggcagc atcccaacaa tctgcgacct ggcccgcacc ttcgcccgcg     1140
agatgggcga ggccaactaa tagggatccc tcgagaagct tgtca                      1185

<210> SEQ ID NO 17
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gtcagcggcc gcaccggtac gcgtccacca tggccagcta ccccggccac cagcacgcca       60
gcgccttcga ccaggccgcc cgcagccgcg ccacagcaa cggcagcacc gcactgcggc       120
caggatctca gcaggaggcc accgaggtgc gccccgagca gaagatgccc accctgctgc      180
gcgtgtacat cgacggacca cacggcatgg gcaagaccac caccacccag ctgctggtgg      240
ccctgggcag ccgcgacgac atcgtgtacg tgcccgagcc catgacctac tggcgcgtgc      300
tgggcgccag cgagaccatc gccaacatct acaccaccca gcaccgcctg gaccaaggcg      360
agatcagcgc cggcgacgcc gccgtggtga tgaccagcgc ccagattaca atgggcatgc      420
cctacgccgt gaccgacgcc gtgctggcac acacatcgg cggcgaggcc ggcagcagcc       480
acgcaccacc accagcactg accctgatct tcgaccggca cccaatcttc gcactgctgt      540 gctaccggc agcacgctac ctgatgggct ccatgacacc acaagccgtg ctggccttcg       600
tggccctgat cccaccaaca ctgcccggca ccaacatcgt gctgggcgcc ctgcccgagg      660
accgccacat cgaccgcctg gccaagcgcc agcgccccgg cgagcgcctg gacctggcca      720
tgctggccgc catccgccgc gtgtacggcc tgctggccaa caccgtgcgc tacctgcagt      780
gcggcggcag ctggcgcgag gactgggggcc agctgagcgg caccgccgtg ccaccacagg     840
gcgccgagcc acagagcaac gccggaccac gaccacacat cggcgacacc ctgttcaccc     900
tgttccgggc accagagctg ctggcaccaa acggcgacct gtacaacgtg ttcgcctggg     960
ccctggacgt gctggccaag cgcctgcgct ccatgcacgt gttcatcctg gactacgacc     1020
agtcaccggc cggctgccgc gacgccctgc tgcagctgac cagcggcatg gtgcagaccc     1080
acgtgacaac acccggcagc atcccaacaa tctgcgacct ggcccgcacc ttcgcccgcg     1140
```
agatgggcga ggccaactaa tagggatccc tcgagaagct tgtca        1185

<210> SEQ ID NO 18
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gtcagcggcc gcaccggtac gcgtccacca tggccctgca gaaaaagctg gaagagctgg        60
aactggatgg cagctacccc ggccaccagc acgccagcgc cttcgaccag gccgcccgca       120
gccgcggcca cagcaacggc agcaccgcac tgcggccagg atctcagcag gaggccaccg       180
aggtgcgccc cgagcagaag atgcccaccc tgctgcgcgt gtacatcgac ggaccacacg       240
gcatgggcaa gaccaccacc acccagctgc tggtggccct gggcagccgc gacgacatcg       300
tgtacgtgcc cgagcccatg acctactggc gcgtgctggg cgccagcgag accatcgcca       360
acatctacac cacccagcac cgcctggacc aaggcgagat cagcgccggc gacgccgccg       420
tggtgatgac cagcgcccag attacaatgg gcatgcccta cgccgtgacc gacgccgtgc       480
tggcaccaca catcggcggc gaggccggca gcagccacgc accaccacca gcactgaccc       540
tgatcttcga ccggcaccca atcgcacacc tgctgtgcta cccggcagca cgctacctga       600
tgggctccat gacaccacaa gccgtgctgg ccttcgtggc cctgatccca ccaacactgc       660
ccggcaccaa catcgtgctg ggcgcccgc ccgaggaccg ccacatcgac cgcctggcca       720
agcgccagcg ccccggcgag cgcctggacc tggccatgct ggccgccatc cgccgcgtgt       780
acggcctgct ggccaacacc gtgcgctacc tgcagtgcgg cggcagctgg cgcgaggact       840
ggggccagct gagcggcacc gccgtgccac cacagggcgc cgagccacag agcaacgccg       900
gaccacgacc acacatcggc gacaccctgt tcaccctgtt ccgggcacca gagctgctgg       960
caccaaacgg cgacctgtac aacgtgttcg cctgggccct ggacgtgctg gccaagcgcc      1020
tgcgctccat gcacgtgttc atcctggact acgaccagtc accggccggc tgccgcgacg      1080
ccctgctgca gctgaccagc ggcatggtgc agacccacgt gacaacaccc ggcagcatcc      1140
caacaatctg cgacctggcc cgcaccttcg cccgcgagat gggcgaggcc aactaatagg      1200
gatccctcga gaagcttgtc a                                                1221

<210> SEQ ID NO 19
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gtcagcggcc gcaccggtac gcgtccacca tggccctgca gaaaaagctg gaagagctgg        60
aactggatgg cagctacccc ggccaccagc acgccagcgc cttcgaccag gccgcccgca       120
gccgcggcca cagcaacggc agcaccgcac tgcggccagg atctcagcag gaggccaccg       180
aggtgcgccc cgagcagaag atgcccaccc tgctgcgcgt gtacatcgac ggaccacacg       240
gcatgggcaa gaccaccacc acccagctgc tggtggccct gggcagccgc gacgacatcg       300
tgtacgtgcc cgagcccatg acctactggc gcgtgctggg cgccagcgag accatcgcca       360
acatctacac cacccagcac cgcctggacc aaggcgagat cagcgccggc gacgccgccg       420

```
tggtgatgac cagcgcccag attacaatgg gcatgccta cgccgtgacc gacgccgtgc      480
tggcaccaca catcggcggc gaggccggca gcagccacgc accaccacca gcactgaccc      540
tgatcttcga ccggcaccca atcttcgcac tgctgtgcta cccggcagca cgctacctga      600
tgggctccat gacaccacaa gccgtgctgg ccttcgtggc cctgatccca ccaacactgc      660
ccggcaccaa catcgtgctg ggcgccctgc ccgaggaccg ccacatcgac cgcctggcca      720
agcgccagcg ccccggcgag cgcctggacc tggccatgct ggccgccatc cgccgcgtgt      780
acggcctgct ggccaacacc gtgcgctacc tgcagtgcgg cggcagctgg cgcgaggact      840
ggggccagct gagcggcacc gccgtgccac acagggcgc cgagccacag agcaacgccg      900
gaccacgacc acacatcggc gacccctgt tcaccctgtt ccgggcacca gagctgctgg      960
caccaaacgg cgacctgtac aacgtgttcg cctgggccct ggacgtgctg ccaagcgcc     1020 tgcgctccat gcacgtgttc atcctggact acgaccagtc accggccggc tgccgcgacg     1080
ccctgctgca gctgaccagc ggcatggtgc agacccacgt gacaacaccc ggcagcatcc     1140
caacaatctg cgacctggcc cgcaccttcg cccgcgagat gggcgaggcc aactaatagg     1200
gatccctcga agcttgtc a                                                1221

<210> SEQ ID NO 20
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gtcagcggcc gcaccggtac gcgtccacca tggctctgca gaaaaagctg gaagagctgg       60
aactggatgg ctcttatcct ggacatcagc atgcttctgc ttttgatcag gctgccagat      120
ctagaggaca ttctaatggc agcacagcac tgcggccagg atctcagcag gaagctacag      180
aagtgagacc tgaacagaaa atgcctacac tgctgagagt gtatattgat ggaccacatg      240
gaatgggaaa acaaccaca acccagctgc tggtggctct cggatctaga gatgatattg      300
tgtatgtgcc tgaacctatg acatattgga gagtgctggg agcttctgaa acaattgcta      360
atatctatac aacacagcat agactggatc aaggagaaat ttctgccgga gatgctgccg      420
tggtgatgac atctgctcag attacaatgg gaatgcctta tgctgtgaca gatgctgtgc      480
tggcaccaca tattggaggc gaagctgaa gctctcatgc accaccacca gcactgacac      540
tgatttttga tcggcatcca attgcacatc tgctgtgtta ccggcagca agatatctga      600 tgggaagcat gacaccacaa gccgtgctgg cttttgtggc tctgattcca ccaacactgc      660
ctggaacaaa catcgtgctg ggagctctgc ctgaagatag acatatcgat cggctggcca      720
aacggcagag acctggagaa cggctggatc tggccatgct ggctgccatt cggagagtgt      780
atggcctgct ggctaacaca gtgagatatc tgcagtgtgg aggctcttgg agagaggatt      840
ggggacagct gtctggcaca gctgtgccac acagggagc cgaaccacag agcaatgctg      900
gaccacgacc acatatcgga gacacactgt ttcacactgtt tcgggcacca gaactgctgg      960
caccaaatgg agacctgtac aacgtgtttg cctgggctct ggatgtgctg gctaacggc     1020 tgagatctat gcatgtgttt atcctggact atgatcagtc accggccgga tgtcgcgatg     1080
ccctgctgca gctgacatct gggatggtgc agacacatgt gacaacacct ggatctatcc     1140
caacaatctg tgatctggct agaacattcg ctagggagat gggagaggcc aactaatgag     1200
```

```
gatccctcga agcttgtc a                                              1221
```

<210> SEQ ID NO 21
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
gtcagcggcc gcaccggtac gcgtccacca tggctctgca gaaaaagctg aagagctgg     60
aactggatgg ctcttatcct ggacatcagc atgcttctgc ttttgatcag gctgccagat   120
ctagaggaca ttctaatggc agcacagcac tgcggccagg atctcagcag gaagctacag   180
aagtgagacc tgaacagaaa atgcctacac tgctgagagt gtatattgat ggaccacatg   240
gaatgggaaa aacaaccaca acccagctgc tggtggctct cggatctaga gatgatattg   300
tgtatgtgcc tgaacctatg acatattgga gagtgctggg agcttctgaa acaattgcta   360
atatctatac aacacagcat agactggatc aaggagaaat ttctgccgga gatgctgccg   420
tggtgatgac atctgctcag attacaatgg aatgcctta tgctgtgaca gatgctgtgc    480
tggcaccaca tattggaggc gaagctggaa gctctcatgc accaccacca gcactgacac   540
tgattttga tcggcatcca attttcgcac tgctgtgtta tccggcagca agatatctga    600
tgggaagcat gacaccacaa gccgtgctgg cttttgtggc tctgattcca ccaacactgc    660
ctggaacaaa catcgtgctg ggagctctgc ctgaagatag acatatcgat cggctggcca   720
aacggcagag acctggagaa cggctggatc tggccatgct ggctgccatt cggagagtgt   780
atggcctgct ggctaacaca gtgagatatc tgcagtgtgg aggctcttgg agagaggatt   840
ggggacagct gtctggcaca gctgtgccac acagggagc cgaaccacag agcaatgctg     900
gaccacgacc acatatcgga gacacactgt ttacactgtt tcgggcacca gaactgctgg   960
caccaaatgg agacctgtac aacgtgtttg cctgggctct ggatgtgctg gctaaacggc  1020
tgagatctat gcatgtgttt atcctggact atgatcagtc accggccgga tgtcgcgatg  1080
ccctgctgca gctgacatct gggatggtgc agacacatgt gacaacacct ggatctatcc  1140
caacaatctg tgatcggct agaacattcg ctagggagat gggagaggcc aactaatgag   1200
gatccctcga agcttgtc a                                              1221
```

<210> SEQ ID NO 22
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
gtcagcggcc gcaccggtac gcgtccacca tggccagcta ccccggccac cagcacgcca     60
gcgccttcga ccaggccgcc cgcagccgcg gccacagcaa cggcagcacc gcactgcggc   120
caggatctca gcaggaggcc accgaggtgc gccccgagca agatgccc accctgctgc    180
gcgtgtacat cgacggacca cacggcatgg gcaagaccac caccacccag ctgctggtgg   240
ccctgggcag ccgcgacgac atcgtgtacg tgcccgagcc catgacctac tggcgcgtgc   300
tgggcgccag cgagaccatc gccaacatct acaccaccca gcaccgcctg gaccaaggcg   360
```

```
agatcagcgc cggcgacgcc gccgtggtga tgaccagcgc ccagattaca atgggcatgc    420
cctacgccgt gaccgacgcc gtgctggcac cacacatcgg cggcgaggcc ggcagcagcc    480
acgcaccacc accagcactg accctgatct tcgaccggca cccaatcgca cacctgctgt    540 gctaccggc agcacgctac ctgatgggct ccatgacacc acaagccgtg ctggccttcg     600
tggccctgat cccaccaaca ctgcccggca ccaacatcgt gctgggcgcc ctgcccgagg    660
accgccacat cgaccgcctg gccaagcgcc agcgccccgg cgagcgcctg gacctggcca    720
tgctggccgc catccgccgc gtgtacggcc tgctggccaa caccgtgcgc tacctgcagt    780
gcggcggcag ctggcgcgag gactggggcc agctgagcgg caccgccgtg ccaccacagg    840
gcgccgagcc acagagcaac gccggaccac gaccacacat cggcgacacc ctgttcaccc    900
tgttccgggc accagagctg ctggcaccaa acggcgacct gtacaacgtg ttcgcctggg    960
ccctggacgt gctggccaag cgcctgcgct ccatgcacgt gttcatcctg gactacgacc   1020
agtcaccggc cggctgccgc gacgccctgc tgcagctgac cagcggcatg gtgcagaccc   1080
acgtgacaac acccggcagc atcccaacaa tctgcgacct ggcccgcacc ttcgcccgcg   1140
agatgggcga ggccaactaa tagggatccc tcgagaagct tgtca                   1185

<210> SEQ ID NO 23
<211> LENGTH: 36
<212> TYPE: DNA
<213> ORGANISM: Unknown
<220> FEATURE:
<223> OTHER INFORMATION: Description of Unknown: Nuclear
      export signal oligonucleotide

<400> SEQUENCE: 23
ctgcagaaaa agctggaaga gctggaactg gatggc                              36

<210> SEQ ID NO 24
<211> LENGTH: 12
<212> TYPE: PRT
<213> ORGANISM: Unknown
<220> FEATURE:
<223> OTHER INFORMATION: Description of Unknown: Nuclear
      export signal peptide

<400> SEQUENCE: 24

Leu Gln Lys Lys Leu Glu Glu Leu Glu Leu Asp Gly
1               5                   10

<210> SEQ ID NO 25
<211> LENGTH: 10
<212> TYPE: PRT
<213> ORGANISM: Unknown
<220> FEATURE:
<223> OTHER INFORMATION: Description of Unknown: Nuclear
      export targeting moiety peptide

<400> SEQUENCE: 25

Trp Arg Glu Pro Ser Phe Met Ala Leu Ser
1               5                   10
```